US009078899B2

(12) United States Patent
Nordhoff et al.

(10) Patent No.: US 9,078,899 B2
(45) Date of Patent: *Jul. 14, 2015

(54) PYRAZOLYL-BASED CARBOXAMIDES II

(71) Applicant: Grünenthal GmbH, Aachen (DE)

(72) Inventors: Sonja Nordhoff, Aachen (DE); Sebastian Wachten, Hürth (DE); Achim Kless, Aachen (DE); Felix Voss, Aachen (DE); Stefanie Ritter, Köln (DE)

(73) Assignee: GRUENENTHAL GMBH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/152,716

(22) Filed: Jan. 10, 2014

(65) Prior Publication Data

US 2014/0194452 A1    Jul. 10, 2014

(30) Foreign Application Priority Data

Jan. 10, 2013  (EP) ..................................... 13000117

(51) Int. Cl.

| | |
|---|---|
| *A61K 31/505* | (2006.01) |
| *A61K 31/4439* | (2006.01) |
| *A61K 31/4155* | (2006.01) |
| *C07D 239/24* | (2006.01) |
| *C07D 401/02* | (2006.01) |
| *C07D 231/10* | (2006.01) |
| *A61K 31/506* | (2006.01) |
| *A61K 31/415* | (2006.01) |
| *C07D 231/14* | (2006.01) |
| *C07D 401/12* | (2006.01) |
| *C07D 403/12* | (2006.01) |
| *C07D 401/14* | (2006.01) |
| *C07D 401/04* | (2006.01) |

(52) U.S. Cl.
CPC .............. *A61K 31/506* (2013.01); *A61K 31/415* (2013.01); *A61K 31/4439* (2013.01); *C07D 231/14* (2013.01); *C07D 401/04* (2013.01); *C07D 401/12* (2013.01); *C07D 401/14* (2013.01); *C07D 403/12* (2013.01)

(58) Field of Classification Search
CPC ............ A61K 31/505; A61K 31/4439; A61K 31/4155; C07D 239/24; C07D 401/02; C07D 231/10
See application file for complete search history.

(56) References Cited

U.S. PATENT DOCUMENTS

| | | |
|---|---|---|
| 6,958,339 B2 | 10/2005 | Kubota et al. |
| 2006/0100208 A1 | 5/2006 | Makriyannis et al. |

FOREIGN PATENT DOCUMENTS

| | | |
|---|---|---|
| EP | 1176140 A1 | 1/2002 |
| WO | 0121160 A2 | 3/2001 |
| WO | 0121160 A3 | 3/2001 |
| WO | 03035602 A1 | 5/2003 |
| WO | 03037274 A2 | 5/2003 |
| WO | 03037274 A3 | 5/2003 |
| WO | 2005009539 A2 | 2/2005 |
| WO | 2005016877 A2 | 2/2005 |
| WO | 2006067202 A1 | 6/2006 |
| WO | 2007024744 A2 | 8/2006 |
| WO | 2007002559 A1 | 1/2007 |
| WO | 2007043400 A1 | 4/2007 |
| WO | 2007087427 A2 | 8/2007 |
| WO | 2007087441 A2 | 8/2007 |
| WO | 2009011850 A2 | 1/2009 |
| WO | 2009012283 A1 | 1/2009 |
| WO | 2009027393 A2 | 3/2009 |
| WO | 2009052062 A1 | 4/2009 |
| WO | 2009076454 A2 | 6/2009 |
| WO | 2009076454 A3 | 6/2009 |
| WO | 2009089305 A1 | 7/2009 |
| WO | 2010006725 A1 | 1/2010 |
| WO | 2010043676 A1 | 4/2010 |
| WO | 2010122089 A1 | 10/2010 |
| WO | 2011042797 A1 | 4/2011 |
| WO | 2012107434 A1 | 8/2012 |
| WO | 2012139930 A1 | 10/2012 |
| WO | 2012168361 A1 | 12/2012 |

OTHER PUBLICATIONS

European Search Report for EP 13000117.5 dated May 23, 2013.
European Search Report for EP 13000118.3 dated May 23, 2013.
Y. Amemiya, et al., "Preparation of 2-Chloro-5-Nitrobenzamides as Lipid Modulators for Treatment of Osteoporosis and Diabetes", Database Caplus [Online] Chemical Abstracts Service, XP-002696312, Columbus, Ohio, US; 2003.
A. Cherkasov, "Targeting the Binding Function 3 (BF3) Site of the Human Androgen Receptor through Virtual Screening", Database Caplus [Online] Chemical Abstracts Service, XP-002696311, Columbus, Ohio, US; 2011.
N. Lack, et al., "Targeting the Binding Function 3 (BF3) Site of the Human Androgen Receptor through Virtual Screening", Journal of Medicinal Chemistry, American Chemical Society, Nov. 2011, vol. 54, No. 24, pp. 8563-8573.
L. A. T. Cleghorn, et al., "Identification of Inhibitors of the Leishmania cdc2-Related Protein Kinase CRK3", ChemMedChem, vol. 6, No. 12, Dec. 2011, pp. 2214-2224, Weinheim.
S. Feske, "Calcium Signalling in Lymphocyte Activation and Disease", Department of Pathology New York University School of Medicine, Nature Publishing Group, vol. 7, pp. 690-706, online, Sep. 2007.

(Continued)

*Primary Examiner* — Samantha Shterengarts
(74) *Attorney, Agent, or Firm* — Norris McLaughlin & Marcus, P.A.

(57) ABSTRACT

The invention relates to pyrazolyl-based carboxamide compounds useful as ICRAC inhibitors, to pharmaceutical compositions containing these compounds and to these compounds for the use in the treatment and/or prophylaxis of diseases and/or disorders, in particular inflammatory diseases and/or inflammatory disorders.

19 Claims, No Drawings

(56) References Cited

OTHER PUBLICATIONS

S. Feske, et al., "A Mutation in Orai1 Causes Immune Deficiency by Abrogating CRAC Channel Function", Nature Publishing Group, vol. 44, pp. 179-185, May 2006, online.

Y. Gwak, et al., "Biochemical and Functional Characterization of Orai Proteins", Journal of Biological Chemistry, vol. 282, No. 22, Jun. 1, 2007, pp. 16232-16243, USA.

M. Hoth, et al., "Depletion of Intracellular Calcium Stores Activates a Calcium Current in Mast Cells", Letters to Nature, vol. 355, pp. 353-356, Jan. 23, 1992, online.

J. Ren, et al., "Regioselective Synthesis and Base Catalyzed Transacylation of Substituted 1H-Pyrazole-4-carboxamides", Chinese Journal of Chemistry, 2002, vol. 20, pp. 96-102.

H. H. Kerschbaum, et al., "Single-Channel Recording of a Store-Operated Ca 2+ Channel in Jurkat T Lymphocytes", Science, www.sciencemag.org, vol. 283, pp. 836-839, Feb. 5, 1999.

M. Oh-Hora, et al., "Calcium Signaling in Lymphocytes", Curr Opin Immunol, National Institutes of Health, Jun. 2008, pp. 250-258.

C. Peinelt, et al., "Amplification of CRAC current by STIM1 and CRACM1(Orai1)", Nature Cell Biology, vol. 8, No. 7, pp. 771-773, Jul. 2006, Nature Publishing Group, online.

S. Plescia, et al., "Some Acetyl Substituted Pyrazolo [1,5-a] pyrimidin-5(4H)one Derivatives", Journal of Heterocyclic Chemistry, vol. 11, No. 4, pp. 623-626, Aug. 1974, Italy.

M. Prakriya, et al., "Orai1 is an essential pore subunit of the CRAC channel", Letters to Nature, Nature Publishing Group, vol. 443, pp. 230-233, Sep. 2006, online.

J. Soboloff, et al., "Orai1 and STIM Reconstitute Store-operated Calcium Channel Function", Journal of Biological Chemistry, vol. 281, No. 31, pp. 20661-20665, Jul. 2006, online.

M. Vig, et al., "CRACM1 Multimers Form the Ion-Selective Pore of the CRAC Channel", Current Biology 16, pp. 2073-2079, Oct. 24, 2006, online.

M. Hoth, et al., Calcium Release-Activgated Calcium Current in Rat Mast Cells, Journal of Physiology, pp. 359-386, 1993, Great Brittain.

A. Lepple-Wienhues, et al., "Conductance and Permeation of Monovalent Cations through Depletion-Activated CA2+ Channels (ICRAC) in Jurkat T Cells", Biophysical Journal, vol. 71, pp. 787-794, Aug. 1996, USA.

R. Lewis, "Store-Operated Calcium Channels", Advances in Second Messenger and Phosphoprotein Reseach, vol. 33, pp. 279-307, 1999, USA.

Z. Li, et al., "Mapping the Interacting Domains of STIM1 and Orai1 in CA2+ Release-activated CA2+ Channel Activation", Journal of Biological Chemistry, vol. 282, No. 40, pp. 29448-29456, Oct. 5, 2007, online.

R. M. Luik, et al., "The Elementary Unit of Store-operated CA2+ Entry: Local Activation of CRAC Channels by STIM1 at ER-plasma Membrane Junctions", The Journal of Cell Biology, vol. 174, No. 6, pp. 815-825, Sep. 11, 2006, online.

G. N. Lipunova. et al., "Flourine-Containing Heterocycles: XII. Flourine-Containing Quinazolan-4-ones and Azolo [a] quinazolinone Derivatives", Russian Journal of Organic Chemistry, vol. 41, No. 7, 2005, pp. 1071-1080.

J. Liou, et al., "Stim Is a Ca2+ Sensor Essential for Ca2+-Store-Depletion-Triggered Ca2+ Influx", National Institutes of Health, Jul. 2005, pp. 1235-1241.

A. B. Parekh, et al., "Store Depletion and Calcium Influx", Physiological Reviews, The American Physiological Society, vol. 77, No. 4, pp. 901-930, Oct. 1997, USA.

J. W. Putney, JR, et al., "A Model for Receptor-Regulated Calcium Entry", Cell Calcium 7, pp. 1-12, 1986, USA.

J. Roos, et al., "STIM1, an Essential and Conserved Component of Store-operated Ca2+ Channel Function", The Journal of Cell Biology, vol. 169, No. 3, May 9, 2005, pp. 435-445, online.

M. M. Wu, et al., "Ca2+ store depletion causes STIM1 to accumulate in ER regions closely associated with the plasma membrane", The Journal of Cell Biology, vol. 174, No. 6, Sep. 11, 2006, pp. 803-813, online.

S. L. Zhang, et al., "STIM1 is a CA2+ sensor that activates CRAC channels and migrates from the Ca2+ store to the plasma membrane", Letters to Nature, Nature Publishing Group, vol. 437, Oct. 6, 2005, pp. 902-905, online.

S. L. Zhang, et al., "Genome-wide RNAi screen of Ca2+ influx identifies genes that regulate Ca2+ release-activated Ca2+ channel activity", PNAS, vol. 103, No. 24, pp. 9357-9362, The National Academy of Sciences of the USA, Jun. 13, 2006.

A. B. Parekh, et al., "Store-Operated Calcium Channels", Physiological Reviews, The American Physiological Society, vol. 85; pp. 757-810, 2005, USA.

ized Calcium concentration within i.e. the endoplasmic reticulum (ER). The latter have been demonstrated to serve as the main Calcium entry mechanisms in non-excitable cells.

PYRAZOLYL-BASED CARBOXAMIDES II

This application claims priority to the European patent application EP 13000117.5 filed Jan. 10, 2013.

FIELD OF THE INVENTION

The invention relates to biologically active compounds, namely substituted pyrazol-3-yl-carboxamides bearing a substituted phenyl or 6-membered heteroaryl moiety, useful for inhibition of the Calcium Release Activated Calcium channel (CRAC) and hence for inhibition of the Calcium Release Activated Calcium current (ICRAC), to pharmaceutical compositions containing these compounds and also to these compounds for use in immuosupression and in the treatment and/or prophylaxis of conditions, diseases and/or disorders, in particular immune disorders, inflammatory conditions and allergic diseases.

BACKGROUND OF THE INVENTION

Calcium-conducting channels in the plasma membrane can appear very diverse (Parekh & Putney 2005) including voltage-gated ion channels (VOC's), receptor-operated ion channels (ROC's), but also store-operated channels (SOC's; Putney, 1986) that are activated in response to a decrease of the intraluminal Calcium concentration within i.e. the endoplasmic reticulum (ER). The latter have been demonstrated to serve as the main Calcium entry mechanisms in non-excitable cells.

Amongst the distinct SOCs, the CRAC current (ICRAC) is certainly characterized best and displays biophysical features such as high selectivity for Calcium ions, low conductance, and inward rectification (Hoth & Penner, 1992; Hoth & Penner, 1993; Parekh & Penner, 1997; Lepple-Wienhues & Cahalan, 1996; Kerschbaum & Cahalan, 1999). There's substantial evidence that the channels conducting CRAC predominantly rely on two proteins, Orai1 and Stim1 (Roos et al., 2005; Feske et al., 2006; Peinelt et al., 2006). Orai1 constitutes the channel pore within the plasma membrane (Prakriya et al., 2006; Vig et al., 2006), whereas Stim1 has been demonstrated to function as the sensor of the luminal Calcium concentration (Liou et al., 2005; Zhang et al., 2006).

In a physiological setting, ICRAC is activated in response to the engagement of cell-surface receptors that positively couple to phospholipase C (PLC). PLC increases the concentration of the soluble messenger inositol-1,4,5-trisphosphate (IP3), which opens ER membrane-resident IP3-receptors. Thus, IP3 triggers the release of Calcium from internal stores resulting in a drop of the luminal Calcium concentration (Lewis, 1999), which is sensed by Stim1. The Stim1 molecule undergoes conformational changes inducing clustering with other Stim1 molecules just underneath the plasma membrane. At these sites, Stim1 can open the Orai1 pore by bridging the ER-PM gap with its C-terminal tail (Zhang et al., 2005; Luik et al., 2006; Soboloff et al. 2006, Wu et al. 2006; Li et al., 2007).

The above described process serves in signaling pathways of immune cells such as lymphocytes and mast cells. I.e. the activation of antigen or Fc receptors stimulates the release of Calcium from intracellular stores, and subsequent activation of ICRAC that impacts on downstream processes such as gene expression and cytokine release (Feske, 2007; Gwack et al., 2007; Oh-hora & Rao 2008).

The major contribution ICRAC provides to these signaling events has been convincingly demonstrated in patients suffering from severe combined immunodeficiency (SCID) due to a defect in T-cell activation. T cells and fibroblasts from these patients exhibited a strong attenuation of store-operated Calcium entry carried by ICRAC (Feske et al., 2006). This suggests CRAC channel modulators to serve as treatment in disease states caused by activated inflammatory cells.

The activation of antigen or Fc receptors stimulates the release of Calcium from intracellular stores and subsequent, sustained activation of ICRAC. Calcium carried by ICRAC activates calcineurin (CaN), which dephosphorylates the transcription factor NFAT. Upon dephosphorylation, NFAT shuttles into the nucleus and regulates gene expression in various ways depending on the nature of the stimulus as well as on the cell/tissue type.

NFAT participates in the transactivation of cytokine genes that regulate T-cell proliferation and other genes that control immune responses. Taking into account that the expression of cytokines such as IL-2, IL-4, IL-5, IL-8, IL-13, tumor necrosis factor alpha (TNFα), granulocyte colony-stimulating factor (G-CSF), and gamma-interferon (INFγ) is prone to be controlled via transcriptional elements for NFAT, the impact of the ICRAC/CaN/NFAT signaling pathway on pro-inflammatory processes becomes apparent. The inhibition of this pathway has been demonstrated to be efficacious in patients by the use of drugs such as CsA and FK506, which act by inhibiting CaN.

A hallmark of ICRAC signaling in immune cells is that downstream processes such as gene expression rely on sustained Calcium entry rather than transient signals. However, Calcium entry is essential for other processes that can be independent of CaN/NFAT. Direct, Calcium-mediated release of substances (degranulation) such as histamine, heparin, and TNFα occur in i.e. mast cells, and are of rather acute nature. On the molecular level, this already points towards a differentiation potential for ICRAC blockers from calcineurin inhibitors.

Recent findings suggest that CRAC channel modulators can serve as treatment in disease states caused by the activation of inflammatory cells without side effects observed under treatments with i.e. steroids. Such diseases may include but are not limited to asthma, chronic obstructive pulmonary disease, rheumatoid arthritis, inflammatory bowel disease, glomerulonephritis, neuroinflammatory diseases such as multiple sclerosis, and disorders of the immune system.

U.S. Pat. No. 6,958,339, WO 2009/076454 A1, WO 2009/089305 A1, and WO 2010/122089 A1 each disclose a series of pyrazole carboxamide derivatives that are said to possess CRAC channel inhibitory activity which are believed to be useful in the treatment of allergic, inflammatory or autoimmune diseases. Other small molecules possessing structurally different scaffolds as ICRAC inhibitors are known for instance from WO2005/009539, WO 2007/087427 A2 and WO 2007/087441 A2.

Pyrazole carboxamides as biologically active compounds are also known in the art, for instance from EP 1176140 B1, US 2006/0100208 A1, WO 2005/016877 A2, WO 2006/076202 A1, WO 2007/002559 A1, WO 2007/024744 A2, WO 2009/011850 A2 and WO 2009/027393.

SUMMARY OF THE INVENTION

The present invention describes a new class of small molecule that is useful for the inhibition of the calcium release activated calcium channel current (thereafter ICRAC inhibitors).

It was therefore an object of the invention to provide novel compounds, preferably having advantages over the prior-art compounds. The compounds should be suitable in particular as pharmacological active ingredients in pharmaceutical compositions, preferably in pharmaceutical compositions for the treatment and/or prophylaxis of disorders or diseases which are at least partially mediated by CRAC channels.

This object is achieved by the subject matter described herein.

It has surprisingly been found that the substituted compounds of general formula (I), as given below, display potent inhibitory activity against to CRAC channels and are therefore particularly suitable for the prophylaxis and/or treatment of disorders or diseases which are at least partially mediated by CRAC channels.

A first aspect of the present invention therefore relates to a compound of general formula (I),

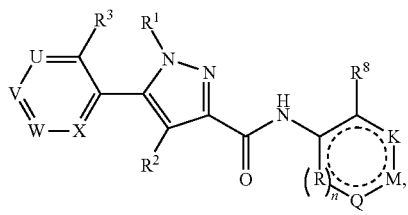

wherein
R$^1$ denotes
  C$_{1-4}$-aliphatic residue, unsubstituted or mono- or polysubstituted; or
  C$_{3-6}$-cycloaliphatic residue or a 3 to 7 membered heterocycloaliphatic residue, in each case unsubstituted or mono- or polysubstituted and in each case optionally connected via a C$_{1-4}$ aliphatic group, which in turn may be unsubstituted or mono- or polysubstituted;
    with the proviso that if R$^1$ represents a 3 to 7 membered heterocycloaliphatic residue, said 3 to 7 membered heterocycloaliphatic residue is connected to the remaining part of the structure according to general formula (I) via a carbon atom of the 3 to 7 membered heterocycloaliphatic residue;
R$^2$ denotes H; F; Cl; Br; I; NO$_2$; CN; CF$_3$; CF$_2$H; CFH$_2$; R$^{13}$; OH; O—R$^{13}$; NH$_2$; N(H)R$^{13}$; N(R$^{13}$)$_2$;
U represents C—R$^4$ or N or N$^+$—O$^-$, V represents C—R$^5$ or N or N$^+$—O$^-$, W represents C—R$^6$ or N or N$^+$—O$^-$, and X represents C—R$^7$ or N or N$^+$—O$^-$,
with the proviso that 0, 1, 2 or 3 of variables T, U, V, W and X independently of one another represent(s) either N or N$^+$—O$^-$, whereof 0 or 1 of variables T, U, V, W and X independently of one another represent(s) N$^+$—O$^-$ and
with the proviso that at least one of U, V and W does not represent N,
wherein
R$^4$, R$^5$ and R$^6$ are independently of one another selected from the group consisting of H; F; Cl; Br; I; NO$_2$; CN; CF$_3$; CF$_2$H; CFH$_2$; CF$_2$Cl; CFCl$_2$; C$_{1-8}$-aliphatic residue, unsubstituted or mono- or polysubstituted; C(=O)OH; C(=O)—R$^{13}$; C(=O)R$^{14}$; C(=O)—OR$^{13}$; C(=O)—OR$^{14}$; C(=O)—N(H)(OH); C(=N—OH)—H; C(=N—OH)—R$^{13}$; C(=N—OH)—R$^{14}$; C(=N—O—R$^{13}$)—H; C(=N—O—R$^{13}$)—R$^{13}$; C(=N—O—R$^{13}$)—R$^{14}$; C(=O)NH$_2$; C(=O)—N(H)R$^{13}$; C(=O)—N(R$^{13}$)$_2$; C(=O)—N(H)R$^{14}$; C(=O)—N(R$^{14}$)$_2$; C(=O)—N(R$^{13}$)(R$^{14}$); C(=O)—N(R$^a$)(R$^b$); OH; OR$^{13}$; OCF$_3$; OCF$_2$H; OCFH$_2$; OCF$_2$Cl; OCFCl$_2$; OR$^{14}$; O—C(=O)R$^{13}$; O—C(=O)R$^{14}$; O—C(=O)—N(H)R$^{13}$; O—C(=O)—N(H)R$^{14}$; O—C(=O)—N(R$^{13}$)$_2$; O—C(=O)—N(R$^{14}$)$_2$;
O—C(=O)—N(R$^{13}$)(R$^{14}$); O—C(=O)—N(R$^a$)(R$^b$); NH$_2$; N(H)R$^{13}$; N(R$^{13}$)$_2$; N(H)R$^{14}$; N(R$^{14}$)$_2$; N(R$^{13}$)(R$^{14}$); N(R$^a$)(R$^b$); NH—C(=O)—R$^{14}$; NH—C(=O)—R$^{13}$; N(R$^{13}$)—C(=O)—R$^{13}$; N(R$^{13}$)—C(=O)—R$^{14}$; NH—S(=O)$_2$—R$^{13}$; N(R$^{13}$)—S(=O)$_2$—R$^{13}$; NH—S(=O)$_2$—R$^{14}$; N(R$^{13}$)—S(=O)$_2$—R$^{14}$; N(H)—C(=O)—OR$^{13}$; N(H)—C(=O)—OR$^{14}$; N(R$^{13}$)—C(=O)—OR$^{13}$; N(R$^{13}$)—C(=O)—OR$^{14}$; N(H)—C(=O)—NH$_2$; N(H)—C(=O)—N(H)R$^{13}$; N(H)—C(=O)—N(H)R$^{14}$; N(H)—C(=O)—N(R$^{13}$)$_2$; N(H)—C(=O)—N(R$^{14}$)$_2$; N(H)—C(=O)—N(R$^{13}$)(R$^{14}$); N(H)—C(=O)—N(R$^a$)(R$^b$); N(R$^{13}$)—C(=O)—NH$_2$; N(R$^{13}$)—C(=O)—N(H)R$^{13}$; N(R$^{13}$)—C(=O)—N(H)R$^{14}$; N(R$^{13}$)—C(=O)—N(R$^{13}$)$_2$; N(R$^{13}$)—C(=O)—N(R$^{14}$)$_2$; N(R$^{13}$)—C(=O)—N(R$^{13}$)(R$^{14}$); N(R$^{13}$)—C(=O)—N(R$^a$)(R$^b$); SH; S—R$^{13}$; SCF$_3$; S—R$^{14}$; S(=O)$_2$OH; S(=O)$_2$—R$^{13}$; S(=O)$_2$—R$^{14}$; S(=O)—R$^{13}$; S(=O)—R$^{14}$; S(=O)$_2$—OR$^{13}$; S(=O)$_2$—OR$^{14}$; S(=O)$_2$—N(H)(R$^{13}$); S(=O)$_2$—N(R$^{13}$)$_2$; S(=O)$_2$—N(H)(R$^{14}$); S(=O)$_2$—N(R$^{13}$)(R$^{14}$); S(=O)$_2$—N(R$^a$)(R$^b$);

R$^3$ and R$^7$ are independently of one another selected from the group consisting of H; F; Cl; Br; I; NO$_2$; CN; CF$_3$; CF$_2$H; CFH$_2$; CF$_2$Cl; CFCl$_2$; R$^{13}$; R$^{14}$; C(=O)OH; C(=O)—R$^{13}$; C(=O)R$^{14}$; C(=O)—OR$^{13}$; C(=O)—OR$^{14}$; C(=O)—N(H)(OH); C(=N—OH)—H; C(=N—OH)—R$^{13}$; C(=N—OH)—R$^{14}$; C(=N—O—R$^{13}$)—H; C(=N—O—R$^{13}$)—R$^{13}$; C(=N—O—R$^{13}$)—R$^{14}$; C(=O)NH$_2$; C(=O)—N(H)R$^{13}$; C(=O)—N(R$^{13}$)$_2$; C(=O)—N(H)R$^{14}$; C(=O)—N(R$^{14}$)$_2$; C(=O)—N(R$^{13}$)(R$^{14}$); C(=O)—N(R$^a$)(R$^b$); OH; OR$^{13}$; OCF$_3$; OCF$_2$H; OCFH$_2$; OCF$_2$Cl; OCFCl$_2$; OR$^{14}$; O—C(=O)R$^{13}$; O—C(=O)R$^{14}$; O—C(=O)—N(H)R$^{13}$; O—C(=O)—N(H)R$^{14}$; O—C(=O)—N(R$^{13}$)$_2$; O—C(=O)—N(R$^{14}$)$_2$; O—C(=O)—N(R$^{13}$)(R$^{14}$); O—C(=o)—N(R$^a$)(R$^b$); NH$_2$; N(H)R$^{13}$; N(R$^{13}$)$_2$; N(H)R$^{14}$; N(R$^{14}$)$_2$; N(R$^{13}$)(R$^{14}$); N(R$^a$)(R$^b$); NH—C(=O)—R$^{14}$; NH—C(=O)—R$^{13}$; N(R$^{13}$)—C(=O)—R$^{13}$; N(R$^{13}$)—C(=O)—R$^{14}$; NH—S(=O)$_2$—R$^{13}$; N(R$^{13}$)—S(=O)$_2$—R$^{13}$; NH—S(=O)$_2$—R$^{14}$; N(R$^{13}$)—S(=O)$_2$—R$^{14}$; N(H)—C(=O)—OR$^{13}$; N(H)—C(=O)—OR$^{14}$; N(R$^{13}$)—C(=O)—OR$^{13}$; N(R$^{13}$)—C(=O)—OR$^{14}$; N(H)—C(=O)—NH$_2$; N(H)—C(=O)—N(H)R$^{13}$; N(H)—C(=O)—N(H)R$^{14}$; N(H)—C(=O)—N(R$^{13}$)$_2$; N(H)—C(=O)—N(R$^{14}$)$_2$; N(H)—C(=O)—N(R$^{13}$)(R$^{14}$); N(H)—C(=O)—N(R$^a$)(R$^b$); N(R$^{13}$)—C(=O)—NH$_2$; N(R$^{13}$)—C(=O)—N(H)R$^{13}$; N(R$^{13}$)—C(=O)—N(H)R$^{14}$; N(R$^{13}$)—C(=O)—N(R$^{13}$)$_2$; N(R$^{13}$)—C(=O)—N(R$^{14}$)$_2$; N(R$^{13}$)—C(=O)—N(R$^{13}$)(R$^{14}$); N(R$^{13}$)—C(=O)—N(R$^a$)(R$^b$); SH; S—R$^{13}$; SCF$_3$; S—R$^{14}$; S(=O)$_2$OH; S(=O)$_2$—R$^{13}$; S(=O)$_2$—R$^{14}$; S(=O)—R$^{13}$; S(=O)—R$^{14}$; S(=O)$_2$—OR$^{13}$; S(=O)$_2$—OR$^{14}$; S(=O)$_2$—N(H)(R$^{13}$); S(=O)$_2$—N(R$^{13}$)$_2$; S(=O)$_2$—N(H)(R$^{14}$); S(=O)$_2$—N(R$^{13}$)(R$^{14}$); S(=O)$_2$—N(R$^a$)(R$^b$);

with the proviso that R$^3$ does not represent H;
n represents 0 or 1,
wherein, if n represents 1, then
  K represents C—R$^9$ or N or N$^+$—O$^-$,
  M represents C—R$^{10}$ or N or N$^+$—O$^-$,
  Q represents C—R$^{11}$ or N or N$^+$—O$^-$, and
  R represents C—R$^{12}$ or N or N$^+$—O$^-$,
    with the proviso that 0, 1, 2 or 3 of variables K, M, Q and R independently of one another represent(s) either N or N$^+$—O$^-$, whereof 0 or 1 of variables K, M, Q and R independently represents N$^+$—O$^-$,
wherein, if n represents 0, then
  K represents C—R$^9$ or N or N$^+$—O$^-$ or O or S or NH or N(C$_{1-4}$-aliphatic residue), M represents C—$R^{10}$ or N or $N^+$—$O^-$ or O or S or NH or N($C_{1-4}$-aliphatic residue) and Q represents C—$R^{11}$ or N or $N^+$—$O^-$ or O or S or NH or N($C_{1-4}$-aliphatic residue), with the proviso that one of K, M and Q represents O or S or NH or N($C_{1-4}$-aliphatic residue) and the remaining of K, M and Q independently represent C—$R^9$, respectively C—$R^{10}$, respectively O—$R^{11}$ or N or $N^+$—$O^-$ and with the proviso that 0, 1 or 2 of variables K, M and Q independently of one another represent either N or $N^+$—$O^-$, whereof 0 or 1 of variables K, M and Q represents $N^+$—$O^-$, wherein $R^8$ is selected from F, Cl, $CF_3$, $CF_2H$, $CFH_2$, $CH_3$, CN, $OCH_3$, $OCF_2H$, $OCFH_2$, and $OCF_3$, and wherein $R^9$, $R^{10}$, $R^{11}$ and $R^{12}$ are independently of one another selected from the group consisting of H; F; Cl; Br; I; $NO_2$; CN; $CF_3$; $CF_2H$; $CFH_2$; $CF_2Cl$; $CFCl_2$; $R^{13}$; $R^{14}$; C(=O)OH; C(=O)—$R^{13}$; C(=O)$R^{14}$; C(=O)—$OR^{13}$; C(=O)—$OR^{14}$; C(=O)—N(H)(OH); C(=N—OH)—H; C(=N—OH)—$R^{13}$; C(=N—OH)—$R^{14}$; C(=N—O—$R^{13}$)—H; C(=N—O—$R^{13}$)—$R^{13}$; C(=N—O—$R^{13}$)—$R^{14}$; C(=O)$NH_2$; C(=O)—N(H)$R^{13}$; C(=O)—N($R^{13}$)$_2$; C(=O)—N(H)$R^{14}$; C(=O)—N($R^{14}$)$_2$; C(=O)—N($R^{13}$)($R^{14}$); C(=O)—N($R^a$)($R^b$); OH; $OR^{13}$; $OCF_3$; $OCF_2H$; $OCFH_2$; $OCF_2Cl$; $OCFCl_2$; $OR^{14}$; O—C(=O)$R^{13}$; O—C(=O)$R^{14}$; O—C(=O)—N(H)$R^{13}$; O—C(=O)—N(H)$R^{14}$; O—C(=O)—N($R^{13}$)$_2$; O—C(=O)—N($R^{14}$)$_2$; O—C(=O)—N($R^{13}$)($R^{14}$); O—C(=O)—N($R^a$)($R^b$); $NH_2$; N(H)$R^{13}$; N($R^{13}$)$_2$; N(H)$R^{14}$; N($R^{14}$)$_2$; N($R^{13}$)($R^{14}$); N($R^a$)($R^b$); NH—C(=O)—$R^{14}$; NH—C(=O)—$R^{13}$; N($R^{13}$)—C(=O)—$R^{13}$; N($R^{13}$)—C(=O)—$R^{14}$; NH—S(=O)$_2$—$R^{13}$; N($R^{13}$)—S(=O)$_2$—$R^{13}$; NH—S(=O)$_2$—$R^{14}$; N($R^{13}$)—S(=O)$_2$—$R^{14}$; N(H)—C(=O)—$OR^{13}$; N(H)—C(O)—$OR^{14}$; N($R^{13}$)—C(=O)—$OR^{13}$; N($R^{13}$)—C(=O)—$OR^{14}$; N(H)—C(=O)—$NH_2$; N(H)—C(=O)—N(H)$R^{13}$; N(H)—C(=O)—N(H)$R^{14}$; N(H)—C(=O)—N($R^{13}$)$_2$; N(H)—C(=O)—N($R^{14}$)$_2$; N(H)—C(=O)—N($R^{13}$)($R^{14}$); N(H)—C(=O)—N($R^a$)($R^b$); N($R^{13}$)—C(=O)—$NH_2$; N($R^{13}$)—C(=O)—N(H)$R^{13}$; N($R^{13}$)—C(=O)—N(H)$R^{14}$; N($R^{13}$)—C(=O)—N($R^{13}$)$_2$; N($R^{13}$)—C(=O)—N($R^{14}$)$_2$; N($R^{13}$)—C(=O)—N($R^{13}$)($R^{14}$); N($R^{13}$)—C(=O)—N($R^a$)($R^b$); SH; S—$R^{13}$; $SCF_3$; S—$R^{14}$; S(=O)$_2$OH; S(=O)$_2$—$R^{13}$; S(=O)$_2$—$R^{14}$; S(=O)—$R^{13}$; S(=O)—$R^{14}$; S(=O)$_2$—$OR^{13}$; S(=O)$_2$—$OR^{14}$; S(=O)$_2$—N(H)($R^{13}$); S(=O)$_2$—N($R^{13}$)$_2$; S(=O)$_2$—N(Fl)($R^{14}$); S(=O)$_2$—N($R^{13}$)($R^{14}$); S(=O)$_2$—N($R^a$)($R^b$);

wherein each $R^{13}$ independently of each other denotes $C_{1-8}$-aliphatic residue, unsubstituted or mono- or polysubstituted;

or $C_{3-6}$-cycloaliphatic residue or 3 to 7 membered heterocycloaliphatic residue, in each case unsubstituted or mono- or polysubstituted;

or $C_{3-6}$-cycloaliphatic residue or 3 to 7 membered heterocycloaliphatic residue, in each case unsubstituted or mono- or polysubstituted, and in each case connected via a $C_{1-4}$-aliphatic residue, unsubstituted or mono- or polysubstituted;

each $R^{14}$ independently of each other denotes aryl and heteroaryl residue, in each case independently of one another unsubstituted or mono- or polysubstituted, or aryl and heteroaryl residue, in each case independently of one another unsubstituted or mono- or polysubstituted and in each case connected via a $C_{1-4}$-aliphatic group, unsubstituted or mono- or polysubstituted;

$R^a$ and $R^b$ together with the N-atom connecting them form a 3 to 7 membered heterocyclic residue, unsubstituted or mono- or polysubstituted;

in which "mono- or polysubstituted" with respect to an "aliphatic group", an "aliphatic residue" a "cycloaliphatic residue" and a "heterocycloaliphatic residue" relates in each case independently of one another, with respect to the corresponding residues or groups, to the substitution of one or more hydrogen atoms each independently of one another by at least one substituent selected from the group consisting of F; Cl; CN; $CF_3$; $CF_2H$; $CFH_2$; $CF_2Cl$; $CFCl_2$; $C_{1-8}$-aliphatic residue; $C_{3-6}$-cycloaliphatic residue; 3 to 7 membered heterocyclic residue; aryl; heteroaryl; aryl, heteroaryl, $C_{3-6}$-cycloaliphatic residue or 3 to 6 membered heterocycloaliphatic, each connected via a $C_{1-4}$-aliphatic group; C(=O)—($C_{1-8}$-aliphatic residue); C(=O)—($C_{3-6}$-cycloaliphatic residue); C(=O)-(3 to 7 membered heterocyclic residue); C(=O)-(aryl); C(=O)-(heteroaryl); C(=O)OH; C(=O)—O($C_{1-8}$-aliphatic residue); C(=O)—O($C_{3-6}$-cycloaliphatic residue); C(=O)—O(3 to 7 membered heterocyclic residue); C(=O)—O(aryl); C(=O)—O(heteroaryl); C(=O)—$NH_2$; C(=O)—N(H)($C_{1-8}$-aliphatic residue); C(=O)—N(H)($C_{3-6}$-cycloaliphatic residue); C(=O)—N(H)(3 to 7 membered heterocyclic residue); C(=O)—N(H)(aryl); C(=O)—N(H)(heteroaryl); C(=O)—N($C_{1-8}$-aliphatic residue)($C_{1-8}$-aliphatic residue); C(=O)—N($C_{1-8}$-aliphatic residue)($C_{3-6}$-cycloaliphatic residue); C(=O)—N($C_{1-8}$-aliphatic residue)(3 to 7 membered heterocyclic residue); C(=O)—N($C_{1-8}$-aliphatic residue)(aryl); C(=O)—N($C_{1-8}$-aliphatic residue)-(heteroaryl); OH; =O; O—($C_{1-8}$-aliphatic residue); O—($C_{3-6}$-cycloaliphatic residue); O-(3 to 7 membered heterocyclic residue); O-(aryl); O-(heteroaryl); $OCF_3$; $OCF_2H$; $OCFH_2$; $OCF_2Cl$; $OCFCl_2$; O—($C_{2-4}$-aliphatic group)-OH; O—($C_{2-4}$-aliphatic group)-O($C_{1-8}$-aliphatic residue); O—C(=O)—($C_{1-8}$-aliphatic residue); O—C(=O)—($C_{3-6}$-cycloaliphatic residue); O—C(=O)-(3 to 7 membered heterocyclic residue); O—C(=O)-(aryl); C(=O)-(heteroaryl); O—C(=O)—$NH_2$; O—C(=O)—N(H)($C_{1-8}$-aliphatic residue); O—C(=O)—N(H)($C_{3-6}$-cycloaliphatic residue); O—C(=O)—N(H)(3 to 7 membered heterocyclic residue); O—C(=O)—N(H)(aryl); O—C(=O)—N(H)-(heteroaryl); O—C(=O)—N($C_{1-8}$-aliphatic residue)($C_{1-8}$-aliphatic residue); O—C(=O)—N($C_{1-8}$-aliphatic residue)-($C_{3-6}$-cycloaliphatic residue); O—C(=O)—N($C_{1-8}$-aliphatic residue)(3 to 7 membered heterocyclic residue); O—C(=O)—N($C_1$-aliphatic residue)(aryl); O—C(=O)—N($C_{1-8}$-aliphatic residue)(heteroaryl); $NH_2$; N(H)($C_{1-8}$-aliphatic residue); N(H)($C_{3-6}$-cycloaliphatic residue); N(H)(3 to 7 membered heterocyclic residue); N(H)(aryl); N(H)(heteroaryl); N($C_{1-8}$-aliphatic residue)($C_{1-8}$-aliphatic residue); N($C_{1-8}$-aliphatic residue)($C_{3-6}$-cycloaliphatic residue); N($C_{1-8}$-aliphatic residue)(3 to 7 membered heterocyclic residue); N($C_{1-8}$-aliphatic residue)(aryl); N($C_{1-8}$-aliphatic residue)(heteroaryl); N(H)—C(=O)—($C_{1-8}$-aliphatic residue); N(H)—C(=O)—($C_{3-6}$-cycloaliphatic residue); N(H)—C(=O)-(3 to 7 membered heterocyclic residue); N(H)—C(=O)-(aryl); N(H)—C(=O)-(heteroaryl); N($C_{1-8}$-aliphatic residue)-C(=O)—($C_{1-8}$-aliphatic residue); N($C_{1-8}$-aliphatic residue)-C(=O)—($C_{3-6}$-cycloaliphatic residue); N($C_{1-8}$-aliphatic residue)-C(=O)-(3 to 7 membered heterocyclic residue); N($C_{1-8}$-aliphatic residue)-C(=O)-(aryl); N($C_{1-8}$-aliphatic residue)-C(=O)-(heteroaryl); N(H)—S(=O)$_2$—($C_{1-8}$-aliphatic residue); N(H)—S(=O)$_2$—($C_{3-6}$-cycloaliphatic residue); N(H)—S(=O)$_2$-(3 to 7 membered heterocyclic residue); N(H)—S(=O)$_2$-(aryl); N(H)—S(=O)$_2$-

(heteroaryl); N($C_{1-8}$-aliphatic residue)-S(=O)$_2$—($C_{1-8}$-aliphatic residue); N($C_{1-8}$-aliphatic residue)-S(=O)$_2$—($C_{3-6}$-cycloaliphatic residue); N($C_{1-8}$-aliphatic residue)-S(=O)$_2$-(3 to 7 membered heterocyclic residue); N($C_{1-8}$-aliphatic residue)-S(=O)$_2$-(aryl); N($C_{1-8}$-aliphatic residue)-S(=O)$_2$-(heteroaryl); N(H)—C(=O)—O($C_{1-8}$-aliphatic residue); N(H)—C(=O)—O($C_{3-6}$-cycloaliphatic residue); N(H)—C(=O)—O(3 to 7 membered heterocyclic residue); N(H)—C(=O)—O(aryl); N(H)—C(=O)—O(heteroaryl); N($C_{1-8}$-aliphatic residue)-C(=O)—O($C_{1-8}$-aliphatic residue); N($C_{1-8}$-aliphatic residue)-C(=O)—O($C_{3-6}$-cycloaliphatic residue); N($C_{1-8}$-aliphatic residue)-C(=O)—O(3 to 7 membered heterocyclic residue); N($C_{1-8}$-aliphatic residue)-C(=O)—O(aryl); N($C_{1-8}$-aliphatic residue)-C(=O)—O(heteroaryl); N(H)—C(=O)—NH$_2$; N(H)—C(=O)—N(H)($C_{1-8}$-aliphatic residue); N(H)—C(=O)—N(H)($C_{3-6}$-cycloaliphatic residue); N(H)—C(=O)—N(H)(3 to 7 membered heterocyclic residue); N(H)—C(=O)—N(H)(aryl); N(H)—C(=O)—N(H)(heteroaryl); N($C_{1-8}$-aliphatic residue)-C(=O)—NH$_2$; N($C_{1-8}$-aliphatic residue)-C(=O)—N(H)($C_{1-8}$-aliphatic residue); N($C_{1-8}$-aliphatic residue)-C(=O)—N(H)($C_{3-6}$-cycloaliphatic residue); N($C_{1-8}$-aliphatic residue)-C(=O)—N(H)(3 to 7 membered heterocyclic residue); N($C_{1-8}$-aliphatic residue)-C(=O)—N(H)(aryl); N($C_{1-8}$-aliphatic residue)-C(=O)—N(H)(heteroaryl); N(H)—C(=O)—N($C_{1-8}$-aliphatic residue)($C_{1-8}$-aliphatic residue); N(H)—C(=O)—N($C_{1-8}$-aliphatic residue)($C_{3-6}$-cycloaliphatic residue); N(H)—C(=O)—N($C_{1-8}$-aliphatic residue)(3 to 7 membered heterocyclic residue); N(H)—C(=O)—N($C_{1-8}$-aliphatic residue)(aryl); N(H)—C(=O)—N($C_{1-8}$-aliphatic residue)-(heteroaryl); N($C_{1-8}$-aliphatic residue)-C(=O)—N($C_{1-8}$-aliphatic residue)($C_{1-8}$-aliphatic residue); N($C_{1-8}$-aliphatic residue)-C(=O)—N($C_{1-8}$-aliphatic residue)($C_{3-6}$-cycloaliphatic residue); N($C_{1-8}$-aliphatic residue)-C(=O)—N($C_{1-8}$-aliphatic residue)(3 to 7 membered heterocyclic residue); N($C_{1-8}$-aliphatic residue)-C(=O)—N($C_{1-8}$-aliphatic residue)(aryl); N($C_{1-8}$-aliphatic residue)-C(=O)—N($C_{1-8}$-aliphatic residue)(heteroaryl); S—($C_{3-6}$-cycloaliphatic residue); S-(3 to 7 membered heterocyclic residue); S-(aryl); S-(heteroaryl); SCF$_3$; S(=O)$_2$OH; S(=O)—($C_{1-8}$-aliphatic residue); S(=O)—($C_{3-6}$-cycloaliphatic residue); S(=O)-(3 to 7 membered heterocyclic residue); S(=O)-(aryl); S(=O)-(heteroaryl); S(=O)$_2$—($C_{1-8}$-aliphatic residue); S(=O)$_2$—($C_{3-6}$-cycloaliphatic residue); S(=O)$_2$-(3 to 7 membered heterocyclic residue); S(=O)$_2$-(aryl); S(=O)$_2$-(heteroaryl); S(=O)$_2$—O($C_{1-8}$-aliphatic residue); S(=O)$_2$—O($C_{3-6}$-cycloaliphatic residue); S(=O)$_2$—O(3 to 7 membered heterocyclic residue); S(=O)$_2$—O(aryl); S(=O)$_2$—O(heteroaryl); S(=O)$_2$—N(H)($C_{1-8}$-aliphatic residue); S(=O)$_2$—N(H)($C_{3-6}$-cycloaliphatic residue); S(=O)$_2$—N(H)(3 to 7 membered heterocyclic residue); S(=O)$_2$—N(H)(aryl); S(=O)$_2$—N(H)(heteroaryl); S(=O)$_2$—N($C_{1-8}$-aliphatic residue)($C_{1-8}$-aliphatic residue); S(=O)$_2$—N($C_{1-8}$-aliphatic residue)($C_{3-6}$-cycloaliphatic residue); S(=O)$_2$—N($C_{1-8}$-aliphatic residue)(3 to 7 membered heterocyclic residue); S(=O)$_2$—N($C_{1-8}$-aliphatic residue)(aryl); S(=O)$_2$—N($C_{1-8}$-aliphatic residue)(heteroaryl);

in which "mono- or polysubstituted" with respect to "aryl" and "heteroaryl" relates, with respect to the corresponding residues, in each case independently of one another, to the substitution of one or more hydrogen atoms each independently of one another by at least one substituent selected from the group consisting of F; Cl; Br; NO$_2$; CN; CF$_3$; CF$_2$H; CFH$_2$; CF$_2$Cl; CFCl$_2$; $C_{1-8}$-aliphatic residue; $C_{3-6}$-cycloaliphatic residue; 3 to 7 membered heterocyclic residue; aryl; heteroaryl; aryl, heteroaryl, $C_{3-6}$-cycloaliphatic residue or 3 to 6 membered heterocycloaliphatic, each connected via a $C_{1-4}$-aliphatic group; C(=O)H; C(=O)—($C_{1-8}$-aliphatic residue); C(=O)—($C_{3-6}$-cycloaliphatic residue); C(=O)-(3 to 7 membered heterocyclic residue); C(=O)-(aryl); C(=O)-(heteroaryl); C(=O)OH; C(=O)—O($C_{1-8}$-aliphatic residue); C(=O)—O($C_{3-6}$-cycloaliphatic residue); C(=O)—O(3 to 7 membered heterocyclic residue); C(=O)—O(aryl); C(=O)—O(heteroaryl); C(=O)—NH$_2$; C(=O)—N(H)($C_{1-8}$-aliphatic residue); C(=O)—N(H)($C_{3-6}$-cycloaliphatic residue); C(=O)—N(H)(3 to 7 membered heterocyclic residue); C(=O)—N(H)(aryl); C(=O)—N(H)(heteroaryl); C(=O)—N($C_{1-8}$-aliphatic residue)($C_{1-8}$-aliphatic residue); C(=O)—N($C_{1-8}$-aliphatic residue)($C_{3-6}$-cycloaliphatic residue); C(=O)—N($C_{1-8}$-aliphatic residue)(3 to 7 membered heterocyclic residue); C(=O)—N($C_{1-8}$-aliphatic residue)(aryl); C(=O)—N($C_{1-8}$-aliphatic residue)(heteroaryl); OH; =O; O—($C_{1-8}$-aliphatic residue); O—($C_{3-6}$-cycloaliphatic residue); O-(3 to 7 membered heterocyclic residue); O-(aryl); O-(heteroaryl); OCF$_3$; OCF$_2$H; OCFH$_2$; OCF$_2$Cl; OCFCl$_2$; O—($C_{2-4}$-aliphatic group)-OH; O—($C_{2-4}$-aliphatic group)-O($C_{1-8}$-aliphatic residue); O—C(=O)—($C_{1-8}$-aliphatic residue); O—C(=O)—($C_{3-6}$-cycloaliphatic residue); O—C(=O)-(3 to 7 membered heterocyclic residue); O—C(=O)-(aryl); C(=O)-(heteroaryl); O—C(=O)—NH$_2$; O—C(=O)—N(H)($C_{1-8}$-aliphatic residue); O—C(=O)—N(H)($C_{3-6}$-cycloaliphatic residue); O—C(=O)—N(H)(3 to 7 membered heterocyclic residue); O—C(=O)—N(H)(aryl); O—C(=O)—N(H)(heteroaryl); O—C(=O)—N($C_{1-8}$-aliphatic residue)($C_{1-8}$-aliphatic residue); O—C(=O)—N($C_{1-8}$-aliphatic residue)($C_{3-6}$-cycloaliphatic residue); O—C(=O)—N($C_{1-8}$-aliphatic residue)(3 to 7 membered heterocyclic residue); O—C(=O)—N($C_{1-8}$-aliphatic residue)(aryl); O—C(=O)—N($C_{1-8}$-aliphatic residue)(heteroaryl); NH$_2$; N(H)($C_{1-8}$-aliphatic residue); N(H)($C_{3-6}$-cycloaliphatic residue); N(H)(3 to 7 membered heterocyclic residue); N(H)(aryl); N(H)(heteroaryl); N($C_{1-8}$-aliphatic residue)($C_{1-8}$-aliphatic residue); N($C_{1-8}$-aliphatic residue)($C_{3-6}$-cycloaliphatic residue); N($C_{1-8}$-aliphatic residue)(3 to 7 membered heterocyclic residue); N($C_{1-8}$-aliphatic residue)(aryl); N($C_{1-8}$-aliphatic residue)(heteroaryl); N(H)—C(=O)—($C_{1-8}$-aliphatic residue); N(H)—C(=O)—($C_{3-6}$-cycloaliphatic residue); N(H)—C(=O)-(3 to 7 membered heterocyclic residue); N(H)—C(=O)-(aryl); N(H)—C(=O)-(heteroaryl); N($C_{1-8}$-aliphatic residue)-C(=O)—($C_{1-8}$-aliphatic residue); N($C_{1-8}$-aliphatic residue)-C(=O)—($C_{3-6}$-cycloaliphatic residue); N($C_{1-8}$-aliphatic residue)-C(=O)-(3 to 7 membered heterocyclic residue); N($C_{1-8}$-aliphatic residue)-C(=O)-(aryl); N($C_{1-8}$-aliphatic residue)-C(=O)-(heteroaryl); N(H)—S(=O)$_2$—($C_{1-8}$-aliphatic residue); N(H)—S(=O)$_2$—($C_{3-6}$-cycloaliphatic residue); N(H)—S(=O)$_2$-(3 to 7 membered heterocyclic residue); N(H)—S(=O)$_2$-(aryl); N(H)—S(=O)$_2$-(heteroaryl); N($C_{1-8}$-aliphatic residue)-S(=O)$_2$—($C_{1-8}$-aliphatic residue); N($C_{1-8}$-aliphatic residue)-S(=O)$_2$—($C_{3-6}$-cycloaliphatic residue); N($C_{1-8}$-aliphatic residue)-S(=O)$_2$-(3 to 7 membered heterocyclic residue); N($C_{1-8}$-aliphatic residue)S(=O)$_2$-(aryl); N($C_{1-8}$-aliphatic residue)-S(=O)$_2$-(heteroaryl); N(H)—C(=O)—O($C_{1-8}$-aliphatic residue); N(H)—C(=O)—O($C_{3-6}$-cycloaliphatic residue); N(H)—C(=O)—O(3 to 7 membered heterocyclic residue); N(H)—C(=O)—O(aryl); N(H)—C(=O)—O(heteroaryl); N($C_{1-8}$-aliphatic residue)-C(=O)—O($C_{1-8}$-aliphatic residue); N($C_{1-8}$-aliphatic residue)-C(=O)—O($C_{3-6}$-cycloaliphatic residue); N($C_{1-8}$-aliphatic residue)-C(=O)—O(3 to 7 membered heterocyclic residue); N($C_{1-8}$-aliphatic residue)-C(=O)—O(aryl); N($C_{1-8}$-aliphatic residue)-C(=O)—O(heteroaryl); N(H)—C(=O)—NH$_2$; N(H)—C (=O)—N(H)(C₁₋₈-aliphatic residue); N(H)—C(=O)—N(H)(C₃₋₆-cycloaliphatic residue); N(H)—C(=O)—N(H)(3 to 7 membered heterocyclic residue); N(H)—C(=O)—N(H)(aryl); N(H)—C(=O)—N(H)(heteroaryl); N(C₁₋₈-aliphatic residue)-C(=O)—NH₂; N(C₁₋₈-aliphatic residue)-C(=O)—N(H)(C₁₋₈-aliphatic residue); N(C₁₋₈-aliphatic residue)-C(=O)—N(H)(C₃₋₆-cycloaliphatic residue); N(C₁₋₈-aliphatic residue)-C(=O)—N(H)(3 to 7 membered heterocyclic residue); N(C₁₋₈-aliphatic residue)-C(=O)—N(H)(aryl); N(C₁₋₈-aliphatic residue)-C(=O)—N(H)(heteroaryl); N(H)—C(=O)—N(C₁₋₈-aliphatic residue)(C₁₋₈-aliphatic residue); N(H)—C(=O)—N(C₁₋₈-aliphatic residue)(C₃₋₆-cycloaliphatic residue); N(H)—C(=O)—N(C₁₋₈-aliphatic residue)(3 to 7 membered heterocyclic residue); N(H)—C(=O)—N(C₁₋₈-aliphatic residue)(aryl); N(H)—C(=O)—N(C₁₋₈-aliphatic residue)(heteroaryl); N(C₁₋₈-aliphatic residue)-C(=O)—N(C₁₋₈-aliphatic residue)(C₁₋₈-aliphatic residue); N(C₁₋₈-aliphatic residue)-C(=O)—N(C₁₋₈-aliphatic residue)(C₃₋₆-cycloaliphatic residue); N(C₁₋₈-aliphatic residue)-C(=O)—N(C₁₋₈-aliphatic residue)(3 to 7 membered heterocyclic residue); N(C₁₋₈-aliphatic residue)-C(=O)—N(C₁₋₈-aliphatic residue)(aryl); N(C₁₋₈-aliphatic residue)-C(=O)—N(C₁₋₈-aliphatic residue) heteroaryl); SH; S—(C₁₋₈-aliphatic residue); S—(C₃₋₆-cycloaliphatic residue); S-(3 to 7 membered heterocyclic residue); S-(aryl); S-(heteroaryl); SCF₃; S(=O)₂OH; S(=O)—(C₁₋₈-aliphatic residue); S(=O)—(C₃₋₆-cycloaliphatic residue); S(=O)-(3 to 7 membered heterocyclic residue); S(=O)-(aryl); S(=O)-(heteroaryl); S(=O)₂—(C₁₋₈-aliphatic residue); S(=O)₂—(C₃₋₆-cycloaliphatic residue); S(=O)₂-(3 to 7 membered heterocyclic residue); S(=O)₂-(aryl); S(=O)₂-(heteroaryl); S(=O)₂—O(C₁₋₈-aliphatic residue); S(=O)₂—O(C₃₋₆-cycloaliphatic residue); S(=O)₂—O(3 to 7 membered heterocyclic residue); S(=O)₂—O(aryl); S(=O)₂—O(heteroaryl); S(=O)₂—N(H)(C₁₋₈-aliphatic residue); S(=O)₂—N(H)(C₃₋₆-cycloaliphatic residue); S(=O)₂—N(H)(3 to 7 membered heterocyclic residue); S(=O)₂—N(H)(aryl); S(=O)₂—N(H)(heteroaryl); S(=O)₂—N(C₁₋₈-aliphatic residue)(C₁₋₈-aliphatic residue); S(=O)₂—N(C₁₋₈-aliphatic residue)(C₃₋₆-cycloaliphatic residue); S(=O)₂—N(C₁₋₈-aliphatic residue)(3 to 7 membered heterocyclic residue); S(=O)₂—N(C₁₋₈-aliphatic residue)(aryl); S(=O)₂—N(C₁₋₈-aliphatic residue)(heteroaryl);

optionally in the form of a single stereoisomer or a mixture of stereoisomers, in the form of the free compound and/or a physiologically acceptable salt thereof and/or a physiologically acceptable solvate thereof, with the proviso that the compound according to general formula (I) does not represent N-(2-Cyanophenyl)-5-(2-methoxy-5-methylphenyl)-1-methyl-1H-pyrazole-3-carboxamide,

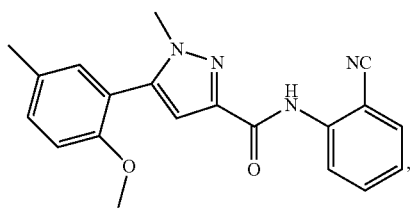

5-(2-Fluoro-4-methoxyphenyl)-N-(2-fluorophenyl)-1-methyl-1H-pyrazole-3-carboxamide,

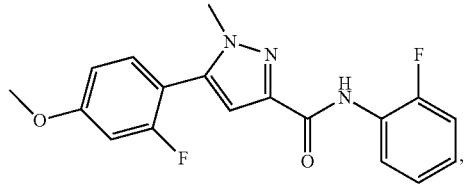 [SMILES: COc1ccc(-c2cc(C(=O)Nc3ccccc3F)nn2C)c(F)c1]

1-Ethyl-5-(2-fluoro-4-methoxyphenyl)-N-(2-fluorophenyl)-1H-pyrazole-3-carboxamide

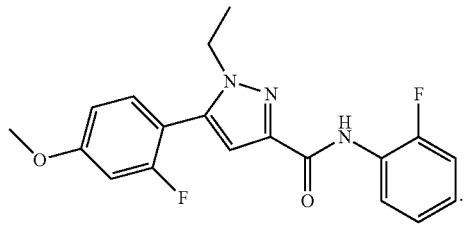 [SMILES: CCn1nc(C(=O)Nc2ccccc2F)cc1-c1ccc(OC)cc1F]

DETAILED DESCRIPTION

The term "single stereoisomer" preferably means in the sense of the present invention an individual enantiomer or diastereomer. The term "mixture of stereoisomers" means in the sense of this invention the racemate and mixtures of enantiomers and/or diastereomers in any mixing ratio.

The term "physiologically acceptable salt" preferably comprises in the sense of this invention a salt of at least one compound according to the present invention and at least one physiologically acceptable acid or base.

A physiologically acceptable salt of at least one compound according to the present invention and at least one physiologically acceptable acid preferably refers in the sense of this invention to a salt of at least one compound according to the present invention with at least one inorganic or organic acid which is physiologically acceptable—in particular when used in human beings and/or other mammals.

A physiologically acceptable salt of at least one compound according to the present invention and at least one physiologically acceptable base preferably refers in the sense of this invention to a salt of at least one compound according to the present invention as an anion with at least one preferably inorganic cation, which is physiologically acceptable—in particular when used in human beings and/or other mammals.

The term "physiologically acceptable solvate" preferably comprises in the sense of this invention an adduct of one compound according to the present invention and/or a physiologically acceptable salt of at least one compound according to the present invention with distinct molecular equivalents of one solvent or more solvents.

The terms "C₁₋₈-aliphatic residue" and "C₁₋₄-aliphatic residue" comprise in the sense of this invention acyclic saturated or unsaturated aliphatic hydrocarbon residues, which can be branched or unbranched and also unsubstituted or mono- or polysubstituted, which contain 1 to 8 or 1 to 4 carbon atoms respectively, i.e. C₁₋₈-alkanyls (C₁₋₈-alkyls), C₂₋₈-alkenyls and C₂₋₈-alkynyls as well as C₁₋₄-alkanyls (C₁₋₄-alkyls), C₂₋₄-alkenyls and C₂₋₄-alkynyls, respectively. Alkenyls comprise at least one C—C-double bond (a C=C-bond) and alkynyls comprise at least one C—C triple bond (a C≡C-bond). Preferably, -aliphatic residues are selected from the group consisting of alkanyl (alkyl) and alkenyl residues, more preferably are alkanyl (alkyl) residues. Hence, preferred "$C_{1-8}$-aliphatic residue" is "$C_{1-8}$-alkyl" and preferred "$C_{1-4}$-aliphatic residue" is "$C_{1-4}$-alkyl". Preferred $C_{1-8}$-alkyl residues are selected from the group consisting of methyl, ethyl, n-propyl, 2-propyl, n-butyl, isobutyl, sec.-butyl, tert.-butyl, n-pentyl, isopentyl, neopentyl, n-hexyl, n-heptyl and n-octyl. Preferred $C_{1-4}$-alkyl residues are selected from the group consisting of methyl, ethyl, n-propyl, 2-propyl, n-butyl, isobutyl, sec.-butyl and tert.-butyl. Preferred $C_{2-8}$-alkenyl residues are selected from the group consisting of ethenyl (vinyl), propenyl ($—CH_2CH=CH_2$, $—CH=CH—CH_3$, $—C(=CH_2)CH_3$), butenyl, pentenyl, hexenyl heptenyl and octenyl. Preferred $C_{2-4}$ alkenyl residues are selected from the group consisting of ethenyl (vinyl), propenyl ($—CH_2CH=CH_2$, $—CH=CHCH_3$, $—C(=CH_2)CH_3$) and butenyl. Preferred $C_{2-8}$ alkynyl residues are selected from the group consisting of ethynyl, propynyl ($—CH_2—C\equiv CH$, $—C\equiv C—CH_3$), butynyl, pentynyl, hexynyl, heptynyl and octynyl. Preferred $C_{2-4}$-alkynyl residues are selected from the group consisting of ethynyl, propynyl ($—CH_2—C\equiv CH$, $—C\equiv C—CH_3$) and butynyl.

The term "$C_{3-6}$-cycloaliphatic residue" means for the purposes of this invention cyclic aliphatic hydrocarbons containing 3, 4, 5 or 6 carbon atoms, wherein the hydrocarbons in each case can be saturated or unsaturated (but not aromatic), unsubstituted or mono- or polysubstituted. The-cycloaliphatic residues can be bound to the respective superordinate general structure via any desired and possible ring member of the-cycloaliphatic residue. The-cycloaliphatic residues can also be condensed with further saturated, (partially) unsaturated, (hetero)cyclic, aromatic or heteroaromatic ring systems, i.e. with cycloaliphatic, heterocycloaliphatic, aryl or heteroaryl residues, which in each case can in turn be unsubstituted or mono- or polysubstituted. Preferred $C_{3-6}$-cycloaliphatic residues are selected from the group consisting of cyclopropyl, cyclobutyl, cyclopentyl, cyclohexyl, cyclopentenyl and cyclohexenyl, in particular cyclopropyl.

The terms "3 to 7 membered heterocycloaliphatic residue" or "3-7-membered heterocycloaliphatic residue", mean for the purposes of this invention heterocycloaliphatic saturated or unsaturated (but not aromatic) residues having 3 to 6, i.e. 3, 4, 5 or 6 ring members, in which in each case at least one, if appropriate also two, three or four carbon atoms are replaced by a heteroatom or a heteroatom group each selected independently of one another from the group consisting of O, S, $S(=O)$, $S(=O)_2$, N, NH and $N(C_{1-6}$-alkyl) such as $N(CH_3)$, wherein the ring members can be unsubstituted or mono- or polysubstituted. The 3 to 7 membered heterocycloaliphatic residue residues can also be condensed with further saturated, (partially) unsaturated, (hetero)cyclic, aromatic or heteroaromatic ring systems, i.e. with cycloaliphatic, heterocycloaliphatic, aryl or heteroaryl residues, which in each case can in turn be unsubstituted or mono- or polysubstituted. The heterocycloaliphatic residue can be bound to the superordinate general structure via any desired and possible ring member of the heterocycloaliphatic residue if not indicated otherwise.

The term "aryl" means for the purpose of this invention aromatic hydrocarbons having 6 to 14, i.e. 6, 7, 8, 9, 10, 11, 12, 13 or 14 ring members, preferably having 6 to 10, i.e. 6, 7, 8, 9 or 10 ring members, including phenyls and naphthyls. Each aryl residue can be unsubstituted or mono- or polysubstituted, wherein the aryl substituents can be the same or different and in any desired and possible position of the aryl. The aryl can be bound to the superordinate general structure via any desired and possible ring member of the aryl residue. The aryl residues can also be condensed with further saturated, (partially) unsaturated, (hetero)cycloaliphatic, aromatic or heteroaromatic ring systems, i.e. with a cycloaliphatic, heterocycloaliphatic, aryl or heteroaryl residue, which can in turn be unsubstituted or mono- or polysubstituted. Examples of condensed aryl residues are benzodioxolanyl and benzodioxanyl. Preferably, aryl is selected from the group consisting of phenyl, 1-naphthyl, 2-naphthyl, fluorenyl and anthracenyl, each of which can be respectively unsubstituted or mono- or polysubstituted. A particularly preferred aryl is phenyl, unsubstituted or mono- or polysubstituted.

The term "heteroaryl" for the purpose of this invention represents a 5 or 6-membered cyclic aromatic residue containing at least 1, if appropriate also 2, 3, 4 or 5 heteroatoms, wherein the heteroatoms are each selected independently of one another from the group S, N and O and the heteroaryl residue can be unsubstituted or mono- or polysubstituted; in the case of substitution on the heteroaryl, the substituents can be the same or different and be in any desired and possible position of the heteroaryl. The binding to the superordinate general structure can be carried out via any desired and possible ring member of the heteroaryl residue if not indicated otherwise. The heteroaryl can also be part of a bi- or polycyclic system having up to 14 ring members, wherein the ring system can be formed with further saturated, (partially) unsaturated, (hetero)cycloaliphatic or aromatic or heteroaromatic rings, i.e. with a cycloaliphatic, heterocycloaliphatic, aryl or heteroaryl residue, which can in turn be unsubstituted or mono- or polysubstituted. It is preferable for the heteroaryl residue to be selected from the group consisting of benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, furyl (furanyl), imidazolyl, imidazothiazolyl, indazolyl, indolizinyl, indolyl, isoquinolinyl, isoxazoyl, isothiazolyl, indolyl, naphthyridinyl, oxazolyl, oxadiazolyl, phenazinyl, phenothiazinyl, phthalazinyl, pyrazolyl, pyridyl (2-pyridyl, 3-pyridyl, 4-pyridyl), pyrrolyl, pyridazinyl, pyrimidinyl, pyrazinyl, purinyl, phenazinyl, thienyl (thiophenyl), triazolyl, tetrazolyl, thiazolyl, thiadiazolyl and triazinyl.

The term "connected via a $C_{1-4}$-aliphatic group" with respect to residues as aryl, heteroaryl, heterocycloaliphatic residue and-cycloaliphatic residue mean for the purpose of the invention that these residues have the above-defined meanings and that each of these residues is bound to the respective superordinate general structure via a $C_{1-4}$-aliphatic group. The $C_{1-4}$-aliphatic group can in all cases be branched or unbranched, unsubstituted or mono- or polysubstituted. The $C_{1-4}$-aliphatic group can in all cases be furthermore saturated or unsaturated, i.e. can be a $C_{1-4}$-alkylene group, a $C_{2-4}$-alkenylene group or a $C_{2-4}$-alkynylene group. Preferably, the $C_{1-4}$-aliphatic group is a $C_{1-4}$-alkylene group or a $C_{2-4}$-alkenylene group, more preferably a $C_{1-4}$-alkylene group. Preferred $C_{1-4}$-alkylene groups are selected from the group consisting of $—CH_2—$, $—CH_2—CH_2—$, $—CH(CH_3)—$, $—CH_2CH_2CH_2—$, $—CH(CH_3)CH_2—$, $—CH(CH_2CH_3)—$, $—CH_2(CH_2)_2CH_2—$, $—CH(CH_3)CH_2CH_2—$, $—CH_2CH(CH_3)CH_2—$, $—CH(CH_3)CH(CH_3)—$, $—CH(CH_2CH_3)CH_2—$, $—C(CH_3)_2CH_2—$, $—CH(CH_2CH_2CH_3)—$ and $—C(CH_3)(CH_2CH_3)—$. Preferred $C_{2-4}$-alkenylene groups are selected from the group consisting of $—CH=CH—$, $—CH=CHCH_2—$, $—C(CH_3)=CH_2—$, $—CH=CHCH_2CH_2—$, $—CH_2CH=CHCH_2—$, $—CH=CH—CH=CH—$, $—C(CH_3)=CHCH_2—$, —CH=C(CH$_3$)CH$_2$—, —C(CH$_3$)=C(CH$_3$)— and —C(CH$_2$CH$_3$)=CH—. Preferred C$_{2-4}$-alkynylene groups are selected from the group consisting of —C≡C—, —C≡CCH$_2$—, —C≡C—CH$_2$—CH$_2$—, —C≡C—CH(CH$_3$)—, —CH$_2$—C≡C—CH$_2$— and —C≡C—C≡C—.

In relation to the terms "aliphatic residue" and "aliphatic group", in particular "alkyl" and "alkylene", as well as "aliphatic group", "cycloaliphatic residue" and "heterocycloaliphatic residue", the term "mono- or polysubstituted" refers in the sense of this invention, with respect to the corresponding residues or groups, to the single substitution or multiple substitution, e.g. disubstitution, trisubstitution, tetrasubstitution, or pentasubstitution, of one or more hydrogen atoms each independently of one another by at least one substituent selected from the group consisting of F; Cl; CN; CF$_3$; CF$_2$H; CFH$_2$; CF$_2$Cl; CFCl$_2$; C$_{1-8}$-aliphatic residue; C$_{3-6}$-cycloaliphatic residue; 3 to 7 membered heterocyclic residue; aryl; heteroaryl; aryl, heteroaryl, C$_{3-6}$-cycloaliphatic residue or 3 to 6 membered heterocycloaliphatic, each connected via a C$_{1-4}$-aliphatic group; C(=O)—(C$_{1-8}$-aliphatic residue); C(=O)—(C$_{3-6}$-cycloaliphatic residue); C(=O)-(3 to 7 membered heterocyclic residue); C(=O)-(aryl); C(=O)-(heteroaryl); C(=O)OH; C(=O)—O(C$_{1-8}$-aliphatic residue); C(=O)—O(C$_{3-6}$-cycloaliphatic residue); C(=O)—O(3 to 7 membered heterocyclic residue); C(=O)—O(aryl); C(=O)—O(heteroaryl); C(=O)—NH$_2$; C(=O)—N(H)(C$_{1-8}$-aliphatic residue); C(=O)—N(H)(C$_{3-6}$-cycloaliphatic residue); C(=O)—N(H)(3 to 7 membered heterocyclic residue); C(=O)—N(H)(aryl); C(=O)—N(H)-(heteroaryl); C(=O)—N(C$_{1-8}$-aliphatic residue)(C$_{1-8}$-aliphatic residue); C(=O)—N(C$_{1-8}$-aliphatic residue)(C$_{3-6}$-cycloaliphatic residue); C(=O)—N(C$_{1-8}$-aliphatic residue)(3 to 7 membered heterocyclic residue); C(=O)—N(C$_{1-8}$-aliphatic residue)(aryl); C(=O)—N(C$_{1-8}$-aliphatic residue)(heteroaryl); OH; =O; O—(C$_{1-8}$-aliphatic residue); O—(C$_{3-6}$-cycloaliphatic residue); O-(3 to 7 membered heterocyclic residue); O-(aryl); O-(heteroaryl); OCF$_3$; OCF$_2$H; OCFH$_2$; OCF$_2$Cl; OCFCl$_2$; O—C(=O)—(C$_{1-8}$-aliphatic residue); O—C(=O)—(C$_{3-6}$-cycloaliphatic residue); O—C(=O)-(3 to 7 membered heterocyclic residue); O—C(=O)-(aryl); C(=O)-(heteroaryl); O—C(=O)—NH$_2$; O—C(=O)—N(H)(C$_{1-8}$-aliphatic residue); O—C(=O)—N(H)(C$_{3-6}$-cycloaliphatic residue); O—C(=O)—N(H)(3 to 7 membered heterocyclic residue); O—C(=O)—N(H)(aryl); O—C(=O)—N(H)(heteroaryl); O—C(=O)—N(C$_{1-8}$-aliphatic residue)(C$_{1-8}$-aliphatic residue); O—C(=O)—N(C$_{1-8}$-aliphatic residue)(C$_{3-6}$-cycloaliphatic residue); O—C(=O)—N(C$_{1-8}$-aliphatic residue)(3 to 7 membered heterocyclic residue); O—C(=O)—N(C$_{1-8}$-aliphatic residue)(aryl); O—C(=O)—N(C$_{1-8}$-aliphatic residue) (heteroaryl); NH$_2$; N(H)(C$_{1-8}$-aliphatic residue); N(H)(C$_{3-6}$-cycloaliphatic residue); N(H)(3 to 7 membered heterocyclic residue); N(H)(aryl); N(H)(heteroaryl); N(C$_{1-8}$-aliphatic residue)(C$_{1-8}$-aliphatic residue); N(C$_{1-8}$-aliphatic residue)(C$_{3-6}$-cycloaliphatic residue); N(C$_{1-8}$-aliphatic residue)(3 to 7 membered heterocyclic residue); N(C$_{1-8}$-aliphatic residue)(aryl); N(C$_{1-8}$-aliphatic residue)(heteroaryl); N(H)—C(=O)—(C$_{1-8}$-aliphatic residue); N(H)—C(=O)—(C$_{3-6}$-cycloaliphatic residue); N(H)—C(=O)-(3 to 7 membered heterocyclic residue); N(H)—C(=O)-(aryl); N(H)—C(=O)-(heteroaryl); N(C$_{1-8}$-aliphatic residue)-C(=O)—(C$_{1-8}$-aliphatic residue); N(C$_{1-8}$-aliphatic residue)-C(=O)—(C$_{3-6}$-cycloaliphatic residue); N(C$_{1-8}$-aliphatic residue)-C(=O)-(3 to 7 membered heterocyclic residue); N(C$_{1-8}$-aliphatic residue)-C(=O)-(aryl); N(C$_{1-8}$-aliphatic residue)-C(=O)-(heteroaryl); N(H)—S(=O)$_2$—(C$_{1-8}$-aliphatic residue); N(H)—S(=O)$_2$—(C$_{3-6}$-cycloaliphatic residue); N(H)—S(=O)$_2$-(3 to 7 membered heterocyclic residue); N(H)—S(=O)$_2$-(aryl); N(H)—S(=O)$_2$-(heteroaryl); N(C$_{1-8}$-aliphatic residue)-S(=O)$_2$—(C$_{1-8}$-aliphatic residue); N(C$_{1-8}$-aliphatic residue)-S(=O)$_2$—(C$_{3-6}$-cycloaliphatic residue); N(C$_{1-8}$-aliphatic residue)-S(=O)$_2$-(3 to 7 membered heterocyclic residue); N(C$_{1-8}$-aliphatic residue)-S(=O)$_2$-(aryl); N(C$_{1-8}$-aliphatic residue)-S(=O)$_2$-(heteroaryl); N(H)—C(=O)—O(C$_{1-8}$-aliphatic residue); N(H)—C(=O)—O(C$_{3-6}$-cycloaliphatic residue); N(H)—C(=O)—O(3 to 7 membered heterocyclic residue); N(H)—C(=O)—O(aryl); N(H)—C(=O)—O(heteroaryl); N(C$_{1-8}$-aliphatic residue)-C(=O)—O(C$_{1-8}$-aliphatic residue); N(C$_{1-8}$-aliphatic residue)-C(=O)—O(C$_{3-6}$-cycloaliphatic residue); N(C$_{1-8}$-aliphatic residue)-C(=O)—O(3 to 7 membered heterocyclic residue); N(C$_{1-8}$-aliphatic residue)-C(=O)—O(aryl); N(C$_{1-8}$-aliphatic residue)-C(=O)—O(heteroaryl); N(H)—C(=O)—NH$_2$; N(H)—C(=O)—N(H)(C$_{1-8}$-aliphatic residue); N(H)—C(=O)—N(H)(C$_{3-6}$-cycloaliphatic residue); N(H)—C(=O)—N(H)(3 to 7 membered heterocyclic residue); N(H)—C(=O)—N(H)(aryl); N(H)—C(=O)—N(H)(heteroaryl); N(C$_{1-8}$-aliphatic residue)-C(=O)—NH$_2$; N(C$_{1-8}$-aliphatic residue)-C(=O)—N(H)(C$_{1-8}$-aliphatic residue); N(C$_{1-8}$-aliphatic residue)-C(=O)—N(H)(C$_{3-6}$-cycloaliphatic residue); N(C$_{1-8}$-aliphatic residue)-C(=O)—N(H)(3 to 7 membered heterocyclic residue); N(C$_{1-8}$-aliphatic residue)-C(=O)—N(H)(aryl); N(C$_{1-8}$-aliphatic residue)-C(=O)—N(H)(heteroaryl); N(H)—C(=O)—N(C$_{1-8}$-aliphatic residue)(C$_{1-8}$-aliphatic residue); N(H)—C(=O)—N(C$_{1-8}$-aliphatic residue)(C$_{3-6}$-cycloaliphatic residue); N(H)—C(=O)—N(C$_{1-8}$-aliphatic residue)(3 to 7 membered heterocyclic residue); N(H)—C(=O)—N(C$_{1-8}$-aliphatic residue)(aryl); N(H)—C(=O)—N(C$_{1-8}$-aliphatic residue)(heteroaryl); N(C$_{1-8}$-aliphatic residue)-C(=O)—N(C$_{1-8}$-aliphatic residue)(C$_{1-8}$-aliphatic residue); N(C$_{1-8}$-aliphatic residue)-C(=O)—N(C$_{1-8}$-aliphatic residue)(C$_{3-6}$-cycloaliphatic residue); N(C$_{1-8}$-aliphatic residue)-C(=O)—N(C$_{1-8}$-aliphatic residue)(3 to 7 membered heterocyclic residue); N(C$_{1-8}$-aliphatic residue)-C(=O)—N(C$_{1-8}$-aliphatic residue)(aryl); N(C$_{1-8}$-aliphatic residue)-C(=O)—N(C$_{1-8}$-aliphatic residue)(heteroaryl); S—(C$_{3-6}$-cycloaliphatic residue); S-(3 to 7 membered heterocyclic residue); S-(aryl); S-(heteroaryl); SCF$_3$; S(=O)$_2$OH; S(=O)—(C$_{1-8}$-aliphatic residue); S(=O)—(C$_{3-6}$-cycloaliphatic residue); S(=O)-(3 to 7 membered heterocyclic residue); S(=O)-(aryl); S(=O)-(heteroaryl); S(=O)$_2$—(C$_{1-8}$-aliphatic residue); S(=O)$_2$—(C$_{3-6}$-cycloaliphatic residue); S(=O)$_2$-(3 to 7 membered heterocyclic residue); S(=O)$_2$-(aryl); S(=O)$_2$-(heteroaryl); S(=O)$_2$—O(C$_{1-8}$-aliphatic residue); S(=O)$_2$—O(C$_{3-6}$-cycloaliphatic residue); S(=O)$_2$—O(3 to 7 membered heterocyclic residue); S(=O)$_2$—O(aryl); S(=O)$_2$—O(heteroaryl); S(=O)$_2$—N(H)(C$_{1-8}$-aliphatic residue); S(=O)$_2$—N(H)(C$_{3-6}$-cycloaliphatic residue); S(=O)$_2$—N(H)(3 to 7 membered heterocyclic residue); S(=O)$_2$—N(H)(aryl); S(=O)$_2$—N(H)(heteroaryl); S(=O)$_2$—N(C$_{1-8}$-aliphatic residue)(C$_{1-8}$-aliphatic residue); S(=O)$_2$—N(C$_{1-8}$-aliphatic residue)(C$_{3-6}$-cycloaliphatic residue); S(=O)$_2$—N(C$_{1-8}$-aliphatic residue)(3 to 7 membered heterocyclic residue); S(=O)$_2$—N(C$_{1-8}$-aliphatic residue)(aryl); S(=O)$_2$—N(C$_{1-8}$-aliphatic residue)(heteroaryl).

The term "polysubstituted" with respect to polysubstituted residues and groups includes the poly-substitution of these residues and groups either on different or on the same atoms, for example tri-substituted on the same carbon atom, as in the case of CF$_3$, CH$_2$CF$_3$ or 1,1-difluorocyclohexyl, or at various points, as in the case of CH(OH)—CH=CH—CHCl$_2$ or 1-chloro-3-fluorocyclohexyl. A substituent can if appropriate for its part in turn be mono- or polysubstituted. The multiple substitution can be carried out using the same or using different substituents.

Preferred substituents of "aliphatic residue" and "aliphatic group", in particular "alkyl" and "alkylene", as well as of "aliphatic group", "cycloaliphatic residue" and "heterocycloaliphatic residue" are selected from the group consisting of F; Cl; CN; =O; $CF_3$; $CF_2H$; $CFH_2$; $CF_2Cl$; $CFCl_2$; $C_{1-4}$-alkyl; ($C_{2-4}$-aliphatic group)-OH; C(=O)—H; C(=O)—$C_{1-4}$-alkyl; C(=O)—OH; C(=O)—O—$C_{1-4}$-alkyl; C(=O)—N(H)(OH); C(=O)—$NH_2$; C(=O)—N(H)($C_{1-4}$-alkyl); C(=O)—N($C_{1-4}$-alkyl)$_2$; OH; $OCF_3$; $OCF_2H$; $OCFH_2$; $OCF_2Cl$; $OCFCl_2$; O—$C_{1-4}$-alkyl; O—C(=O)—$C_{1-4}$-alkyl; O—C(=O)—O—$C_{1-4}$-alkyl; O—(C=O)—N(H)($C_{1-4}$-alkyl); O—C(=O)—N($C_{1-4}$-alkyl)$_2$; O—S(=O)$_2$—$C_{1-4}$-alkyl; O—S(=O)$_2$—OH; O—S(=O)$_2$—O—$C_{1-4}$-alkyl; O—S(=O)$_2$—$NH_2$; O—S(=O)$_2$—N(H)($C_{1-4}$-alkyl); O—S(=O)$_2$—N($C_{1-4}$-alkyl)$_2$; $NH_2$; N(H)($C_{1-4}$-alkyl); N($C_{1-4}$-alkyl)$_2$; N(H)—C(=O)—$C_{1-4}$-alkyl; N(H)—C(=O)—O—$C_{1-4}$-alkyl; N(H)—C(=O)—$NH_2$; N(H)—C(=O)—N(H)($C_{1-4}$-alkyl); N(H)—C(=O)—N($C_{1-4}$-alkyl)$_2$; N($C_{1-4}$-alkyl)-C(=O)—$C_{1-4}$-alkyl; N($C_{1-4}$-alkyl)-C(=O)—O—$C_{1-4}$-alkyl; N($C_{1-4}$-alkyl)-C(=O)—$NH_2$; N($C_{1-4}$-alkyl)-C(=O)—N(H)($C_{1-4}$-alkyl); N($C_{1-4}$-alkyl)-C(=O)—N($C_{1-4}$-alkyl)$_2$; N(H)—S(=O)$_2$—OH; N(H)—S(=O)$_2$—$C_{1-4}$-alkyl; N(H)—S(=O)$_2$—O—$C_{1-4}$-alkyl; N(H)—S(=O)$_2$—$NH_2$; N(H)—S(=O)$_2$—N(H)($C_{1-4}$-alkyl); N(H)—S(=O)$_2$—N($C_{1-4}$-alkyl)$_2$; N($C_{1-4}$-alkyl)-S(=O)$_2$—OH; N($C_{1-4}$-alkyl)-S(=O)$_2$—$C_{1-4}$-alkyl; N($C_{1-4}$-alkyl)-S(=O)$_2$—O—$C_{1-4}$-alkyl; N($C_{1-4}$-alkyl)-S(=O)$_2$—$NH_2$; N($C_{1-4}$-alkyl)-S(=O)$_2$—N(H)($C_{1-4}$-alkyl); N($C_{1-4}$-alkyl)-S(=O)$_2$—N($C_{1-4}$-alkyl)$_2$; SH; $SCF_3$; $SCF_2H$; $SCFH_2$; $SCF_2Cl$; $SCFCl_2$; S—$C_{1-4}$-alkyl; S(=O)—$C_{1-4}$-alkyl; S(=O)$_2$—$C_{1-4}$-alkyl; S(=O)$_2$—OH; S(=O)$_2$—O—$C_{1-4}$-alkyl; S(=O)$_2$—$NH_2$; S(=O)$_2$—N(H)($C_{1-4}$-alkyl); and S(=O)$_2$—N($C_{1-4}$-alkyl)$_2$.

Particularly preferred substituents of "aliphatic residue" and "aliphatic group", in particular "alkyl" and "alkylene", as well as of "aliphatic group", "cycloaliphatic residue" and "heterocycloaliphatic residue" are selected from the group consisting of F; Cl; $CF_3$; CN; =O; $C_{1-4}$-alkyl; ($C_{2-4}$-aliphatic group)-OH; C(=O)—H; C(=O)—$C_{1-4}$-alkyl; C(=O)—OH; C(=O)—O—$C_{1-4}$-alkyl; C(=O)—$NH_2$; C(=O)—N(H)($C_{1-4}$-alkyl); N($C_{1-4}$-alkyl)$_2$; N(H)—O(=O)—$C_{1-4}$-alkyl; N(H)—S(=O)$_2$—$C_{1-4}$-alkyl; N($C_{1-4}$-alkyl)-S(=O)$_2$—$C_{1-4}$-alkyl; N(H)—O(=O)—$NH_2$; N(H)—O(=O)—N(H)($C_{1-4}$-alkyl); N(H)—O(=O)—N($C_{1-4}$-alkyl)$_2$; N(H)—S(=O)$_2$—$NH_2$; N(H)—S(=O)$_2$—N(H)($C_{1-4}$-alkyl); N(H)—S(=O)$_2$—N($C_{1-4}$-alkyl)$_2$; N($C_{1-4}$-alkyl)-S(=O)$_2$—$NH_2$; N($C_{1-4}$-alkyl)-S(=O)$_2$—N(H)($C_{1-4}$-alkyl); N($C_{1-4}$-alkyl)-S(=O)$_2$—N($C_{1-4}$-alkyl)$_2$; SH; $SCF_3$; S—$C_{1-4}$-alkyl; S(=O)$_2$$C_{1-4}$-alkyl; S(=O)$_2$OH; S(=O)$_2$O—$C_{1-4}$-alkyl and S(=O)$_2$—$NH_2$; S(=O)$_2$—N(H)($C_{1-4}$-alkyl); and S(=O)$_2$—N($C_{1-4}$-alkyl)$_2$.

More preferred substituents of "aliphatic residue" and "aliphatic group", in particular "alkyl" and "alkylene", as well as of "aliphatic group", "cycloaliphatic residue" and "heterocycloaliphatic residue" are selected from the group consisting of F; Cl; $CF_3$; CN; =O; $C_{1-4}$-alkyl; ($C_{2-4}$-aliphatic group)-OH; C(=O)—$C_{1-4}$-alkyl; C(=O)—OH; C(=O)—O—$C_{1-4}$-alkyl; C(=O)—$NH_2$; C(=O)—N(H)($C_{1-4}$-alkyl); C(=O)—N($C_{1-4}$-alkyl)$_2$; OH; O—$C_{1-4}$-alkyl; O—C(=O)—$C_{1-4}$-alkyl; $OCF_3$; $NH_2$; N(H)($C_{1-4}$-alkyl); N($C_{1-4}$-alkyl)$_2$; N(H)—C(=O)—$C_{1-4}$-alkyl; N(H)—S(=O)$_2$—$C_{1-4}$-alkyl; N($C_{1-4}$-alkyl)-S(=O)$_2$—$C_{1-4}$-alkyl; N(H)—C(=O)—$NH_2$; N(H)—O(=O)—N(H)($C_{1-4}$-alkyl); N(H)—C(=O)—N($C_{1-4}$-alkyl)$_2$; N($C_{1-4}$-alkyl)-S(=O)$_2$—$NH_2$; N($C_{1-4}$-alkyl)-S(=O)$_2$—N(H)($C_{1-4}$-alkyl); N($C_{1-4}$-alkyl)-S(=O)$_2$—N($C_{1-4}$-alkyl)$_2$; S(=O)$_2$—$C_{1-4}$-alkyl; S(=O)$_2$OH; S(=O)$_2$O—$C_{1-4}$-alkyl; S(=O)$_2$—$NH_2$; S(=O)$_2$—N(H)($C_{1-4}$-alkyl) and S(=O)$_2$—N($C_{1-4}$-alkyl)$_2$.

Most preferred substituents of "aliphatic residue" and "aliphatic group", in particular "alkyl" and "alkylene" are selected from the group consisting of F; Cl; $CF_3$; C(=O)—OH; C(=O)—$NH_2$; C(=O)—N(H)($C_{1-4}$-alkyl); C(=O)—N($C_{1-4}$-alkyl)$_2$; OH; O—$C_{1-4}$-alkyl; $NH_2$; N(H)($C_{1-4}$-alkyl); N($C_{1-4}$-alkyl)$_2$; N(H)—O(=O)—$C_{1-4}$-alkyl; N(H)—S(=O)$_2$—$C_{1-4}$-alkyl; N($C_{1-4}$-alkyl)-S(=O)$_2$—$C_{1-4}$-alkyl; N(H)—S(=O)$_2$—$NH_2$; S(=O)$_2$—$C_{1-4}$-alkyl, S(=O)$_2$—$NH_2$, S(=O)$_2$—N($C_{1-4}$-alkyl)$_2$ and S(=O)$_2$—N(H)($C_{1-4}$-alkyl).

Particularly preferred substituents of "cycloaliphatic residue" and "heterocycloaliphatic residue" are selected from the group consisting of F; Cl; $CF_3$; CN; =O; $C_{1-4}$-alkyl; $CO_2H$; C(=O)O—$C_{1-4}$-alkyl; $CONH_2$; C(=O)NH—$C_{1-4}$-alkyl; C(=O)N($C_{1-4}$-alkyl)$_2$; OH; O—$C_{1-4}$-alkyl; $OCF_3$; O—C(=O)—$C_{1-4}$-alkyl; $NH_2$; NH—$C_{1-4}$-alkyl; N($C_{1-4}$-alkyl)$_2$; NH—C(=O)—$C_{1-4}$-alkyl; N($C_{1-4}$-alkyl)-O(=O)—$C_{1-4}$-alkyl; S(=O)$_2$—$C_{1-4}$-alkyl; S(=O)$_2$—$NH_2$, S(=O)$_2$—N($C_{1-4}$-alkyl)$_2$ and S(=O)$_2$—N(H)—$C_{1-4}$-alkyl.

In relation to the terms "aryl" and "heteroaryl", the term "mono- or polysubstituted" refers in the sense of this invention, with respect to the corresponding residues or groups, to the single substitution or multiple substitution, e.g. disubstitution, trisubstitution, tetrasubstitution, or pentasubstitution, of one or more hydrogen atoms each independently of one another by at least one substituent selected from the group consisting of F; Cl; Br; $NO_2$; CN; $CF_3$; $CF_2H$; $CFH_2$; $CF_2Cl$; $CFCl_2$; $C_{1-8}$-aliphatic residue; $C_{3-6}$-cycloaliphatic residue; 3 to 7 membered heterocyclic residue; aryl; heteroaryl; aryl, heteroaryl, $C_{3-6}$-cycloaliphatic residue or 3 to 6 membered heterocycloaliphatic, each connected via a $C_{1-4}$-aliphatic group; C(=O)H; C(=O)—($C_{1-8}$-aliphatic residue); C(=O)—($C_{3-6}$-cycloaliphatic residue); C(=O)-(3 to 7 membered heterocyclic residue); C(=O)-(aryl); C(=O)-(heteroaryl); C(=O)OH; C(=O)—O($C_{1-8}$-aliphatic residue); C(=O)—O($C_{3-6}$-cycloaliphatic residue); C(=O)—O(3 to 7 membered heterocyclic residue); C(=O)—O(aryl); C(=O)—O(heteroaryl); C(=O)—$NH_2$; C(=O)—N(H)($C_{1-8}$-aliphatic residue); C(=O)—N(H)($C_{3-6}$-cycloaliphatic residue); C(=O)—N(H)(3 to 7 membered heterocyclic residue); C(=O)—N(H)(aryl); C(=O)—N(H)(heteroaryl); C(=O)—N($C_{1-8}$-aliphatic residue)($C_{1-8}$-aliphatic residue); C(=O)—N($C_{1-8}$-aliphatic residue)($C_{3-6}$-cycloaliphatic residue); C(=O)—N($C_{1-8}$-aliphatic residue)(3 to 7 membered heterocyclic residue); C(=O)—N($C_{1-8}$-aliphatic residue)(aryl); C(=O)—N($C_{1-8}$-aliphatic residue)(heteroaryl); OH; =O; O—($C_{1-8}$-aliphatic residue); O—($C_{3-6}$-cycloaliphatic residue); O-(3 to 7 membered heterocyclic residue); O-(aryl); O-(heteroaryl); $OCF_3$; $OCF_2H$; $OCFH_2$; $OCF_2Cl$; $OCFCl_2$; O—C(=O)—($C_{1-8}$-aliphatic residue); O—C(=O)—($C_{3-6}$-cycloaliphatic residue); O—C(=O)-(3 to 7 membered heterocyclic residue); O—C(=O)-(aryl); C(=O)-(heteroaryl); O—C(=O)—$NH_2$; O—C(=O)—N(H)($C_{1-8}$-aliphatic residue); O—C(=O)—N(H)($C_{3-6}$-cycloaliphatic residue); O—C(=O)—N(H)(3 to 7 membered heterocyclic residue); O—C(=O)—N(H)(aryl); O—C(=O)—N(H)(heteroaryl); O—C(=O)—N($C_{1-8}$-aliphatic residue)($C_{1-8}$-aliphatic residue); O—C(=O)—N($C_{1-8}$-aliphatic residue)($C_{3-6}$-cycloaliphatic residue); O—C(=O)—N($C_{1-8}$-aliphatic residue)(3 to 7 membered heterocyclic residue); O—C(=O)—

N($C_{1-8}$-aliphatic residue)-(aryl); O—C(=O)—N($C_{1-8}$-aliphatic residue)(heteroaryl); $NH_2$; N(H)($C_{1-8}$-aliphatic residue); N(H)($C_{3-6}$-cycloaliphatic residue); N(H)(3 to 7 membered heterocyclic residue); N(H)(aryl); N(H)(heteroaryl); N($C_{1-8}$-aliphatic residue)($C_{1-8}$-aliphatic residue); N($C_{1-8}$-aliphatic residue)($C_{3-6}$-cycloaliphatic residue); N($C_{1-8}$-aliphatic residue)(3 to 7 membered heterocyclic residue); N($C_{1-8}$-aliphatic residue) (aryl); N($C_{1-8}$-aliphatic residue)(heteroaryl); N(H)—C(=O)—($C_{1-8}$-aliphatic residue); N(H)—C(=O)—($C_{3-6}$-cycloaliphatic residue); N(H)—C(=O)-(3 to 7 membered heterocyclic residue); N(H)—C(=O)-(aryl); N(H)—C(=O)-(heteroaryl); aliphatic residue)-C(=O)—($C_{1-8}$-aliphatic residue); N($C_{1-8}$-aliphatic residue)-C(=O)—($C_{3-6}$-cycloaliphatic residue); N($C_{1-8}$-aliphatic residue)-C(=O)-(3 to 7 membered heterocyclic residue); N($C_{1-8}$-aliphatic residue)-C(=O)-(aryl); N($C_{1-8}$-aliphatic residue)-C(=O)-(heteroaryl); N(H)—S(=O)$_2$—($C_{1-8}$-aliphatic residue); N(H)—S(=O)$_2$—($C_{3-6}$-cycloaliphatic residue); N(H)—S(=O)$_2$-(3 to 7 membered heterocyclic residue); N(H)—S(=O)$_2$-(aryl); N(H)—S(=O)$_2$-(heteroaryl); N($C_{1-8}$-aliphatic residue)-S(=O)$_2$—($C_{1-8}$-aliphatic residue); N($C_{1-8}$-aliphatic residue)-S(=O)$_2$—($C_{3-6}$-cycloaliphatic residue); N($C_{1-8}$-aliphatic residue)-S(=O)$_2$-(3 to 7 membered heterocyclic residue); N($C_{1-8}$-aliphatic residue)-S(=O)$_2$-(aryl); N($C_{1-8}$-aliphatic residue)-S(=O)$_2$-(heteroaryl); N(H)—C(=O)—O($C_{1-8}$-aliphatic residue); N(H)—C(=O)—O($C_{3-6}$-cycloaliphatic residue); N(H)—C(=O)—O(3 to 7 membered heterocyclic residue); N(H)—C(=O)—O(aryl); N(H)—C(=O)—O(heteroaryl); N($C_{1-8}$-aliphatic residue)-C(=O)—O($C_{1-8}$-aliphatic residue); N($C_{1-8}$-aliphatic residue)-C(=O)—O($C_{3-6}$-cycloaliphatic residue); N($C_{1-8}$-aliphatic residue)-C(=O)—O(3 to 7 membered heterocyclic residue); N($C_{1-8}$-aliphatic residue)-C(=O)—O(aryl); N($C_{1-8}$-aliphatic residue)-C(=O)—O(heteroaryl); N(H)—C(=O)—$NH_2$; N(H)—C(=O)—N(H)($C_{1-8}$-aliphatic residue); N(H)—C(=O)—N(H)($C_{3-6}$-cycloaliphatic residue); N(H)—C(=O)—N(H)(3 to 7 membered heterocyclic residue); N(H)—C(=O)—N(H)(aryl); N(H)—C(=O)—N(H)(heteroaryl); N($C_{1-8}$-aliphatic residue)-C(=O)—$NH_2$; N($C_{1-8}$-aliphatic residue)-C(=O)—N(H)($C_{1-8}$-aliphatic residue); N($C_{1-8}$-aliphatic residue)-C(=O)—N(H)($C_{3-6}$-cycloaliphatic residue); N($C_{1-8}$-aliphatic residue)-C(=O)—N(H)(3 to 7 membered heterocyclic residue); N($C_{1-8}$-aliphatic residue)-C(=O)—N(H)(aryl); N($C_{1-8}$-aliphatic residue)-C(=O)—N(H)(heteroaryl); N(H)—C(=O)—N($C_{1-8}$-aliphatic residue)($C_{1-8}$-aliphatic residue); N(H)—C(=O)—N($C_{1-8}$-aliphatic residue)($C_{3-6}$-cycloaliphatic residue); N(H)—C(=O)—N($C_{1-8}$-aliphatic residue)(3 to 7 membered heterocyclic residue); N(H)—C(=O)—N($C_{1-8}$-aliphatic residue)(aryl); N(H)—C(=O)—N($C_{1-8}$-aliphatic residue) (heteroaryl); N($C_{1-8}$-aliphatic residue)-C(=O)—N($C_{1-8}$-aliphatic residue)($C_{1-8}$-aliphatic residue); N($C_{1-8}$-aliphatic residue)-C(=O)—N($C_{1-8}$-aliphatic residue)($C_{3-6}$-cycloaliphatic residue); N($C_{1-8}$-aliphatic residue)-C(=O)—N($C_{1-8}$-aliphatic residue)(3 to 7 membered heterocyclic residue); N($C_{1-8}$-aliphatic residue)-C(=O)—N($C_{1-8}$-aliphatic residue)(aryl); N($C_{1-8}$-aliphatic residue)-C(=O)—N($C_{1-8}$-aliphatic residue) heteroaryl); SH; S—($C_{1-8}$-aliphatic residue); S—($C_{3-6}$-cycloaliphatic residue); S-(3 to 7 membered heterocyclic residue); S-(aryl); S-(heteroaryl); $SCF_3$; S(=O)$_2$OH; S(=O)—($C_{1-8}$-aliphatic residue); S(=O)—($C_{3-6}$-cycloaliphatic residue); S(=O)-(3 to 7 membered heterocyclic residue); S(=O)-(aryl); S(=O)-(heteroaryl); S(=O)$_2$—($C_{1-8}$-aliphatic residue); S(=O)$_2$—($C_{3-6}$-cycloaliphatic residue); S(=O)$_2$-(3 to 7 membered heterocyclic residue); S(=O)$_2$-(aryl); S(=O)$_2$-(heteroaryl); S(=O)$_2$—O($C_{1-8}$-aliphatic residue); S(=O)$_2$—O($C_{3-6}$-cycloaliphatic residue); S(=O)$_2$—O(3 to 7 membered heterocyclic residue); S(=O)$_2$—O(aryl); S(=O)$_2$—O(heteroaryl); S(=O)$_2$—N(H)($C_{1-8}$-aliphatic residue); S(=O)$_2$—N(H)($C_{3-6}$-cycloaliphatic residue); S(=O)$_2$—N(H)(3 to 7 membered heterocyclic residue); S(=O)$_2$—N(H)(aryl); S(=O)$_2$—N(H)(heteroaryl); S(=O)$_2$—N($C_{1-8}$-aliphatic residue)($C_{1-8}$-aliphatic residue); S(=O)$_2$—N($C_{1-8}$-aliphatic residue)($C_{3-6}$-cycloaliphatic residue); S(=O)$_2$—N($C_{1-8}$-aliphatic residue)(3 to 7 membered heterocyclic residue); S(=O)$_2$—N($C_{1-8}$-aliphatic residue)(aryl); S(=O)$_2$—N($C_{1-8}$-aliphatic residue)(heteroaryl).

Preferred substituents of "aryl" and "heteroaryl" are selected from the group consisting of F; Cl; Br; $NO_2$; CN; $CF_3$; $CF_2H$; $CFH_2$; $CF_2Cl$; $CFCl_2$; $C_{1-4}$-alkyl; aryl; heteroaryl; $C_{3-6}$-cycloaliphatic residue; 3 to 6 membered heterocycloaliphatic residue; aryl, heteroaryl, $C_{3-6}$-cycloaliphatic residue or 3 to 6 membered heterocycloaliphatic, each connected via a $C_{1-4}$-aliphatic group; C(=O)—H; C(=O)—$C_{1-4}$-alkyl; C(=O)aryl; C(=O)heteroaryl; C(=O)—OH; C(=O)—O—$C_{1-4}$-alkyl; C(=O)O-aryl; C(=O)O-heteroaryl; CO—$NH_2$; C(=O)—N(H)$C_{1-4}$-alkyl; C(=O)—N($C_{1-4}$-alkyl)$_2$; C(=O)NH-aryl; C(=O)N(aryl)$_2$; C(=O)NH-heteroaryl; C(=O)—N(heteroaryl)$_2$; C(=O)N($C_{1-4}$-alkyl)(aryl); C(=O)N($C_{1-4}$-alkyl)(heteroaryl); C(=O)N(heteroaryl)(aryl); OH; $OCF_3$; $OCF_2H$; $OCFH_2$; $OCF_2Cl$; $OCFCl_2$; O—$C_{1-4}$-alkyl; O-benzyl; O-aryl; O-heteroaryl; O—C(=O)—$C_{1-4}$-alkyl; O—C(=O)aryl; O—C(=O)heteroaryl; O—C(=O)—O—$C_{1-4}$-alkyl; O—(C=O)—N(H)$C_{1-4}$-alkyl; O—C(=O)—N($C_{1-4}$-alkyl)$_2$; O—S(=O)$_2$—$C_{1-4}$-alkyl; O—S(=O)$_2$—OH; O—S(=O)$_2$—O—$C_{1-4}$-alkyl; O—S(=O)$_2$—$NH_2$; O—S(=O)$_2$—N(H)$C_{1-4}$-alkyl; O—S(=O)$_2$—N($C_{1-4}$-alkyl)$_2$; $NH_2$; N(H)$C_{1-4}$-alkyl; N($C_{1-4}$-alkyl)$_2$; N(H)—C(=O)—$C_{1-4}$-alkyl; N(H)—C(=O)-aryl; N(H)—C(=O)-heteroaryl; N(H)—C(=O)—O—$C_{1-4}$-alkyl; N(H)—C(=O)—$NH_2$; N(H)—C(=O)—N(H)$C_{1-4}$-alkyl; N(H)—C(=O)—N($C_{1-4}$-alkyl)$_2$; N($C_{1-4}$-alkyl)-C(=O)$C_{1-4}$-alkyl; N($C_{1-4}$-alkyl)-C(=O)—O—$C_{1-4}$-alkyl; N($C_{1-4}$-alkyl)-C(=O)—$NH_2$; N($C_{1-4}$-alkyl)-C(=O)—N(H)$C_{1-4}$-alkyl; N($C_{1-4}$-alkyl)-C(=O)—N($C_{1-4}$-alkyl)$_2$; N(H)—S(=O)$_2$—OH; N(H)—S(=O)$_2$—$C_{1-4}$-alkyl; N(H)—S(=O)$_2$—O—$C_{1-4}$-alkyl; N(H)—S(=O)$_2$—$NH_2$; N(H)—S(=O)$_2$—N(H)$C_{1-4}$-alkyl; N(H)—S(=O)$_2$—N($C_{1-4}$-alkyl)$_2$; N($C_{1-4}$-alkyl)-S(=O)$_2$—OH; N($C_{1-4}$-alkyl)-S(=O)$_2$($C_{1-4}$-alkyl); N($C_{1-4}$-alkyl)-S(=O)$_2$—O($C_{1-4}$-alkyl); N($C_{1-4}$-alkyl)-S(=O)$_2$—$NH_2$; N($C_{1-4}$-alkyl)-S(=O)$_2$—N(H)$C_{1-4}$-alkyl; N($C_{1-4}$-alkyl)-S(=O)$_2$—N($C_{1-4}$-alkyl)$_2$; SH; $SCF_3$; $SCF_2H$; $SCFH_2$; $SCF_2Cl$; $SCFCl_2$; S—$C_{1-4}$-alkyl; S-benzyl; S-aryl; S-heteroaryl; S(=O)—$C_{1-4}$-alkyl; S(=O)$_2$—$C_{1-4}$-alkyl; S(=O)$_2$-aryl; S(=O)$_2$-heteroaryl; S(=O)$_2$—OH; S(=O)$_2$—O$C_{1-4}$-alkyl; S(=O)$_2$O-aryl; S(=O)$_2$O-heteroaryl; S(=O)$_2$—$NH_2$; S(=O)$_2$—N(H)$C_{1-4}$-alkyl, S(=O)$_2$—N(H)-aryl; S(=O)$_2$—N(H)-heteroaryl and S(=O)$_2$—N($C_{1-4}$-alkyl)$_2$.

More preferred substituents of "aryl" and "heteroaryl" are selected from the group consisting of F; Cl; $CF_3$; CN; $C_{1-4}$-alkyl; C(=O)—OH; C(=O)—O—$C_{1-4}$-alkyl; CO—$NH_2$; C(=O)—N(H)$C_{1-4}$-alkyl; C(=O)—N($C_{1-4}$-alkyl)$_2$; OH; O—$C_{1-4}$-alkyl; O—C(=O)—$C_{1-4}$-alkyl; $OCF_3$; $OCHF_2$; $OCH_2F$; $NH_2$; N(H)$C_{1-4}$-alkyl; N($C_{1-4}$-alkyl)$_2$; N(H)—C(=O)—$C_{1-4}$-alkyl; N($C_{1-4}$-alkyl)-C(=O)$C_{1-4}$-alkyl; N(H)—S(=O)$_2$—$C_{1-4}$-alkyl; N($C_{1-4}$-alkyl)-S(=O)$_2$($C_{1-4}$-alkyl); N(H)—C(=O)—$NH_2$; N(H)—C(=O)—N(H)$C_{1-4}$-alkyl; N(H)—C(=O)—N($C_{1-4}$-alkyl)$_2$; N($C_{1-4}$-alkyl)-C(=O)—$NH_2$; N($C_{1-4}$-alkyl)-C(=O)—N(H)$C_{1-4}$-alkyl; N($C_{1-4}$-alkyl)-C(=O)—N($C_{1-4}$-alkyl)$_2$; S(=O)$_2$$C_{1-4}$-alkyl; S(=O)$_2$—$NH_2$; S(=O)$_2$—N(H)$C_{1-4}$-alkyl and S(=O)$_2$—N($C_{1-4}$-alkyl)$_2$.

The compounds according to the invention are defined by substituents, for example by $R^A$, $R^B$ and $R^C$ (1$^{st}$ generation substituents) which are for their part if appropriate themselves substituted (2$^{nd}$ generation substituents). Depending on the definition, these substituents of the substituents can for their part be resubstituted (3$^{rd}$ generation substituents). If, for example, $R^A$=a $C_{1-4}$-alkyl (1$^{st}$ generation substituent), then the $C_{1-4}$-alkyl can for its part be substituted, for example with a N(H)$C_{1-4}$-alkyl (2$^{nd}$ generation substituent). This produces the functional group $R^A$=($C_{1-4}$-alkyl-N(H)—$C_{1-4}$-alkyl). The N(H)—$C_{1-4}$-alkyl can then for its part be resubstituted, for example with Cl (3$^{rd}$ generation substituent). Overall, this produces the functional group $R^A$=$C_{1-4}$-alkyl-N(H)—$C_{1-4}$-alkyl-Cl, wherein the $C_{1-4}$-alkyl of the N(H)$C_{1-4}$-alkyl is substituted by Cl.

However, in a preferred embodiment, the 3$^{rd}$ generation substituents may not be resubstituted, i.e. there are then no 4$^{th}$ generation substituents.

In another preferred embodiment, the 2$^{nd}$ generation substituents may not be resubstituted, i.e. there are then not even any 3$^{rd}$ generation substituents. In other words, in this embodiment, in the case of general formula (I), for example, the functional groups for $R^1$ to $R^3$ can each if appropriate be substituted; however, the respective substituents may then for their part not be resubstituted.

In some cases, the compounds according to the invention are defined by substituents which are or carry a-cycloaliphatic residue or a heterocycloaliphatic residue, respectively, in each case unsubstituted or mono- or polysubstituted, or which form together with the carbon atom(s) or heteroatom(s) connecting them, as the ring member or as the ring members, a ring, for example a cycloaliphatic or a heterocycloaliphatic ring system. Both these cycloaliphatic or heterocycloaliphatic ring systems and the (hetero)cycloaliphatic ring systems formed in this manner can if appropriate be condensed with a-cycloaliphatic residue, preferably a $C_{3-6}$-cycloaliphatic residue, or with a heterocycloaliphatic residue, preferably a 3 to 6 membered heterocycloaliphatic residue, e.g. with a-cycloaliphatic residue such as cyclohexyl, or a heterocycloaliphatic residue such as morpholinyl, wherein the cycloaliphatic or heterocycloaliphatic residues condensed in this way can for their part be respectively unsubstituted or mono- or polysubstituted.

Within the scope of the present invention, the symbol

used in the formulae denotes a link of a corresponding residue to the respective superordinate general structure.

If a residue occurs multiply within a molecule, then this residue can have respectively different meanings for various substituents: if, for example, both $R^A$ and $R^B$ denote a 3 to 6 membered heterocycloaliphatic residue, then the 3 to 7 membered heterocycloaliphatic residue can e.g. represent morpholinyl for $R^A$ and can represent piperazinyl for $R^B$.

In one embodiment of the compound according to the present invention, $R^2$ is selected from the group consisting of H; F; Cl; Br; I; $NO_2$; CN; $CF_3$; $CF_2H$; $CFH_2$; $R^{13}$; OH; O—$R^{13}$; $NH_2$; N(H)$R^{13}$; N($R^{13}$)$_2$, wherein $R^{13}$ independently of each other denotes $C_{1-8}$-aliphatic residue, unsubstituted or mono- or polysubstituted;

or $C_{3-6}$-cycloaliphatic residue or 3 to 7 membered heterocycloaliphatic residue, in each case unsubstituted or mono- or polysubstituted;

or $C_{3-6}$-cycloaliphatic residue or 3 to 7 membered heterocycloaliphatic residue, in each case unsubstituted or mono- or polysubstituted, and in each case connected via a $C_{1-4}$-aliphatic residue, unsubstituted or mono- or polysubstituted.

Preferably, $R^2$ is selected from the group consisting of H; F; Cl; Br; CN; $CF_3$; $CF_2H$; $CFH_2$; $R^{13}$; OH; O—$R^{13}$; $NH_2$; NH—$R^{13}$; N($R^{13}$)$_2$, wherein $R^{13}$ independently of each other denotes $C_{1-8}$-aliphatic residue, unsubstituted or mono- or polysubstituted;

or $C_{3-6}$-cycloaliphatic residue or 3 to 7 membered heterocycloaliphatic residue, in each case unsubstituted or mono- or polysubstituted;

or $C_{3-6}$-cycloaliphatic residue or 3 to 7 membered heterocycloaliphatic residue, in each case unsubstituted or mono- or polysubstituted, and in each case connected via a $C_{1-4}$-aliphatic residue, unsubstituted or mono- or polysubstituted.

More preferably, $R^2$ is selected from the group consisting of H; F; Cl; Br; CN; $CF_3$; $CF_2H$; $CFH_2$; $R^{13}$; OH; O—$R^{13}$; $NH_2$; NH—$R^{13}$; N($R^{13}$)$_2$, wherein $R^{13}$ independently of each other denotes $C_{1-4}$-aliphatic residue, unsubstituted or mono- or polysubstituted.

Still more preferably, $R^2$ is selected from the group consisting of H; F; Cl, OH, $OCH_3$, $NH_2$, N(H)$CH_3$, N($CH_3$)$_2$, $CH_2NH_2$, $CH_2$N(H)$CH_3$$CH_2$N($CH_3$)$_2$, $CH_2OH$; or unsubstituted $C_{1-4}$-aliphatic residue;

More preferably, $R^2$ is selected from the group consisting of H, F, Cl, $CH_3$; $CF_3$, $CF_2H$, $CFH_2$, $CH_2CH_3$, CN, OH, $CH_2OH$, $OCH_3$, $NH_2$ and N(H)$CH_3$.

Even more preferably, $R^2$ is selected from the group consisting of $C_1$, $NH_2$, $CH_3$, $CH_2OH$ and $CH_2CH_3$. Still more preferably, $R^2$ is selected from the group consisting of H, OH and $NH_2$. Most preferably, $R^2$ denotes H.

In another embodiment of the compound according to the present invention, $R^1$ denotes H; $C_{1-4}$-aliphatic residue, unsubstituted or mono- or polysubstituted; $C_{3-6}$-cycloaliphatic residue or 3 to 7 membered heterocycloaliphatic residue, in each case unsubstituted or mono- or polysubstituted and in each case optionally connected via a $C_{1-4}$-aliphatic group, which in turn may be unsubstituted or mono- or polysubstituted; with the proviso that if $R^1$ represents a 3 to 7 membered heterocycloaliphatic residue, said 3 to 7 membered heterocycloaliphatic residue is connected to the remaining part of the structure according to general formula (I) via a carbon atom of the 3 to 7 membered heterocycloaliphatic residue;

Preferably, $R^1$ is selected from the group consisting of unsubstituted $C_{1-4}$-aliphatic residue or unsubstituted cyclopropyl.

More preferably, is selected from the group consisting of unsubstituted $C_{1-4}$-aliphatic residue. Even more preferably, $R^1$ is selected from $CH_3$ and $CH_2CH_3$. Most preferably, $R^1$ denotes $CH_3$.

According to invention, the compound according to general formula (I) is characterized that
n represents 0 or 1,
wherein if n represents 1, then
K represents C—$R^9$ or N or $N^+$—$O^-$, M represents C—$R^{10}$ or N or $N^+$—$O^-$, Q represents C—$R^{11}$ or N or $N^+$—$O^-$, and R represents C—$R^{12}$ or N or $N^+$—$O^-$,
with the proviso that 0, 1, 2 or 3 of variables K, M, Q and R independently of one another represent(s) either N or $N^+$—$O^-$, whereof 0 or 1 of variables K, M, Q and R independently of one another represent(s) $N^+$—$O^-$,
wherein if n represents 0, then
K represents C—$R^9$ or N or $N^+$—$O^-$ or O or S or NH or N($C_{1-4}$-aliphatic residue),
M represents C—$R^{10}$ or N or $N^+$—$O^-$ or O or S or NH or N($C_{1-4}$-aliphatic residue) and
Q represents C—$R^{11}$ or N or $N^+$—$O^-$ or O or S or NH or N($C_{1-4}$-aliphatic residue), with the proviso that
one of K, M and Q represents O or S or NH or N($C_{1-4}$-aliphatic residue) and the remaining of K, M and Q independently represent C—$R^9$, respectively C—$R^{10}$, respectively C—$R^{11}$ or N or $N^+$—$O^-$ and with the proviso that 0, 1 or 2 of variables K, M and Q independently of one another represent either N or $N^+$—$O^-$, whereof 0 or 1 of variables K, M and Q represents $N^+$—$O^-$.

In another preferred embodiment of the invention, the compound according of general formula (I) is selected from the group, consisting of formulae (Ia-1)

(Ib-1)

(Ic-1)

(Id-1)

(Ie-1)
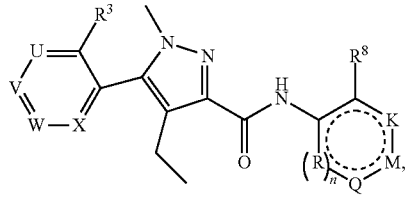

(If-1)
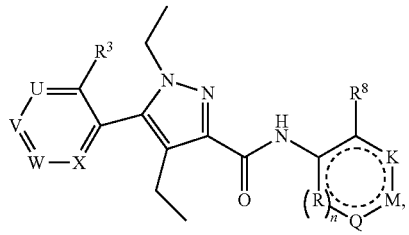

(Ig-1)
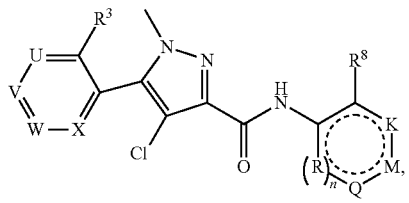

(Ih-1)
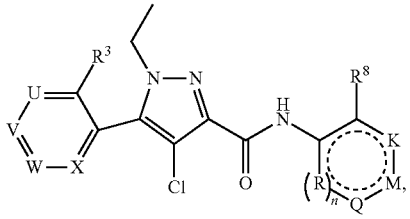

(Ii-1)
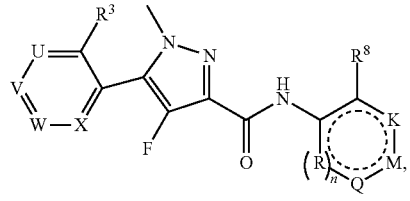

(Ij-1)
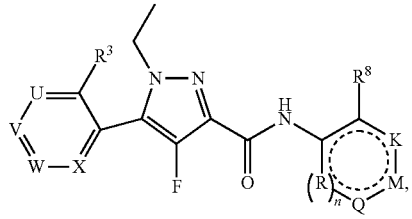

(Ik-1)
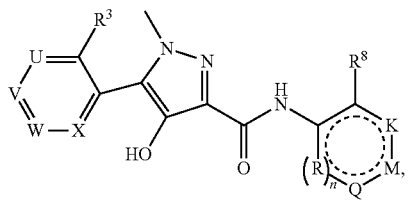

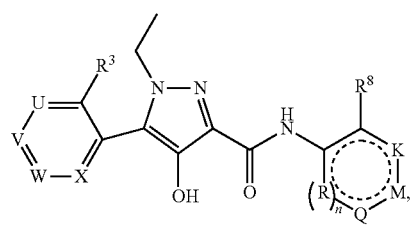

(Im-1)

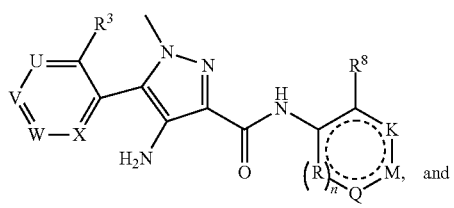

(In-1)

and

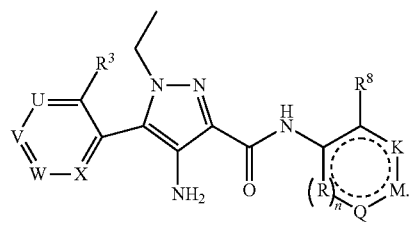

(Io-1)

In particularly preferred embodiment of the invention, the compound according of general formula (I) is selected from the group, consisting of formulae (Ia-1), (Ib-1), (Ic-1), (Id-1), (Ie-1), (If-1), (Ig-1), (Ih-1), (Ii-1), (Ij-1), (Ik-1), (Im-1), (In-1), and (Io-1), wherein each n represents 1.

More preferably, the compound according of general formula (I) is selected from the group, consisting of formulae (Ia-1), (Ic-1), (Ie-1), (Ig-1), (Ii-1), (Ik-1) and (In-1), wherein each n represents 1.

Even more preferably, the compound according of general formula (I) is selected from the group, consisting of formulae (Ia-1), (Ic-1) and (Ig-1), wherein each n represents 1.

Most preferably, the compound according of general formula (I) is selected from formula (Ia-1), wherein n represents 1.

Within the scope of the present invention, the partial structure

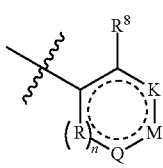

in general formula (I) represents an aryl or a heteroaryl residue. The residue is aromatic as depicted by the dashed circle line.

If n represents 1, then the partial structure in general formula (I) represents a 6 membered aryl or heteroaryl residue:

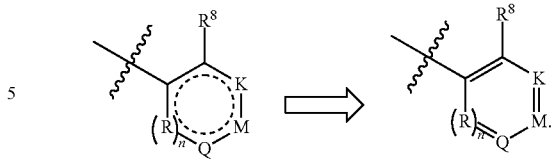

If n represents 0, then the partial structure in general formula (I) represents a 5 membered heteroaryl residue:

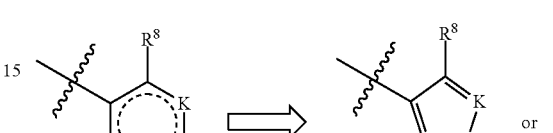 or

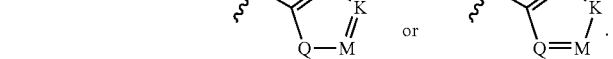

Examples for 5 membered heteroaryl residues are thienyl, thiazolyl, isothiazolyl, thiadiazolyl, furanyl, oxazolyl, isoxazolyl, oxadiazolyl, furazanyl, pyrrolyl, pyrazolyl, imidazolyl and triazolyl, in each case unsubstituted or mono- or polysubstituted.

In a preferred embodiment of the present invention, the compound according to general formula (I) is characterized in that
n represents 1, and
K represents C—$R^9$ or N or $N^+$—$O^-$, M represents C—$R^{19}$ or N or $N^+$—$O^-$, Q represents C—$R^{11}$ or N or $N^+$—$O^-$, and R represents C—$R^{12}$ or N or $N^+$—$O^-$,
  with the proviso that 0, 1, 2 or 3 of variables K, M, Q and R independently of one another represent(s) either N or $N^+$—$O^-$, whereof 0 or 1 of variables K, M, Q and R independently represents $N^+$—$O^-$.

In another preferred embodiment of the present invention, the compound according to general formula (I) is characterized in that
n represents 1, and
K represents C—$R^9$, M represents C—$R^{10}$ or N, Q represents C—$R^{11}$ and R represents C—$R^{12}$.

In another preferred embodiment of the present invention, the compound according to general formula (I) is characterized in that
n represents 1, and
K represents C—$R^9$, M represents C—$R^{10}$, Q represents C—$R^{11}$ and R represents C—$R^{12}$.

In another preferred embodiment of the present invention, the compound according to general formula (I) is characterized in that
n represents 1, and
K represents C—$R^9$, M represents N, Q represents C—$R^{11}$ and R represents C—$R^{12}$.

In another preferred embodiment of the present invention, the compound according to general formula (I) is characterized in that
n represents 1, and
K represents C—$R^9$, M represents C—$R^{10}$, Q represents N and R represents C—$R^{12}$.

In another preferred embodiment of the present invention, the compound according to general formula (I) is characterized in that n represents 1, and K represents C—$R^9$, M represents N, Q represents C—$R^{11}$ and R represents N.

Within this embodiment of the present invention, a particular substitution pattern on the cyclic substituent, incorporating J, K, M, Q and R, proved to be particular beneficial for the activity of the compounds according to the present invention.

In one preferred embodiment of the invention, the compound according of general formula (I) is characterized in that n represents 1, and R represents C—$R^{12}$, wherein $R^{12}$ is selected from the group consisting of H; $CH_3$; $CF_3$; $CF_2H$; $CFH_2$; $CF_2Cl$; $CFCl_2$; $CH_2CH_3$; $CH_2CF_3$; CN; OH; $OCH_3$; $OCHF_2$; $OCH_2F$; $OCHF_2$; $OCF_3$; $NH_2$; $NHCH_3$; $N(CH_3)_2$; $NH(C=O)CH_3$; F; Cl and Br.

Preferably, $R^8$ is selected from $CH_3$; $CF_3$; CN; $OCF_3$; F and Cl, even more preferably from the group consisting of $CF_3$; $CH_3$; CN; F and Cl, and most preferably $R^8$ denotes F.

Preferably, n represents 1, and

R represents C—$R^{12}$, wherein $R^{12}$ is selected from the group consisting of H; $CH_3$; $CF_3$; $CF_2H$; $CFH_2$; $CF_2Cl$; $CFCl_2$; $CH_2CH_3$; $CH_2CF_3$; CN; OH; $OCH_3$; $OCHF_2$; $OCH_2F$; $OCHF_2$; $OCF_3$; $NH_2$; $NHCH_3$; $N(CH_3)_2$; $NH(C=O)CH_3$; F; Cl and Br, more preferably from the group consisting of H; $CH_3$; $CF_3$; CN; OH; $OCH_3$; F; Cl and Br, and even more preferably from the group consisting of H; $CH_3$; CN; F and Cl.

In a preferred embodiment of the compound according to the present invention, n represents 1, $R^8$ denotes F, and R represents N.

In another preferred embodiment of the compound according to the present invention, n represents 1, $R^8$ denotes F, and R represents C—$R^{12}$, wherein $R^{12}$ is selected from the group consisting of H; $CH_3$; $CF_3$; CN; OH; $OCH_3$; F and Cl.

In yet another preferred embodiment of the compound according to the present invention, n represents 1, $R^8$ denotes F, and R represents C—$R^{12}$, wherein $R^{12}$ denotes H.

In yet another preferred embodiment of the compound according to the present invention, n represents 1, $R^8$ denotes F, and R represents C—$R^{12}$, wherein $R^{12}$ denotes $CH_3$.

In yet another preferred embodiment of the compound according to the present invention, n represents 1, $R^8$ denotes F, and R represents C—$R^{12}$, wherein $R^{12}$ denotes CN.

In yet another preferred embodiment of the compound according to the present invention, n represents 1, $R^8$ denotes F, and R represents C—$R^{12}$, wherein $R^{12}$ denotes F.

In yet another preferred embodiment of the compound according to the present invention, n represents 1, $R^8$ denotes F, and R represents C—$R^{12}$, wherein $R^{12}$ denotes Cl.

In one preferred embodiment of the invention, the compound according of general formula (I) is characterized in that M represents N or $N^+$—$O^-$ or C—$R^{10}$, wherein $R^{10}$ is selected from the group consisting of H; F; Cl; CN; $CF_3$; $CF_2H$; $CFH_2$; $CF_2Cl$; $CFCl_2$; $C_{1-8}$-aliphatic residue; C(=O)H; C(=O)—$NH_2$; C(=O)—$C_{1-8}$-aliphatic residue; C(=O)O—$C_{1-8}$-aliphatic residue; C(=O)NH—$C_{1-8}$-aliphatic residue; C(=O)N($C_{1-8}$-aliphatic residue)$_2$; OH; O—$C_{1-8}$-aliphatic residue; $OCF_3$; $OCF_2H$; $OCFH_2$; O—($C_{2-4}$-aliphatic group)-OH; O—($C_{2-4}$-aliphatic group)-O—$C_{1-8}$-aliphatic residue; O—C(=O)—$C_{1-8}$-aliphatic residue; $NH_2$; N(H)—$C_{1-8}$-aliphatic residue; NH—($C_{2-4}$-aliphatic group)-OH; N($C_{1-8}$-aliphatic residue)[($C_{2-4}$-aliphatic group)-OH]; N($C_{1-8}$-aliphatic residue)$_2$; N(H)—C(=O)—$C_{1-8}$-aliphatic residue; N($C_{1-8}$-aliphatic residue)-S(=O)$_2$—$C_{1-8}$-aliphatic residue; N(H)—S(=O)$_2$—$NH_2$ and S(=O)$_2$—$C_{1-8}$-aliphatic residue.

Preferably, M represents N or $N^+$—$O^-$ or C—$R^{10}$, wherein $R^{10}$ is selected from the group consisting of H; F; Cl; $OCH_3$; CN; $CH_3$; $CF_3$; $CF_2H$; $CFH_2$ and S(=O)$_2$—$CH_3$.

In another preferred embodiment of the invention, the compound according of general formula (I) is characterized in that n represents 1, R represents C—$R^{12}$, wherein $R^{12}$ is selected from the group consisting of H; $CH_3$; $CF_3$; $CF_2H$; $CFH_2$; $CH_2CH_3$; CN; OH, $OCH_3$, $OCHF_2$, $OCH_2F$; $OCHF_2$; $OCF_3$; $NH_2$; $NHCH_3$; $N(CH_3)_2$; $NH(C=O)CH_3$; F and Cl;

K represents C—$R^9$ or N and Q represents C—$R^{11}$ or N, wherein $R^9$ and $R^{11}$ are independently of one another selected from the group consisting of H; F; Cl; CN; $CF_3$; $CF_2H$; $CFH_2$; $OCF_3$; $OCF_2H$; $OCFH_2$; an unsubstituted $C_{1-4}$-aliphatic residue; OH; and an unsubstituted O—$C_{1-4}$-aliphatic residue;

and

M represents N or $N^+$—$O^-$ or C—$R^{10}$, wherein $R^{10}$ is selected from the group consisting of H; F; Cl; $OCH_3$; CN; $CH_3$; $CF_3$; $CF_2H$; $CFH_2$ and S(=O)$_2$—$CH_3$.

In another preferred embodiment of the invention, the compound according of general formula (I) is characterized in that n represents 1, R represents C—$R^{12}$, wherein $R^{12}$ is selected from the group consisting of H; $CH_3$; $CF_3$; $CF_2H$; $CFH_2$; $CH_2CH_3$; CN; OH, $OCH_3$, $OCHF_2$, $OCH_2F$; $OCHF_2$; $OCF_3$; $NH_2$; $NHCH_3$; $N(CH_3)_2$; $NH(C=O)CH_3$; F and Cl;

K represents C—$R^9$ and Q represents C—$R^{11}$, wherein $R^9$ and $R^{11}$ both denote H;

and

M represents N or $N^+$—$O^-$ or C—$R^{10}$, wherein $R^{10}$ is selected from the group consisting of H; F; Cl; $OCH_3$; CN; $CH_3$; $CF_3$; $CF_2H$; $CFH_2$ and S(=O)$_2$—$CH_3$.

In another preferred embodiment of the compound according to the present invention, n represents 1, $R^8$ denotes F, R represents C—$R^{12}$, wherein $R^{12}$ denotes H, K represents C—$R^9$ and Q represents C—$R^{11}$, wherein $R^9$ and $R^{11}$ both denote H, and M represents N.

In another preferred embodiment of the compound according to the present invention, n represents 1, $R^8$ denotes $CH_3$, R represents C—$R^{12}$, wherein $R^{12}$ denotes H, K represents C—$R^9$ and Q represents C—$R^{11}$, wherein $R^9$ and $R^{11}$ both denote H, and M represents N.

In another preferred embodiment of the compound according to the present invention, n represents 1, $R^8$ denotes F, R represents C—$R^{12}$, wherein $R^{12}$ denotes H, K represents C—$R^9$ and Q represents C—$R^{11}$, wherein $R^9$ and $R^{11}$ both denote H, and M represents C—$R^{10}$, wherein $R^{10}$ denotes H.

In another preferred embodiment of the compound according to the present invention,
$R^8$ denotes F,
R represents $C-R^{12}$, wherein $R^{12}$ denotes F,
K represents $C-R^9$ and Q represents $C-R^{11}$, wherein $R^9$ and $R^{11}$ both denote H, and
M represents N.

In another preferred embodiment of the compound according to the present invention,
n represents 1,
$R^8$ denotes F,
R represents $C-R^{12}$, wherein $R^{12}$ denotes F,
K represents $C-R^9$ and Q represents $C-R^{11}$, wherein $R^9$ and $R^{11}$ both denote H, and
M represents $C-R^{10}$, wherein $R^{10}$ denotes H.

In another preferred embodiment of the compound according to the present invention,
n represents 1,
$R^8$ denotes F,
R represents $C-R^{12}$, wherein $R^{12}$ denotes Cl,
K represents $C-R^9$ and Q represents $C-R^{11}$, wherein $R^9$ and $R^{11}$ both denote H, and
M represents $C-R^{10}$, wherein $R^{10}$ denotes H.

In another preferred embodiment of the present invention, the compound according to the present invention is characterized in that U represents $C-R^4$, V represents $C-R^5$, W represents $C-R^6$, and X represents $C-R^7$.

In another preferred embodiment of the present invention, the compound according to the present invention is characterized in that U represents $C-R^4$, V represents $C-R^5$, W represents $C-R^6$, and X represents N.

In another preferred embodiment of the present invention, the compound according to the present invention is characterized in that U represents $C-R^4$, V represents N, W represents $C-R^6$, and X represents N.

In another preferred embodiment of the present invention, the compound according to the present invention is characterized in that U represents N, V represents $C-R^5$, W represents N, and X represents $C-R^7$.

In one preferred embodiment of the present invention, the compound according to the present invention is characterized in that U represents $C-R^4$, V represents N, W represents $C-R^6$, and X represents $C-R^7$.

In one preferred embodiment of the present invention, the compound according to the present invention is characterized in that U represents N, V represents $C-R^5$, W represents $C-R^6$, and X represents $C-R^7$.

In a preferred embodiment of the present invention, the compound according to the present invention is characterized in that
n represents 1,
K represents $C-R^9$ or N or $N^+-O^-$, M represents $C-R^{10}$ or N or $N^+-O^-$, Q represents $C-R^{11}$ or N or $N^+-O^-$, and R represents $C-R^{12}$ or N or $N^+-O^-$,
with the proviso that 0, 1, 2 or 3 of variables K, M, Q and R independently of one another represent(s) either N or $N^+-O^-$, whereof 0 or 1 of variables K, M, Q and R independently represents $N^+-O^-$,
U represents $C-R^4$, V represents $C-R^5$, W represents $C-R^6$, and X represents $C-R^7$.

In a preferred embodiment of the present invention, the compound according to the present invention is characterized in that
n represents 1,
K represents $C-R^9$, M represents $C-R^{10}$, Q represents $C-R^{11}$ and R represents $C-R^{12}$,
U represents $C-R^4$, V represents $C-R^5$, W represents $C-R^6$, and X represents $C-R^7$.

In a preferred embodiment of the present invention, the compound according to the present invention is characterized in that
n represents 1,
K represents $C-R^9$, M represents N, Q represents $C-R^{11}$ and R represents $C-R^{12}$,
U represents $C-R^4$, V represents $C-R^5$, W represents $C-R^6$, and X represents $C-R^7$.

In another embodiment of the present invention, the compound according of general formula (I) is selected from the group, consisting of formulae (Ia-1), (Ic-1), (Ie-1), (Ig-1), (Ii-1), (Ik-1) and (In-1), wherein in each formula U represents $C-R^4$, V represents $C-R^5$, W represents $C-R^6$, and X represents $C-R^7$.

In another embodiment of the present invention, the compound according of general formula (I) is selected from the group, consisting of formulae (Ia-1), (Ic-1), (Ie-1), (Ig-1), (Ii-1), (Ii-2), (Ik-1) and (In-1), wherein in each formula n represents 1, U represents $C-R^4$, V represents $C-R^5$, W represents $C-R^6$, and X represents $C-R^7$.

In another preferred embodiment of the present invention, the compound according of general formula (I) is selected from the group, consisting of formulae (Ia-1), (Ic-1), (Ie-1), (Ig-1), (Ii-1), (Ik-1), and (In-1), wherein in each formula n represents 1,
K represents $C-R^9$, M represents $C-R^{10}$, Q represents $C-R^{11}$ and R represents $C-R^{12}$,
U represents $C-R^4$, V represents $C-R^5$, W represents $C-R^6$, and X represents $C-R^7$.

In another preferred embodiment of the present invention, the compound according of general formula (I) is selected from the group, consisting of formulae (Ia-1), (Ic-1), (Ie-1), (Ig-1), (Ik-1) and (In-1), wherein in each formula n represents 1,
K represents $C-R^9$, M represents N, Q represents $C-R^{11}$ and R represents $C-R^{12}$,
U represents $C-R^4$, V represents $C-R^5$, W represents $C-R^6$ and X represents $C-R^7$.

In another embodiment of the present invention, the compound according to the present invention is characterized in that
$R^4$, $R^5$ and $R^6$ independently of each other denote H; F; Cl; CN; $CF_3$; $CF_2H$; $CFH_2$; $CF_2Cl$; $CFCl_2$; $OCHF_2$; $OCFH_2$; $OCF_3$; $C_{1-8}$-aliphatic residue; $C(=O)H$; $C(=O)-NH_2$; $C(=O)-C_{1-8}$-aliphatic residue; $C(=O)O-C_{1-8}$-aliphatic residue; $C(=O)NH-C_{1-8}$-aliphatic residue; $C(=O)N(C_{1-8}$-aliphatic residue$)_2$; OH; $O-C_{1-8}$-aliphatic residue; $OCF_3$; $OCF_2H$; $OCFH_2$; $O-C(=O)-C_{1-8}$-aliphatic residue; $NH_2$; $N(H)-C_{1-8}$-aliphatic residue; $N(C_{1-8}$-aliphatic residue$)_2$; $N(H)-O(=O)-C_{1-8}$-aliphatic residue; $N(C_{1-8}$-aliphatic residue)-$S(=O)_2-C_{1-8}$-aliphatic residue; $N(H)-S(=O)_2-NH_2$ or $S(=O)_2-C_{1-8}$-aliphatic residue.

In a preferred embodiment of the compound according to the present invention, $R^4$, $R^5$ and $R^6$ independently of each other denotes H; F; Cl; $OCH_3$; $OCHF_2$; $OCFH_2$; $OCF_3$; CN; $CH_3$; $CF_3$; $CF_2H$ or $CFH_2$.

In one particular preferred embodiment of the compound according to the present invention, $R^5$ denotes H; F; Cl; $OCH_3$; $OCHF_2$; $OCFH_2$; $OCF_3$; CN; $CH_3$; $CF_3$; $CF_2H$ or $CFH_2$.

In another particular preferred embodiment of the compound according to the present invention, $R^4$ denotes H; F; Cl; $OCH_3$; $OCHF_2$; $OCFH_2$; $OCF_3$; CN; $CH_3$; $CF_3$; $CF_2H$ or $CFH_2$.

In another particular preferred embodiment of the compound according to the present invention, $R^6$ denotes H; F; Cl; $OCH_3$; $OCHF_2$; $OCFH_2$; $OCF_3$; CN; $CH_3$; $CF_3$; $CF_2H$ or $CFH_2$.

In another embodiment of the present invention, the compound according to the present invention is characterized in that $R^3$ is selected from the group consisting of F; Cl; CN; $CF_3$; $CF_2H$; $CFH_2$; $CF_2Cl$; $CFCl_2$; $OCHF_2$; $OCFH_2$; $OCF_3$; $C_{1-8}$-aliphatic residue; C(=O)H; C(=O)—$NH_2$; C(=O)—$C_{1-8}$-aliphatic residue; C(=O)O—$C_{1-8}$-aliphatic residue; C(=O)NH—$C_{1-8}$-aliphatic residue; C(=O)N($C_{1-8}$-aliphatic residue)$_2$; OH; O—$C_{1-8}$-aliphatic residue; $OCF_3$; $OCF_2H$; $OCFH_2$; O—C(=O)—$C_{1-8}$-aliphatic residue; $NH_2$; N(H)—$C_{1-8}$-aliphatic residue; N($C_{1-8}$-aliphatic residue)$_2$; N(H)—O(=O)—$C_{1-8}$-aliphatic residue; N($C_{1-8}$-aliphatic residue)-S(=O)$_2$—$C_{1-8}$-aliphatic residue; N(H)—S(=O)$_2$—$NH_2$; S(=O)$_2$—$C_{1-8}$-aliphatic residue; $C_{3-6}$-cycloaliphatic residue; 3 to 7 membered heterocycloaliphatic residue.

In preferred embodiment of the present invention, the compound according to the present invention is characterized in that $R^3$ is selected from the group consisting of F; Cl; CN; $CF_3$; $CF_2H$; $CFH_2$; $OCF_3$; $OCF_2H$; $OCFH_2$; cyclopropyl; unsubstituted $C_{1-4}$-aliphatic residue; OH and unsubstituted O—$C_{1-4}$-aliphatic residue.

In a particularly preferred embodiment of the present invention, the compound according to the present invention is characterized in that $R^3$ is selected from the group consisting of F; Cl; CN; $CF_3$; $CF_2H$; $CFH_2$; $CF_2Cl$; $CFCl_2$; $OCHF_2$; $OCFH_2$; $OCF_3$; $C_{1-8}$-aliphatic residue; C(=O)H; C(=O)—$NH_2$; C(=O)—$C_{1-8}$-aliphatic residue; C(=O)O—$C_{1-8}$-aliphatic residue; C(=O)NH—$C_{1-8}$-aliphatic residue; C(=O)N($C_{1-8}$-aliphatic residue)$_2$; OH; O—$C_{1-8}$-aliphatic residue; $OCF_3$; $OCF_2H$; $OCFH_2$; O—C(=O)—$C_{1-8}$-aliphatic residue; $NH_2$; N(H)—$C_{1-8}$-aliphatic residue; N($C_{1-8}$-aliphatic residue)$_2$; N(H)—O(=O)—$C_{1-8}$-aliphatic residue; N($C_{1-8}$-aliphatic residue)-S(=O)$_2$—$C_{1-8}$-aliphatic residue; N(H)—S(=O)$_2$—$NH_2$; S(=O)$_2$—$C_{1-8}$-aliphatic residue; $C_{3-6}$-cycloaliphatic residue; 3 to 7 membered heterocycloaliphatic residue
and
X represents C—$R^7$ and
$R^7$ represents H or F or $CH_3$ or $CF_3$.

In a particularly preferred embodiment of the present invention, the compound according to the present invention is characterized in that $R^3$ is selected from the group consisting of F; Cl; CN; $CF_3$; $CF_2H$; $CFH_2$; $OCF_3$; $OCF_2H$; $OCFH_2$; cyclopropyl; unsubstituted $C_{1-4}$-aliphatic residue; OH and unsubstituted O—$C_{1-4}$-aliphatic residue; and
X represents C—$R^7$ and
$R^7$ represents H or F or $CH_3$ or $CF_3$.

In another preferred embodiment of the present invention, the compound according to the present invention is characterized in that $R^3$ is selected from the group consisting of F; Cl; CN; $CF_3$; $CF_2H$; $CFH_2$; $CF_2Cl$; $CFCl_2$; $OCHF_2$; $OCFH_2$; $OCF_3$; $C_{1-8}$-aliphatic residue; C(=O)H; C(=O)—$NH_2$; C(=O)—$C_{1-8}$-aliphatic residue; C(=O)O—$C_{1-8}$-aliphatic residue; C(=O)NH—$C_{1-8}$-aliphatic residue; C(=O)N($C_{1-8}$-aliphatic residue)$_2$; OH; O—$C_{1-8}$-aliphatic residue; $OCF_3$; $OCF_2H$; $OCFH_2$; O—C(=O)—$C_{1-8}$-aliphatic residue; $NH_2$; N(H)—$C_{1-8}$-aliphatic residue; N($C_{1-8}$-aliphatic residue)$_2$; N(H)—O(=O)—$C_{1-8}$-aliphatic residue; N($C_{1-8}$-aliphatic residue)-S(=O)$_2$—$C_{1-8}$-aliphatic residue; N(H)—S(=O)$_2$—$NH_2$; S(=O)$_2$—$C_{1-8}$-aliphatic residue; $C_{3-6}$-cycloaliphatic residue; 3 to 7 membered heterocycloaliphatic residue
and
U represents C—$R^4$ or N, V represents C—$R^5$ or N, W represents C—$R^6$ or N, wherein
$R^4$, $R^5$ and $R^6$ are independently selected from the group consisting of H; F; Cl; CN; $CF_3$; $CF_2H$; $CFH_2$; $CF_2Cl$; $CFCl_2$; $OCHF_2$; $OCFH_2$; $OCF_3$; $C_{1-8}$-aliphatic residue; C(=O)H; C(=O)—$NH_2$; C(=O)—$C_{1-8}$-aliphatic residue; C(=O)O—$C_{1-8}$-aliphatic residue; C(=O)NH—$C_{1-8}$-aliphatic residue; C(=O)N($C_{1-8}$-aliphatic residue)$_2$; OH; O—$C_{1-8}$-aliphatic residue; $OCF_3$; $OCF_2H$; $OCFH_2$; O—C(=O)—$C_{1-8}$-aliphatic residue; $NH_2$; N(H)—$C_{1-8}$-aliphatic residue; N($C_{1-8}$-aliphatic residue)$_2$; N(H)—O(=O)—$C_{1-8}$-aliphatic residue; N($C_{1-8}$-aliphatic residue)-S(=O)$_2$—$C_{1-8}$-aliphatic residue; N(H)—S(=O)$_2$—$NH_2$; S(=O)$_2$—$C_{1-8}$-aliphatic residue
and
X represents C—$R^7$, wherein
$R^7$ represents H or F or $CH_3$ or $CF_3$.

In another preferred embodiment of the present invention, the compound according to the present invention is characterized in that $R^3$ is selected from the group consisting of F; Cl; CN; $CF_3$; $CF_2H$; $CFH_2$; $CF_2Cl$; $CFCl_2$; $OCHF_2$; $OCFH_2$; $OCF_3$; $C_{1-8}$-aliphatic residue; C(=O)H; C(=O)—$NH_2$; C(=O)—$C_{1-8}$-aliphatic residue; C(=O)O—$C_{1-8}$-aliphatic residue; C(=O)NH—$C_{1-8}$-aliphatic residue; C(=O)N($C_{1-8}$-aliphatic residue)$_2$; OH; O—$C_{1-8}$-aliphatic residue; $OCF_3$; $OCF_2H$; $OCFH_2$; O—C(=O)—$C_{1-8}$-aliphatic residue; $NH_2$; N(H)—$C_{1-8}$-aliphatic residue; N($C_{1-8}$-aliphatic residue)$_2$; N(H)—C(=O)—$C_{1-8}$-aliphatic residue; N($C_{1-8}$-aliphatic residue)-S(=O)$_2$—$C_{1-8}$-aliphatic residue; N(H)—S(=O)$_2$—$NH_2$; S(=O)$_2$—$C_{1-8}$-aliphatic residue; $C_{3-6}$-cycloaliphatic residue; 3 to 7 membered heterocycloaliphatic residue
and
V represents C—$R^5$, wherein
$R^5$ is selected from the group consisting of H; F; Cl; CN; $CF_3$; $CF_2H$; $CFH_2$; $CF_2Cl$; $CFCl_2$; $OCHF_2$; $OCFH_2$; $OCF_3$; $C_{1-8}$-aliphatic residue; C(=O)H; C(=O)—$NH_2$; C(=O)—$C_{1-8}$-aliphatic residue; C(=O)O—$C_{1-8}$-aliphatic residue; C(=O)NH—$C_{1-8}$-aliphatic residue; C(=O)N($C_{1-8}$-aliphatic residue)$_2$; OH; O—$C_{1-8}$-aliphatic residue; $OCF_3$; $OCF_2H$; $OCFH_2$; O—C(=O)—$C_{1-8}$-aliphatic residue; $NH_2$; N(H)—$C_{1-8}$-aliphatic residue; N($C_{1-8}$-aliphatic residue)$_2$; N(H)—O(=O)—$C_{1-8}$-aliphatic residue; N($C_{1-8}$-aliphatic residue)-S(=O)$_2$—$C_{1-8}$-aliphatic residue; N(H)—S(=O)$_2$—$NH_2$; S(=O)$_2$—$C_{1-8}$-aliphatic residue
and
X represents C—$R^7$, wherein
$R^7$ represents H or F or $CH_3$ or $CF_3$.

In another preferred embodiment of the present invention, the compound according to the present invention is characterized in that $R^3$ is selected from the group consisting of F; Cl; CN; $CF_3$; $CF_2H$; $CFH_2$; $CF_2Cl$; $CFCl_2$; $OCHF_2$; $OCFH_2$; $OCF_3$; $C_{1-8}$-aliphatic residue; C(=O)H; C(=O)—$NH_2$; C(=O)—$C_{1-8}$-aliphatic residue; C(=O)O—$C_{1-8}$-aliphatic residue; C(=O)NH—$C_{1-8}$-aliphatic residue; C(=O)N($C_{1-8}$-aliphatic residue)$_2$; OH; O—$C_{1-8}$-aliphatic residue; $OCF_3$; $OCF_2H$; $OCFH_2$; O—C(=O)—$C_{1-8}$-aliphatic residue; $NH_2$; N(H)—$C_{1-8}$-aliphatic residue; N($C_{1-8}$-aliphatic residue)$_2$; N(H)—C(=O)—$C_{1-8}$-aliphatic residue; N($C_{1-8}$-aliphatic residue)-S(=O)$_2$—$C_{1-8}$-aliphatic residue; N(H)—S(=O)$_2$—$NH_2$; S(=O)$_2$—$C_{1-8}$-aliphatic residue; $C_{3-6}$-cycloaliphatic residue; 3 to 7 membered heterocycloaliphatic residue
and V represents C—$R^5$, wherein
$R^5$ is selected from the group consisting of H; F; Cl; CN; $CF_3$; $CF_2H$; $CFH_2$; $CF_2Cl$; $CFCl_2$; $OCHF_2$; $OCFH_2$; $OCF_3$; $C_{1-8}$-aliphatic residue; C(=O)H; C(=O)—$NH_2$; C(=O)—$C_{1-8}$-aliphatic residue; C(=O)O—$C_{1-8}$-aliphatic residue; C(=O)NH—$C_{1-8}$-aliphatic residue; C(=O)N($C_{1-8}$-aliphatic residue)$_2$; OH; O—$C_{1-8}$-aliphatic residue; $OCF_3$; $OCF_2H$; $OCFH_2$; O—C(=O)—$C_{1-8}$-aliphatic residue; $NH_2$; N(H)—$C_{1-8}$-aliphatic residue; N($C_{1-8}$-aliphatic residue)$_2$; N(H)—O(=O)—$C_{1-8}$-aliphatic residue; N($C_{1-8}$-aliphatic residue)-S(=O)$_2$—$C_{1-8}$-aliphatic residue; N(H)—S(=O)$_2$—$NH_2$; S(=O)$_2$—$C_{1-8}$-aliphatic residue
and
U represents C—$R^4$, W represents C—$R^6$ and X represents C—$R^7$, wherein
each of $R^4$, $R^6$ and $R^7$ represents H.

In another particularly preferred embodiment of the present invention, the compound according to the present invention is characterized in that
$R^3$ is selected from the group consisting of F; Cl; CN; $CF_3$; $CF_2H$; $CFH_2$; $OCF_3$; $OCF_2H$; $OCFH_2$; cyclopropyl; unsubstituted $C_{1-4}$-aliphatic residue; OH and unsubstituted O—$C_{1-4}$-aliphatic residue and
V represents C—$R^5$, wherein $R^5$ is selected from the group consisting of H; F; Cl; $OCH_3$; $OCHF_2$; $OCFH_2$; $OCF_3$; CN; $CH_3$; $CF_3$; $CF_2H$ or $CFH_2$,
and
U represents C—$R^4$, W represents C—$R^6$ and X represents C—$R^7$, wherein each of $R^4$, $R^6$ and $R^7$ represents H.

In another preferred embodiment of the present invention, the compound according to the present invention is characterized in that
$R^3$ is selected from the group consisting of F; Cl; CN; $CF_3$; $CF_2H$; $CFH_2$; $CF_2Cl$; $CFCl_2$; $OCHF_2$; $OCFH_2$; $OCF_3$; $C_{1-8}$-aliphatic residue; C(=O)H; C(=O)—$NH_2$; C(=O)—$C_{1-8}$-aliphatic residue; C(=O)O—$C_{1-8}$-aliphatic residue; C(=O)NH—$C_{1-8}$-aliphatic residue; C(=O)N($C_{1-8}$-aliphatic residue)$_2$; OH; O—$C_{1-8}$-aliphatic residue; $OCF_3$; $OCF_2H$; $OCFH_2$; O—C(=O)—$C_{1-8}$-aliphatic residue; $NH_2$; N(H)—$C_{1-8}$-aliphatic residue; N($C_{1-8}$-aliphatic residue)$_2$; N(H)—O(=O)—$C_{1-8}$-aliphatic residue; N($C_{1-8}$-aliphatic residue)-S(=O)$_2$—$C_{1-8}$-aliphatic residue; N(H)—S(=O)$_2$—$NH_2$; S(=O)$_2$—$C_{1-8}$-aliphatic residue; $C_{3-6}$-cycloaliphatic residue; 3 to 7 membered heterocycloaliphatic residue
and
W represents C—$R^6$, wherein
$R^6$ is selected from the group consisting of
H; F; Cl; CN; $CF_3$; $CF_2H$; $CFH_2$; $CF_2Cl$; $CFCl_2$; $OCHF_2$; $OCFH_2$; $OCF_3$; $C_{1-8}$-aliphatic residue; C(=O)H; C(=O)—$NH_2$; C(=O)—$C_{1-8}$-aliphatic residue; C(=O)O—$C_{1-8}$-aliphatic residue; C(=O)NH—$C_{1-8}$-aliphatic residue; C(=O)N($C_{1-8}$-aliphatic residue)$_2$; OH; O—$C_{1-8}$-aliphatic residue; $OCF_3$; $OCF_2H$; $OCFH_2$; O—C(=O)—$C_{1-8}$-aliphatic residue; $NH_2$; N(H)—$C_{1-8}$-aliphatic residue; N($C_{1-8}$-aliphatic residue)$_2$; N(H)—O(=O)—$C_{1-8}$-aliphatic residue; N($C_{1-8}$-aliphatic residue)-S(=O)$_2$—$C_{1-8}$-aliphatic residue; N(H)—S(=O)$_2$—$NH_2$; S(=O)$_2$—$C_{1-8}$-aliphatic residue
and
X represents C—$R^7$, wherein
$R^7$ represents H.

In another preferred embodiment of the present invention, the compound according to the present invention is characterized in that
$R^3$ is selected from the group consisting of F; Cl; CN; $CF_3$; $CF_2H$; $CFH_2$; $CF_2Cl$; $CFCl_2$; $OCHF_2$; $OCFH_2$; $OCF_3$; $C_{1-8}$-aliphatic residue; C(=O)H; C(=O)—$NH_2$; C(=O)—$C_{1-8}$-aliphatic residue; C(=O)O—$C_{1-8}$-aliphatic residue; C(=O)NH—$C_{1-8}$-aliphatic residue; C(=O)N($C_{1-8}$-aliphatic residue)$_2$; OH; O—$C_{1-8}$-aliphatic residue; $OCF_3$; $OCF_2H$; $OCFH_2$; O—C(=O)—$C_{1-8}$-aliphatic residue; $NH_2$; N(H)—$C_{1-8}$-aliphatic residue; N($C_{1-8}$-aliphatic residue)$_2$; N(H)—C(=O)—$C_{1-8}$-aliphatic residue; N($C_{1-8}$-aliphatic residue)-S(=O)$_2$—$C_{1-8}$-aliphatic residue; N(H)—S(=O)$_2$—$NH_2$; S(=O)$_2$—$C_{1-8}$-aliphatic residue; $C_{3-6}$-cycloaliphatic residue; 3 to 7 membered heterocycloaliphatic residue
and
W represents C—$R^6$, wherein
$R^6$ is selected from the group consisting of H; F; Cl; CN; $CF_3$; $CF_2H$; $CFH_2$; $CF_2Cl$; $CFCl_2$; $OCHF_2$; $OCFH_2$; $OCF_3$; $C_{1-8}$-aliphatic residue; C(=O)H; C(=O)—$NH_2$; C(=O)—$C_{1-8}$-aliphatic residue; C(=O)O—$C_{1-8}$-aliphatic residue; C(=O)NH—$C_{1-8}$-aliphatic residue; C(=O)N($C_{1-8}$-aliphatic residue)$_2$; OH; O—$C_{1-8}$-aliphatic residue; $OCF_3$; $OCF_2H$; $OCFH_2$; O—C(=O)—$C_{1-8}$-aliphatic residue; $NH_2$; N(H)—$C_{1-8}$-aliphatic residue; N($C_{1-8}$-aliphatic residue)$_2$; N(H)—C(=O)—$C_{1-8}$-aliphatic residue; N($C_{1-8}$-aliphatic residue)-S(=O)$_2$—$C_{1-8}$-aliphatic residue; N(H)—S(=O)$_2$—$NH_2$; S(=O)$_2$—$C_{1-8}$-aliphatic residue
and
U represents C—$R^4$, V represents C—$R^5$ and X represents C—$R^7$, wherein
each of $R^4$, $R^5$ and $R^7$ represents H.

In another preferred embodiment of the present invention, the compound according to the present invention is characterized in that
$R^3$ is cyclopropyl
and
W represents C—$R^6$, wherein
$R^6$ is selected from the group consisting of H; F; Cl; CN; $CF_3$; $CF_2H$; $CFH_2$; $CF_2Cl$; $CFCl_2$; $OCHF_2$; $OCFH_2$; $OCF_3$; $C_{1-8}$-aliphatic residue; C(=O)H; C(=O)—$NH_2$; C(=O)—$C_{1-8}$-aliphatic residue; C(=O)O—$C_{1-8}$-aliphatic residue; C(=O)NH—$C_{1-8}$-aliphatic residue; C(=O)N($C_{1-8}$-aliphatic residue)$_2$; OH; O—$C_{1-8}$-aliphatic residue; $OCF_3$; $OCF_2H$; $OCFH_2$; O—C(=O)—$C_{1-8}$-aliphatic residue; $NH_2$; N(H)—$C_{1-8}$-aliphatic residue; N($C_{1-8}$-aliphatic residue)$_2$; N(H)—C(=O)—$C_{1-8}$-aliphatic residue; N($C_{1-8}$-aliphatic residue)-S(=O)$_2$—$C_{1-8}$-aliphatic residue; N(H)—S(=O)$_2$—$NH_2$; S(=O)$_2$—$C_{1-8}$-aliphatic residue
and
U represents C—$R^4$, V represents C—$R^5$ and X represents C—$R^7$, wherein
each of $R^4$, $R^5$ and $R^7$ represents H.

In another particularly preferred embodiment of the present invention, the compound according to the present invention is characterized in that
$R^3$ is selected from the group consisting of F; Cl; CN; $CF_3$; $CF_2H$; $CFH_2$; $OCF_3$; $OCF_2H$; $OCFH_2$; cyclopropyl; unsubstituted $C_{1-4}$-aliphatic residue; OH and unsubstituted O—$C_{1-4}$-aliphatic residue and
W represents C—$R^6$, wherein $R^6$ is selected from the group consisting of O—$C_{1-8}$-aliphatic residue; $OCF_3$; $OCF_2H$; $OCFH_2$;
and
U represents C—$R^4$, W represents C—$R^6$ and X represents C—$R^7$, wherein each of $R^4$, $R^6$ and $R^7$ represents H.

In another particularly preferred embodiment of the present invention, the compound according to the present invention is characterized in that
$R^3$ is cyclopropyl and
W represents C—$R^6$, wherein $R^6$ is selected from the group consisting of O—$C_{1-8}$-aliphatic residue; $OCF_3$; $OCF_2H$; $OCFH_2$;
and
U represents C—$R^4$, W represents C—$R^6$ and X represents C—$R^7$, wherein each of $R^4$, $R^6$ and $R^7$ represents H.

In a particular preferred embodiment of the present invention, the compound according to the present invention is characterized in that R¹ denotes an unsubstituted $C_{1-4}$-aliphatic residue, preferably denotes $CH_3$ or $CH_2CH_3$; more preferably $CH_3$;

R² denotes H; F; Cl; OH, $OCH_3$, $NH_2$, $NHCH_3$, $N(CH_3)_2$, $CH_2NH_2$, $CH_2N(H)CH_3CH_2N(CH_3)_2$, $CH_2OH$ or unsubstituted $C_{1-4}$-aliphatic residue; preferably denotes H, Cl, $NH_2$, $CH_3$, $CH_2OH$ and $CH_2CH_3$; more preferably H;

U represents C—R⁴ or N, V represents C—R⁵ or N, W represents C—R⁶ or N, and X represents C—R⁷, with the proviso that 0, 1, 2 or 3 of variables U, V, W and X independently of one another represent(s) N,
and with the proviso that at least one of U, V and W does not represent N, R³ denotes F; Cl; CN; $CF_3$; $CF_2H$; $CFH_2$; $OCF_3$; $OCF_2H$; $OCFH_2$; cyclopropyl; unsubstituted $C_{1-4}$-aliphatic residue; OH or unsubstituted O—$C_{1-4}$-aliphatic residue;

R⁷ denotes H, F, $CH_3$ or $CF_3$; and

R⁴, R⁵ and R⁶ are independently selected from the group consisting of H; F; Cl; CN; $CF_3$; $CF_2H$; $CFH_2$; $CF_2Cl$; $CFCl_2$; $OCHF_2$; $OCFH_2$; $OCF_3$; $C_{1-8}$-aliphatic residue; C(=O)H; C(=O)—$NH_2$; C(=O)—$C_{1-8}$-aliphatic residue; C(=O)O—$C_{1-8}$-aliphatic residue; C(=O)NH—$C_{1-8}$-aliphatic residue; C(=O)N($C_{1-8}$-aliphatic residue)₂; OH; O—$C_{1-8}$-aliphatic residue; $OCF_3$; $OCF_2H$; $OCFH_2$; O—C(=O)—$C_{1-8}$-aliphatic residue; $NH_2$; N(H)—$C_{1-8}$-aliphatic residue; N($C_{1-8}$-aliphatic residue)₂; N(H)—C(=O)—$C_{1-8}$-aliphatic residue; N($C_{1-8}$-aliphatic residue)-S(=O)₂—$C_{1-8}$-aliphatic residue; N(H)—S(=O)₂—$NH_2$; S(=O)₂—$C_{1-8}$-aliphatic residue;

n represents 1,

R⁸ is selected from the group consisting of F, Cl, $CF_3$, $CF_2H$, $CFH_2$, $CH_3$, CN, $OCH_3$, $OCF_2H$, $OCFH_2$, and $OCF_3$;

K represents C—R⁹ and Q represents C—R¹¹,
wherein R⁹ and R¹¹ are independently of one another selected from the group consisting of H; F; Cl; CN; $CF_3$; $CF_2H$; $CFH_2$; $OCF_3$; $OCF_2H$; $OCFH_2$; $CH_3$; OH; and $OCH_3$; and M represents N or N⁺—O⁻ or C—R¹⁰,
wherein R¹⁰ is selected from the group consisting of H; F; Cl; $OCH_3$; CN; $CH_3$; $CF_3$; $CF_2H$; $CFH_2$ or S(=O)₂—$CH_3$, R represents C—R¹²,
wherein R¹² is selected from the group consisting of H; $CH_3$; $CF_3$; $CF_2H$; $CFH_2$; $CH_2CH_3$; CN; OH; $OCH_3$; $OCHF_2$; $OCH_2F$; $OCHF_2$; $OCF_3$; F and Cl;
optionally in the form of a single stereoisomer or a mixture of stereoisomers, in the form of the free compound and/or a physiologically acceptable salt and/or a physiologically acceptable solvate thereof.

In a particular preferred embodiment of the present invention, the compound according to the present invention is characterized in that the compound has general formula (Ia),

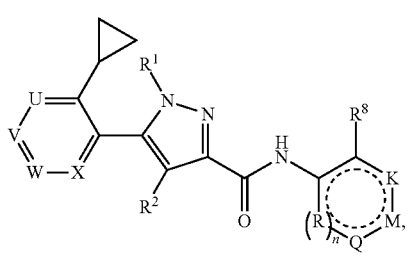

(Ia)

wherein
R¹, R², K, M, Q, R, n, U, V, W and X are defined as before and R⁸ denotes F, Cl, CN, $CF_3$, $CF_2H$, $CFH_2$, $CH_3$ or $OCH_3$.

In a particular preferred embodiment of the present invention, the compound according to the present invention is characterized in that the compound has general formula (Iaa),

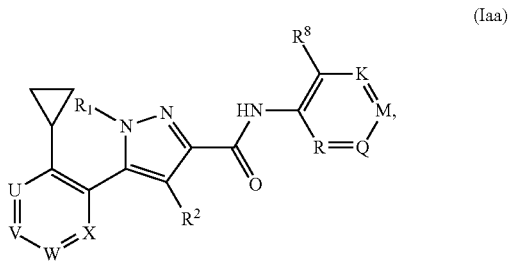

(Iaa)

wherein
R¹, R², U, V, W and X are defined as before,
R⁸ denotes F, Cl, CN, $CF_3$, $CF_2H$, $CFH_2$, $CH_3$ or O—$CH_3$
and
K, M, Q and R independently represent N, CH or C—R⁸ᵃ,
wherein R⁸ᵃ denotes F, Cl, CN, $CF_3$, $CF_2H$, $CFH_2$, $CH_3$, $CH_2CH_3$, O—$CH_3$ or O—$CH_2CH_3$, with the proviso, that 0 or 1 of the substituents K, M, Q and R represent N.

In a particular preferred embodiment of the present invention, the compound according to the present invention is selected from the group, consisting of 1   N-(2,6-Difluoro-phenyl)-5-(2-methoxyphenyl)-1-methyl-1H-pyrazole-3-carboxylic acid amide;
2   N-(2,4-Difluoro-phenyl)-5-(2,5-dimethoxyphenyl)-1-methyl-1H-pyrazole-3-carboxylic acid amide;
3   5-(2-Ethoxy-5-methoxy-phenyl)-N-(3-fluoro-pyridin-4-yl)-1-methyl-1H-pyrazole-3-carboxylic acid amide;
4   N-(2,6-Difluoro-phenyl)-5-(2-ethoxy-5-methoxy-phenyl)-1-methyl-1H-pyrazole-3-carboxylic acid amide;
5-(2,5-Difluoro-phenyl)-N-(2,6-difluoro-phenyl)-1-methyl-1H-pyrazole-3-carboxylic acid amide;
6   N-(2,6-Difluoro-phenyl)-5-[2-fluoro-5-(trifluoromethyl)-phenyl]-1-methyl-1H-pyrazole-3-carboxylic acid amide;
7   N-(2,6-Difluoro-phenyl)-1-methyl-5-[2-(trifluoromethyl)-phenyl]-1H-pyrazole-3-carboxylic acid amide;
8   N-(2,6-Difluoro-phenyl)-5-[5-methoxy-2-(trifluoromethyloxy)-phenyl]-1-methyl-1H-pyrazole-3-carboxylic acid amide;
9   N-(3-Fluoro-pyridin-4-yl)-5-[5-methoxy-2-(trifluoromethyloxy)-phenyl]-1-methyl-1H-pyrazole-3-carboxylic acid amide;
10   N-(2,6-Difluoro-phenyl)-5-(5-fluoro-2-methoxy-phenyl)-1-methyl-1H-pyrazole-3-carboxylic acid amide;
11   5-[2-Chloro-4-(trifluoromethyloxy)-phenyl]-N-(3-fluoro-pyridin-4-yl)-1-methyl-1H-pyrazole-3-carboxylic acid amide;
12   5-[2-Chloro-4-(trifluoromethyloxy)-phenyl]-N-(2,6-difluoro-phenyl)-1-methyl-1H-pyrazole-3-carboxylic acid amide;
13   5-(2,5-Dimethoxyphenyl)-N-(2-fluoro-4-methylsulfonyl-phenyl)-1-methyl-1H-pyrazole-3-carboxylic acid amide;
14   5-(2,5-Dimethoxyphenyl)-1-methyl-N-[3-(trifluoromethyl)-pyridin-4-yl]-1H-pyrazole-3-carboxylic acid amide;
15   N-(3-Cyano-pyridin-4-yl)-5-(2,5-dimethoxyphenyl)-1-methyl-1H-pyrazole-3-carboxylic acid amide;
16   5-(2,5-Dimethoxyphenyl)-1-methyl-N-(4-methyl-pyridin-3-yl)-1H-pyrazole-3-carboxylic acid amide;
17   5-(2,5-Dimethoxyphenyl)-N-(4,6-dimethyl-pyridin-3-yl)-1-methyl-1H-pyrazole-3-carboxylic acid amide;

18  5-(2,5-Di methoxyphenyl)-1-methyl-N-(5-methyl-pyrimidin-4-yl)-1H-pyrazole-3-carboxylic acid amide;
19  5-(2,5-Dimethoxyphenyl)-N-(3-fluoro-pyridin-4-yl)-1-methyl-1H-pyrazole-3-carboxylic acid amide;
20  5-(2,5-Dimethoxyphenyl)-1-methyl-N-(3-methyl-pyridin-4-yl)-1H-pyrazole-3-carboxylic acid amide;
21  N-(2,6-Difluoro-phenyl)-5-(2,5-dimethoxyphenyl)-1-methyl-1H-pyrazole-3-carboxylic acid amide;
22  5-(5-Chloro-2-methoxy-phenyl)-N-(3-fluoro-pyridin-4-yl)-1-methyl-1H-pyrazole-3-carboxylic acid amide;
23  5-(5-Chloro-2-methyl-phenyl)-N-(3-fluoro-pyridin-4-yl)-1-methyl-1H-pyrazole-3-carboxylic acid amide;
24  N-(3-Fluoro-pyridin-4-yl)-5-(4-methoxy-2-methyl-phenyl)-1-methyl-1H-pyrazole-3-carboxylic acid amide;
25  5-(2,5-Dimethoxyphenyl)-N-(3-fluoro-pyridin-4-yl)-1,4-dimethyl-1H-pyrazole-3-carboxylic acid amide;
26  5-(5-Chloro-2-methyl-phenyl)-N-(2,6-difluoro-phenyl)-1-methyl-1H-pyrazole-3-carboxylic acid amide;
27  5-(2,5-Dimethoxyphenyl)-1-methyl-N-(o-tolyl)-1H-pyrazole-3-carboxylic acid amide;
28  5-(5-Chloro-2-methyl-phenyl)-1-methyl-N-(3-methyl-pyridin-4-yl)-1H-pyrazole-3-carboxylic acid amide;
29  N-(3-Fluoro-pyridin-4-yl)-1-methyl-5-[2-methyl-5-(trifluoromethyl)-phenyl]-1H-pyrazole-3-carboxylic acid amide;
30  N-(2,6-Difluoro-phenyl)-1-methyl-5-[2-methyl-5-(trifluoromethyl)-phenyl]-1H-pyrazole-3-carboxylic acid amide;
31  N-(2,6-Difluoro-4-methoxy-phenyl)-5-(2,5-dimethoxyphenyl)-1-methyl-1H-pyrazole-3-carboxylic acid amide;
32  5-(2,5-Dimethoxyphenyl)-N-(2-fluoro-6-methyl-phenyl)-1-methyl-1H-pyrazole-3-carboxylic acid amide;
33  5-(2,5-Dimethoxyphenyl)-N-(2-fluorophenyl)-1-methyl-1H-pyrazole-3-carboxylic acid amide;
34  N-(3,5-Difluoro-pyridin-4-yl)-5-(2,5-dimethoxyphenyl)-1-methyl-1H-pyrazole-3-carboxylic acid amide;
35  N-(2-Chloro-6-fluoro-phenyl)-5-(2,5-dimethoxyphenyl)-1-methyl-1H-pyrazole-3-carboxylic acid amide;
36  5-[2-Chloro-5-(trifluoromethyl)-phenyl]-N-(2,6-difluoro-phenyl)-1-methyl-1H-pyrazole-3-carboxylic acid amide;
37  N-(2,6-Difluoro-phenyl)-5-(2,5-dimethoxyphenyl)-1-ethyl-1H-pyrazole-3-carboxylic acid amide;
38  5-[2-Cyano-5-(trifluoromethyl)-phenyl]-N-(2,6-difluoro-phenyl)-1-methyl-1H-pyrazole-3-carboxylic acid amide;
39  4-Chloro-N-(2,6-difluoro-phenyl)-5-(2,5-dimethoxyphenyl)-1-methyl-1H-pyrazole-3-carboxylic acid amide;
40  4-Chloro-5-(2,5-dimethoxyphenyl)-N-(3-fluoro-pyridin-4-yl)-1-methyl-1H-pyrazole-3-carboxylic acid amide;
41  N-(2,6-Difluoro-phenyl)-5-(2,5-dimethoxyphenyl)-1H-pyrazole-3-carboxylic acid amide;
42  N-(2,6-Difluoro-phenyl)-5-(2,5-dimethoxyphenyl)-4-ethyl-1-methyl-1H-pyrazole-3-carboxylic acid amide;
43  N-(2,6-Difluoro-phenyl)-5-(2,5-dimethoxyphenyl)-4-(hydroxymethyl)-1-methyl-1H-pyrazole-3-carboxylic acid amide;
44  4-Amino-N-(2,6-difluoro-phenyl)-5-(2,5-dimethoxyphenyl)-1-methyl-1H-pyrazole-3-carboxylic acid amide;
45  5-[2-Cyclopropyl-5-(trifluoromethyloxy)-phenyl]-N-(2,6-difluoro-phenyl)-1-methyl-1H-pyrazole-3-carboxylic acid amide;
46  5-[2-Cyclopropyl-5-(trifluoromethyloxy)-phenyl]-N-(3,5-difluoro-pyridin-4-yl)-1-methyl-1H-pyrazole-3-carboxylic acid amide;
47  5-[2-Cyclopropyl-5-(trifluoromethyloxy)-phenyl]-N-(3-fluoro-pyridin-4-yl)-1-methyl-1H-pyrazole-3-carboxylic acid amide;
48  4-Amino-5-(2,5-di methoxyphenyl)-N-(3-fluoro-pyridin-4-yl)-1-methyl-1H-pyrazole-3-carboxylic acid amide;
49  N-(3,5-Difluoro-pyridin-4-yl)-5-[2-fluoro-6-(trifluoromethyl)-phenyl]-1-methyl-1H-pyrazole-3-carboxylic acid amide;
50  N,5-Bis(2,6-difluoro-phenyl)-1-methyl-1H-pyrazole-3-carboxylic acid amide;
51  N-(2,6-Difluoro-phenyl)-5-[2-fluoro-6-(trifluoromethyl)-phenyl]-1-methyl-1H-pyrazole-3-carboxylic acid amide;
52  N-(2-Chloro-6-methyl-phenyl)-5-(2,6-difluoro-phenyl)-1-methyl-1H-pyrazole-3-carboxylic acid amide;
53  5-(2,6-Difluoro-phenyl)-N-(3-fluoro-5-methyl-pyridin-4-yl)-1-methyl-1H-pyrazole-3-carboxylic acid amide;
54  5-[2-Fluoro-6-(trifluoromethyl)-phenyl]-1-methyl-N-[2-(trifluoromethyloxy)-phenyl]-1H-pyrazole-3-carboxylic acid amide;
55  N-(2,4-Difluoro-phenyl)-5-[2-fluoro-6-(trifluoromethyl)-phenyl]-1-methyl-1H-pyrazole-3-carboxylic acid amide;
56  N-(2-Cyano-phenyl)-5-[2-fluoro-6-(trifluoromethyl)-phenyl]-1-methyl-1H-pyrazole-3-carboxylic acid amide;
57  N-(2,4-Dichlorophenyl)-5-[2-fluoro-6-(trifluoromethyl)-phenyl]-1-methyl-1H-pyrazole-3-carboxylic acid amide;
58  N-(2,6-Difluoro-4-methoxy-phenyl)-5-[2-fluoro-6-(trifluoromethyl)-phenyl]-1-methyl-1H-pyrazole-3-carboxylic acid amide;
59  N-(2-Fluoro-6-methyl-phenyl)-5-[2-fluoro-6-(trifluoromethyl)-phenyl]-1-methyl-1H-pyrazole-3-carboxylic acid amide;
60  5-[2-Fluoro-6-(trifluoromethyl)-phenyl]-1-methyl-N-[2-(trifluoromethyl)-phenyl]-1H-pyrazole-3-carboxylic acid amide;
61  N-(2-Fluorophenyl)-5-[2-fluoro-6-(trifluoromethyl)-phenyl]-1-methyl-1H-pyrazole-3-carboxylic acid amide;
62  N-(3-Fluoro-pyridin-4-yl)-5-[2-fluoro-6-(trifluoromethyl)-phenyl]-1-methyl-1H-pyrazole-3-carboxylic acid amide;
63  N-(3-Fluoro-5-methyl-pyridin-4-yl)-5-[2-fluoro-6-(trifluoromethyl)-phenyl]-1-methyl-1H-pyrazole-3-carboxylic acid amide;
64  1-Methyl-5-(4-methyl-pyridin-3-yl)-N-[2-(trifluoromethyl)-phenyl]-1H-pyrazole-3-carboxylic acid amide;
65  N-(3-Fluoro-5-methyl-pyridin-4-yl)-1-methyl-5-(4-methyl-pyridin-3-yl)-1H-pyrazole-3-carboxylic acid amide;
66  N-(2,6-Difluoro-phenyl)-5-(2-methoxy-4-methylsulfonyl-phenyl)-1-methyl-1H-pyrazole-3-carboxylic acid amide;
67  N-(3,5-Difluoro-pyridin-4-yl)-5-(2,5-dimethoxyphenyl)-1-methyl-4-methylamino-1H-pyrazole-3-carboxylic acid amide;

optionally in the form of the free compound and/or a physiologically acceptable salt thereof and/or a physiologically acceptable solvate thereof.

The compounds according to the present invention are useful for calcium release-activated calcium (CRAC) channel regulation, preferably for use in CRAC channel inhibition.

The substances according to the invention hence act, for example, on the CRAC channel relevant in connection with various diseases, so that they are suitable as a pharmacologically active compound in pharmaceutical compositions.

The compounds according to the first aspect of the present invention and the corresponding stereoisomers and the respective salts and solvates are toxicologically safe and are therefore suitable as pharmacologically active ingredients in pharmaceutical compositions.

In another aspect of the present invention, the invention therefore also provides pharmaceutical compositions, containing at least one compound according to the invention and optionally one or more suitable, pharmaceutically compatible auxiliaries and/or, if appropriate, one or more further pharmacologically active compounds.

The pharmaceutical composition according to the invention is suitable for administration to adults and children, including toddlers and babies.

The pharmaceutical composition according to the invention may be found as a liquid, semisolid or solid pharmaceutical form, for example in the form of injection solutions, drops, juices, syrups, sprays, suspensions, tablets, patches, capsules, plasters, suppositories, ointments, creams, lotions, gels, emulsions, aerosols or in multiparticulate form, for example in the form of pellets or granules, if appropriate pressed into tablets, decanted in capsules or suspended in a liquid, and also be administered as much.

In addition to at least one compound according to the invention, if appropriate in the form of one of its pure stereoisomers, in particular enantiomers or diastereomers, its racemate or in the form of mixtures of the stereoisomers, in particular the enantiomers or diastereomers, in any desired mixing ratio, or if appropriate in the form of a corresponding salt or respectively in the form of a corresponding solvate, the pharmaceutical composition according to the invention conventionally contains further physiologically compatible pharmaceutical auxiliaries which can for example be selected from the group consisting of excipients, fillers, solvents, diluents, surface-active substances, dyes, preservatives, blasting agents, slip additives, lubricants, aromas and binders. Likewise the compound according to the invention, if appropriate in the form of one of its pure stereoisomers, or if appropriate in the form of a corresponding salt or respectively in the form of a corresponding solvate, may also incorporated into the pharmaceutical composition in the form of a prodrug, which releases the active pharmacological agent through normal metabolic processes.

The selection of the physiologically compatible auxiliaries and also the amounts thereof to be used depend on whether the pharmaceutical composition is to be applied orally, subcutaneously, parenterally, intravenously, intraperitoneally, intradermally, intramuscularly, intranasally, buccally, rectally or locally, for example to infections of the skin, the mucous membranes and of the eyes. Preparations in the form of tablets, dragées, capsules, granules, pellets, drops, juices and syrups are preferably suitable for oral application; solutions, suspensions, easily reconstitutable dry preparations and also sprays are preferably suitable for parenteral, topical and inhalative application. The compounds according to the invention used in the pharmaceutical composition according to the invention in a repository in dissolved form or in a plaster, agents promoting skin penetration being added if appropriate, are suitable percutaneous application preparations. Orally or percutaneously applicable preparation forms can release the respective compound according to the invention also in a delayed manner.

The pharmaceutical compositions according to the invention are prepared with the aid of conventional means, devices, methods and process known in the art, such as are described for example in "Remington's Pharmaceutical Sciences", A. R. Gennaro (Editor), $17^{th}$ edition, Mack Publishing Company, Easton, Pa., 1985, in particular in Part 8, Chapters 76 to 93. The corresponding description is introduced herewith by way of reference and forms part of the disclosure. The amount to be administered to the patient of the respective substituted compounds according to the invention of the above-indicated general formula I may vary and is for example dependent on the patient's weight or age and also on the type of application, the indication and the severity of the disorder. Conventionally 0.001 to 100 mg/kg, preferably 0.05 to 75 mg/kg, particularly preferably 0.05 to 50 mg of at least one such compound according to the invention are applied per kg of the patient's body weight.

CRAC channels are believed to be involved in a variety of diseases or disorders in mammals such as humans. These include inflammatory disorders, allergic disorders and disorders of the immune system as well as disorders involving platelet or thrombotic activity.

Examples of allergic disorders include: rhinitis (such as allergic rhinitis), sinusitis, rhinosinusitis, chronic or recurrent otitis media, drug reactions, insect sting reactions, latex allergy, conjunctivitis, urticaria, anaphylaxis and anaphylactoid reactions, atopic dermatitis and food allergies.

Examples of inflammatory disorders include: inflammatory lung disorders (such as asthma, acute respiratory distress syndrome, acute lung injury, chronic obstructive pulmonary disease, bronchiectasis and cystic fibrosis); chronic inflammatory disorders of joints (such as arthritis, rheumatoid arthritis, osteoarthritis and bone diseases associated with increased bone resorption); inflammatory bowel diseases (such as Barrett's oesophagus, ileitis, ulcerative colitis and Crohn's disease); inflammatory disorders of the eye (such as corneal dystrophy, trachoma, uveitis, sympathetic ophthalmitis and endophthalmitis); inflammatory diseases of the kidney (such as glomerulonephritis, nephrosis, nephritic syndrome and IgA nephropathy); inflammatory diseases of the liver; inflammatory disorders of the skin (such as psoriasis and eczema); inflammatory diseases of the central nervous system (such as chronic demyelinating diseases of the nervous system, multiple sclerosis, AIDS-related neurodegeneration and Alzheimers disease, infectious meningitis, enceophalomyelitis, Parkinson's disease, Huntington's disease, amyotrophic lateral sclerosis and viral or autoimmune encephalitis); inflammatory diseases of the muscle (such as polymyositis and polymyalgia rheumatica); inflammatory diseases of the heart (such as myocarditis and cardiomyopathy, ischemic heart disease, myocardial infarction and atherosclerosis); other diseases with significant inflammatory components, including tuberculosis; leprosy; allogeneic or xenogeneic transplantation (cells, stem cells, tissues or organs) graft rejection, graft-versus-host disease; pre-eclampsia; endometriosis, chronic liver failure; brain and spinal cord trauma and cancer; and conditions where systemic inflammation of the body may also be present (such as septic shock, hemorrhagic or anaphylactic shock or shock induced by cancer chemotherapy).

Examples of disorders of the immune system include: autoimmune diseases of the central and peripheral nervous system (such as multiple sclerosis, myasthenia gravis, Eaton-Lambert Myasthenic syndrome); autoimmune neurophathies (such as Guillain-Barré); autoimmune diseases of the eye (such as autoimmune uveitis); autoimmune diseases of the blood (such as autoimmune haemolytic anemia, pernicious anemia, and autoimmune thrombocytopenia e.g. Idiopathic Thrombocytopaenic Purpura); autoimmune diseases of the vasculature (such as temporal arteritis, anti-phospholipid syndrome, vasculitides e.g. Wegener's granulomatosis and Behcet's disease); autoimmune diseases of the skin (such as alopecia areata, psoriasis, dermatitis herpetiformis, pemphigus vulgaris, bullous pemphigoid and vitiligo); autoimmune disease of the gastrointestinal tract (such as coeliac disease, Crohn's disease, ulcerative colitis, primary biliary cirrhosis and autoimmune hepatitis); autoimmune disorders of the endocrine glands (such as Type 1 diabetes mellitus, autoimmune thyroiditis, Grave's disease, Hashimoto's thyroiditis, autoimmune oophoritis and orchitis); autoimmune disorder of the adrenal gland (such as Addisons disease); autoimmune disorders of the exocrine glands (such as Sjogren's syndrome); and multi system autoimmune diseases including connective tissue and musculoskeletal system diseases (such as rheumatoid arthritis, systemic lupus erythematosus, scleroderma, polymyositis, dermatomyositis), spondyloarthropathies (such as ankylosing spondylitis and psoriatic arthritis).

Examples of conditions where anti-platelet or anti-thrombotic activity is useful for treatment and/or prophylaxis include: ischemic heart disease, myocardial infarction, cerebrovascular accident (stroke) and vascular thrombosis (venous, arterial and intra-cardiac).

Further diseases or conditions which may be treated by the compounds of the invention include conditions where mast cells and basophils contribute to pathology, such as mast cell leukaemia, mastocytosis, endometriosis and basophil leukaemia.

The term "disorders and/or diseases which are mediated, at least in part, by CRAC channels", is intended to include each of or all of the above disease states.

It is believed that the compounds of formula (I), having ICRAC inhibitory activity, may inhibit mast cell degranulation and/or inhibit T cell activation. Compounds having such activity may be particularly suitable for the treatment of a number of diseases and conditions, for example asthma; allergies such as allergic rhinitis; and nasal polyposis.

Due to the key role of calcium in the regulation of cellular proliferation in general, calcium channel inhibitors could act as cytostatic agents which may be useful in the treatment of diseases of abnormal cellular proliferation, e.g. benign prostatic hyperplasia or familial adenomatosis polyposis. The compounds may be useful for the treatment of a variety of cancers as hematopoietic tumors of lymphoid lineage (such as leukemia, acute lymphocytic leukemia, acute lymphoblastic leukemia, B-cell lymphoma, T-cell lymphoma and Hodgkin's lymphoma); hematopoietic tumors of myeloid lineage (such as acute and chronic myelgenous leukemias); carcinomas, tumors of mesenchymal origin; tumors of the central and peripheral nervous system (such as astrocytoma and neuroblastoma) and other tumors such as melanoma and sarcoma.

Another aspect of the present invention therefore relates to a compound according to the first aspect of the present invention for the treatment and/or prophylaxis of a or more disorder and/or disease, selected from the group consisting of glomerulonephritis, uveitis, hepatic diseases or disorders, especially hepatitis, renal diseases or disorders, chronic obstructive pulmonary disease (COPD), rheumatoid arthritis (RA), multiple sclerosis, inflammatory bowel disease (IBD), especially Barrett's oesophagus, ileitis, ulcerative colitis or Crohn's Disease, vasculitis, dermatitis, dermatomyositis, atopic dermatitis, scleroderma, osteoarthritis, inflammatory muscle disease, allergic rhinitis, vaginitis, interstitial cystitis, osteoporosis, eczema, psoriasis, allogeneic or xenogeneic transplantation (cells, stem cells, tissues or organs) graft rejection, graft-versus-host disease, lupus erythematosus, type I diabetes, pulmonary fibrosis, thyroiditis, myasthenia gravis, autoimmune hemolytic anemia, cystic fibrosis, chronic relapsing hepatitis, hepatitis, primary biliary cirrhosis, allergic conjunctivitis, asthma, nasal polyposis; Sjogren's syndrome, cancer and other proliferative diseases, and autoimmune diseases or disorders.

Another embodiment of this aspect of the present invention relates to a compound according to the first aspect of the present invention for the treatment and/or prophylaxis of autoimmune diseases, in particular rheumatoid arthritis and psoriatic arthritis.

Another embodiment of this aspect of the present invention relates to a compound according to the first aspect of the present invention for the treatment and/or prophylaxis of inflammatory disorders of the skin, in particular psoriasis as and/or eczema, most preferably psoriasis.

Another embodiment of this aspect of the present invention relates to a compound according to the first aspect of the present invention for the treatment and/or prophylaxis of chronic inflammatory disorders of the joints, in particular arthritis, rheumatoid arthritis and/or osteoarthritis arthritis, most preferably rheumatoid arthritis (RA).

Yet another embodiment of this aspect of the present invention relates to a compound according to the first aspect of the present invention for the treatment and/or prophylaxis of inflammatory bowel diseases, in particular Barrett's oesophagus, ileitis, ulcerative colitis and Crohn's disease.

Yet another embodiment of this aspect of the present invention relates to a compound according to the first aspect of the present invention for the treatment and/or prophylaxis of allogeneic or xenogeneic transplantation graft rejection, in particular transplantation grafts of cells, stem cells, tissues and/or organs.

Yet another embodiment of this aspect of the present invention relates to a compound according to the first aspect of the present invention for the treatment and/or prophylaxis of autoimmune diseases of the central and peripheral nervous system, in particular multiple sclerosis, myasthenia gravis and/or Eaton-Lambert Myasthenic syndrome, most preferably multiple sclerosis.

Yet another embodiment of this aspect of the present invention relates to a compound according to the first aspect of the present invention for the treatment and/or prophylaxis of inflammatory lung disorders, in particular asthma, acute respiratory distress syndrome, acute lung injury, chronic obstructive pulmonary disease, bronchiectasis and/or cystic fibrosis, most preferably asthma.

Yet another embodiment of this aspect of the present invention relates to a compound according to the first aspect of the present invention for the treatment and/or prophylaxis of allergies, in particular allergic rhinitis.

Another aspect of the present invention provides the use of at least one compound according to the present invention for the preparation of a pharmaceutical composition for the treatment and/or prophylaxis of one or more of the above mentioned diseases and/or disorders.

One embodiment of the invention provides the use of at least one compound according to the present invention for the preparation of a pharmaceutical composition for the treatment and/or prophylaxis of one or more of the diseases and/or disorders, selected from the group consisting of inflammatory disorders and/or autoimmune diseases and/or allergic disorders, preferably selected from the group consisting of psoriasis and/or psoriatic arthritis; rheumatoid arthritis; inflammatory bowel disease; asthma and allergic rhinitis.

Another aspect of the present invention is a method for the treatment and/or prophylaxis, in particular for of one or more of the above mentioned diseases and/or disorders,
in a mammal, in particular in a human, in need of treatment and/or prophylaxis of the respective disease and/or disorder, which comprises the administration of an effective amount of at least one compound according the present invention or the administration of a pharmaceutical composition according to the invention to the mammal.

One embodiment of the invention is a method for the treatment and/or prophylaxis of disorders and/or diseases, selected from the group consisting of inflammatory disorders and/or autoimmune diseases and/or allergic disorders, preferably selected from the group consisting of psoriasis and/or psoriatic arthritis; rheumatoid arthritis; inflammatory bowel disease; asthma and allergic rhinitis, in a mammal, in particular in a human, in need of treatment and/or prophylaxis of the respective disease and/or disorder, which comprises the administration of an effective amount of at least one compound according the present invention or the administration of a pharmaceutical composition according to the invention to the mammal.

The term "effective amount" according to the present invention means that administered amount of the compound or the pharmaceutical composition that will result in a therapeutically desired biological or medical response of a tissue, system, mammal or human.

A therapeutically desired biological or medical response is understood to be an improved treatment, healing, prevention, or amelioration of a disease, disorder, or side effect, or a decrease in the rate of advancement of a disease or disorder in a mammal, as compared to a corresponding mammal who has not been administered such amount. The term "therapeutically desired biological or medical response" includes also the enhancement of a normal physiological function.

The term "compounds according to the first aspect of the present invention" in foregoing aspects of the invention encompasses all possible stereoisomers and tautomers as well as the respective corresponding acids, bases, salts and solvates.

The embodiments and in particular the preferred embodiments of any aspect of the present invention apply to all other aspects of the inventions respectively.

Compounds of the invention may be made by the methods depicted in the reaction schemes below and described for examples of the invention. The following reaction schemes are illustrative only and various modifications of the methods may be made by those skilled in the art in order to obtain compounds of the invention.

Scheme 1:

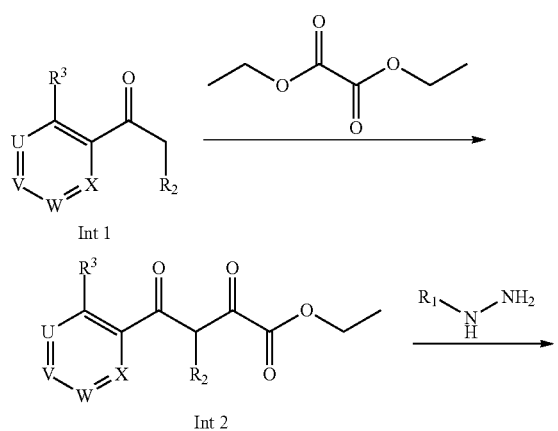

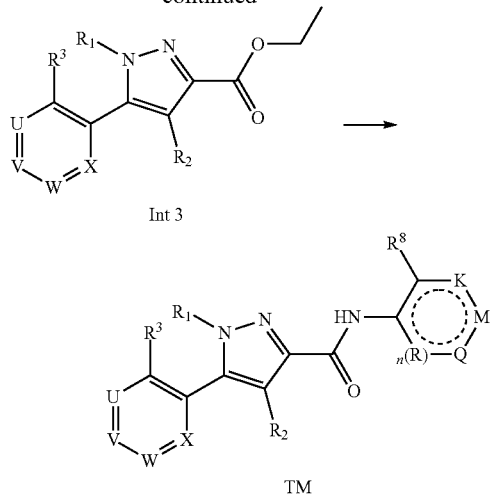

Condensation of an appropriate aryl alkyl ketone with a glyoxalate diester as diethyl glyoxalate yields a β-ketone intermediate that readily cyclises upon treatment with a suitably substituted hydrazine to afford the aryl pyrazole ethyl ester as a mixture of isomers. After separation of the isomers, for instance by flash chromatography, transformation of the ester into compounds of the invention can be performed via saponification and amide coupling by one of the various methods known to those skilled in the art or a conventional one step method (Scheme 1). Alternatively, as shown in Scheme 1a cyclisation of the β-ketone intermediate can be performed with unsubstituted hydrazine. Alkylation with suitable halogenides or equivalents again leads to substituted aryl pyrazole ethyl ester derivatives. Separation of isomers and subsequent steps follow the route depicted in Scheme 1.

Scheme 1a:

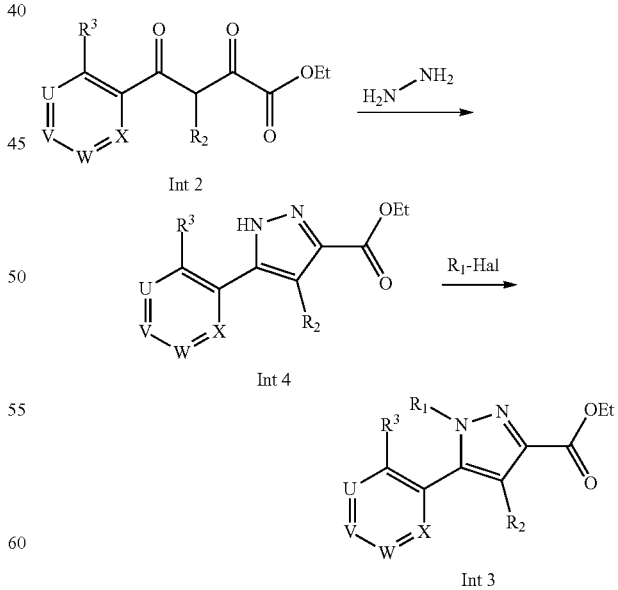

Substitutions $R_2 \neq H$ may be introduced on stage of the ketone starting material (as shown in Scheme 1, e.g. $R_2=CH_3$), the β-ketone intermediate or the aryl pyrazole ester (e.g. $R_2=C_1$, $NO_2$ as shown in Scheme 1b) or at any other suitable stage of the synthesis optionally followed by further modifications (e.g. reduction of $NO_2$ to $NH_2$ with an appropriate reagent on this or later stage). Subsequent steps may then follow the route depicted in Scheme 1. In particular cases a protecting group may be employed.

Scheme 1b:

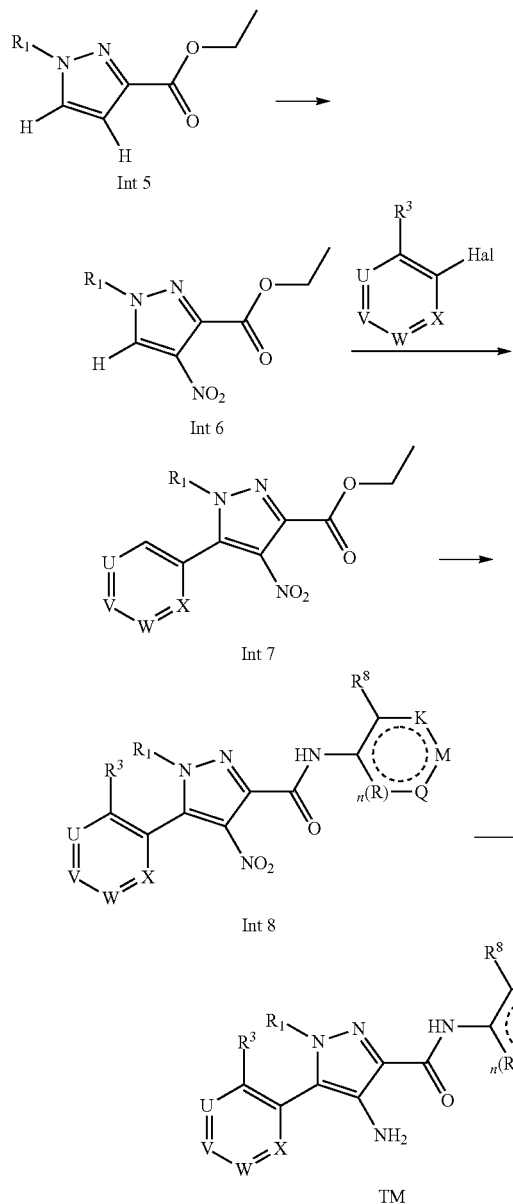

5-unsubstituted pyrazole with an aryl halogenide may provide an alternative synthesis strategy for aryl pyrazole ester formation.

Scheme 2:

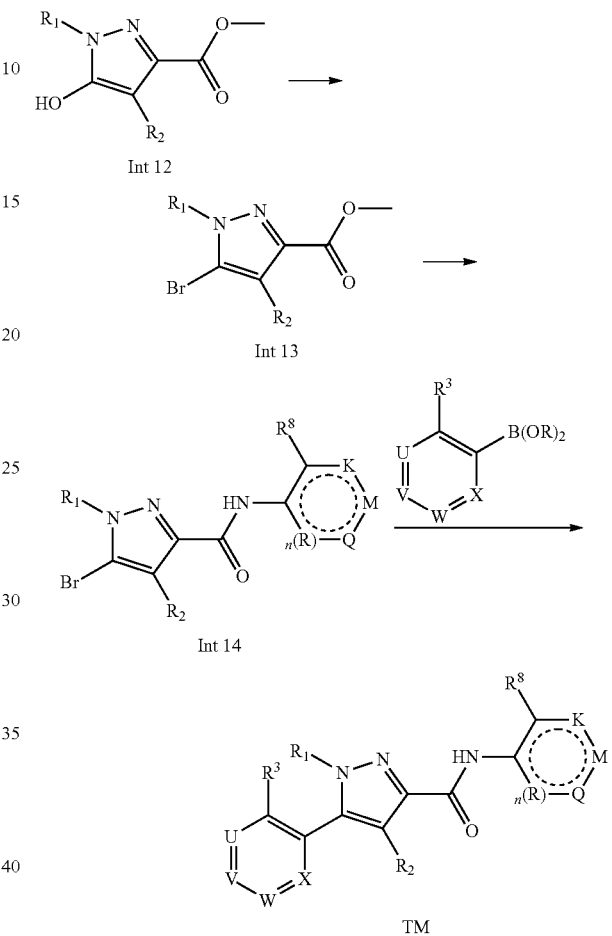

Scheme 3:

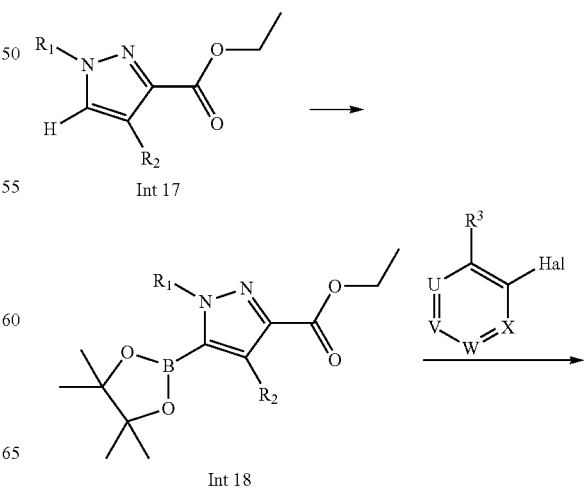

As shown in Scheme 2 and 3 alternatively Pd-catalyzed coupling methods may be used to obtain compounds of the invention. Scheme 2 illustrates the synthesis via a pyrazole bromide or triflate employed in a Suzuki cross coupling with an appropriate boronic acid or ester. The coupling may also be performed on a pyrazole ester intermediate. Scheme 3 provides an example how a 5-unsubstituted pyrazole ester is converted into a boronic ester in the presence of an iridium catalyst and bispinacolatodiborane. Suzuki coupling with an appropriate aryl halogenide or triflate subsequently gives aryl pyrazole esters that can be converted to compounds of the invention as shown in Scheme 1. A direct coupling of the

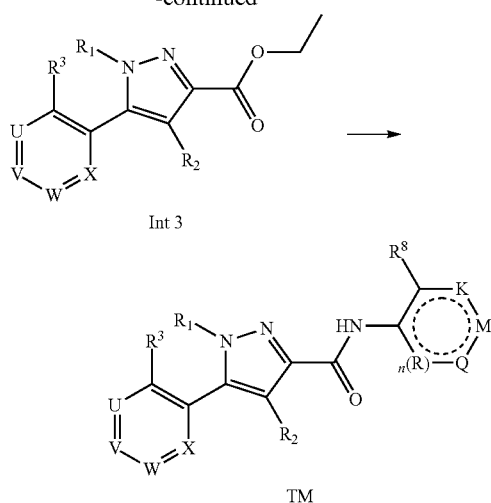

Int 3

TM

In general, further modifications may be performed on aryl pyrazole amides or esters readily assembled according to the synthesis schemes provided above. For instance a halogen substitution, preferably Br or I, in the position U, V, W or X may be transformed by a Pd catalyzed coupling as Suzuki, Stille and Negishi, or alternatively undergo a Buchwald coupling to afford compounds of the invention or their ester intermediates (Scheme 4). Other examples include the use of an carboxylic acid, ester or nitrile for further modifications and other synthesis transformation known to those skilled in the art.

Scheme 4:

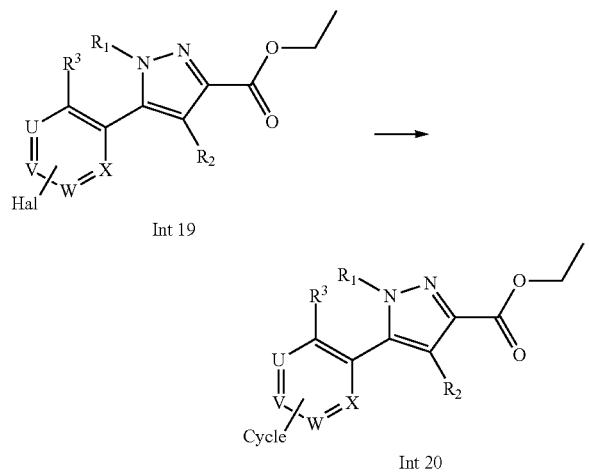

Int 19

Int 20

Exemplified Compounds

The following examples of the invention were prepared according to reaction schemes 1 to 4.

Starting materials and reagents are available from commercial suppliers such as for example Acros, Aldrich, Apollo, Fluka, FluoroChem, Lancaster, Manchester Organics, MatrixScientific, Maybridge, Merck, TCI, Oakwood, etc., or the synthesis has been described as such in the literature or the materials may be prepared by conventional methods known to those skilled in the art.

All the intermediate products and exemplary compounds were analytically characterized by means of $^1$H-NMR spectroscopy. In addition, mass spectrometry tests (MS, m/z for [M+H]$^+$) were carried out for all the exemplary compounds and selected intermediate products.

ABBREVIATIONS

The indication "equivalents" ("eq." or "eq" or "equiv.") means molar equivalents, "RT" or "rt" means room temperature (23±7° C.), "M" are indications of concentration in mol/l, "aq." means aqueous, "sat." means saturated, "sol." means solution, "conc." means concentrated.

Further Abbreviations

Cy cyclohexane
DMF N,N-dimethylformamide
EDC.HCl N-(3-dimethylaminopropyl)-N'-ethylcarbodiimide hydrochloride
Et$_2$O diethyl ether
EtOH ethanol
EtOAc ethyl acetate
h hour(s)
HATU 1-[bis(dimethylamino)methylene]-1H-1,2,3-triazolo[4,5-b]pyridinium 3-oxid hexafluorophosphate
HOBT 1-hydroxybenzotriazole
MeOH methanol
min minute(s)
PEPPSI™-Ipr [1,3-bis(2,6-Diisopropylphenyl)imidazol-2-ylidene](3-chloropyridyl)palladium(II) dichloride
Pd(dppf)Cl$_2$.CH$_2$Cl$_2$ [1,1'-bis(diphenylphosphino)ferrocene]dichloropalladium(II), complex with dichloromethane
THF tetrahydrofuran
Analytical and Purification Methods:
Liquid Chromatography with Mass Spectrometry Detection: LC-MS
Method 1:
Agilent LC-MS 1200 Rapid Resolution with detector MSD6140
Detection: MM-ES+APCI+DAD (254 nm)
Fragmentation: 50 V [pos/neg]
Column: Agilent SB-C18, 2.1×30 mm, 3.5 micron
Column temperature: 30° C.
Flow rate: 0.8 mL/min.
Runtime: 4 min.
Eluent: A: Water; B: methanol with 1 vol-% formic acid
Gradient:
  t=0 min.: 95/5 (A/B)
  t=1.00 min.: 95/5 (A/B)
  t=4.00 min.: 0/100 (A/B)
Method 2:
Agilent 1290 Infinity UHPLC-TOF system
Detection: Agilent G4212A DAD (190-400 nm)+Agilent 6224 TOF
Column: Zorbax SB-C18 Rapid Resolution HD, 2.1×50 mm
Column temperature: 80° C.
Flow rate: 2.3 mL/min
Runtime: 1.38 min.
Eluent: A: Water with 0.1 vol-% formic acid; B: acetonitrile with 0.1 vol-% formic acid
Gradient:
  t=0 min.: 98/2 (A/B)
  t=1.20 min.: 0/100 (A/B)
  t=1.29 min.: 0/100 (A/B)
  t=1.31 min.: 98/2 (A/B)
  t=1.39 min.: 98/2 (A/B)

Chromatography
Büchi MPLC system (Stationary phase: silica gel, 40-50μ)
PuriFlash 430 (Stationary phase: Interchim®-cartridges)
Preparative HPLC
Coupled LC-MS Agilent 1200/1260 Autopurification system
Column: Machery-Nagel Nucelodur ISIS C18 VP, 21×100 mm
Flow rate: 35 mL/min.
Runtime: 12 min.
Eluent: A: Water; B: methanol
Gradient: 30-100% B Synthesis of Compounds According to Present Invention Synthesis Example 1

N-(2,6-Difluoro-phenyl)-5-(2-methoxyphenyl)-1-methyl-1H-pyrazole-3-carboxylic acid amide

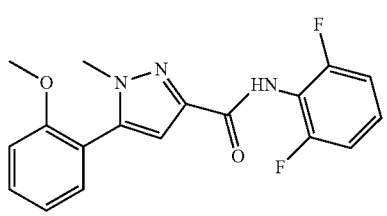 [SMILES: COc1ccccc1-c1cc(C(=O)Nc2c(F)cccc2F)nn1C]

A solution of 5-(2-methoxyphenyl)-1-methyl-1H-pyrazole-3-carboxylic acid (0.400 g) in SOCl$_2$ (3 mL) was heated to 60° C. for 1 h. The mixture was chilled and the volatiles were removed under reduced pressure. The residue was redissolved in CH$_2$Cl$_2$ (13 mL) and NEt$_3$ (219 μL) and 2,6-difluoroaniline (113 μL) were consecutively added. The mixture was stirred at ambient temperature for 16 h and was washed with sat. NH$_4$Cl. The organic layer was dried and the volatiles were removed under reduced pressure. The residue was purified by chromatography (Interchim® cartridge 50SiHP/12 g, CH$_2$Cl$_2$/MeOH) to yield the title compound of example 1 (60% yield).
LC-MS (Method 2): m/z [M+H]$^+$=344.1 (MW calc.=343.33); R$_t$=0.72 min.

Synthesis Example 2

N-(2,4-Difluoro-phenyl)-5-(2,5-dimethoxyphenyl)-1-methyl-1H-pyrazole-3-carboxylic acid amide Intermediate 2a)

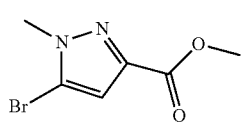

To a solution of methyl 5-hydroxy-1-methyl-1H-pyrazole-3-carboxylate (2.0 g) in CH$_3$CN (47 mL) was added phosphorus(V) oxybromide (18.3 g) and the mixture was heated to 80° C. for 18 h. The reaction mixture was chilled in an ice bath and sat. sodium carbonate solution was added. The mixture was extracted with EtOAc, the combined organic layers were dried and the volatiles were removed under reduced pressure to yield the desired product.

LC-MS (Method 2): m/z [M+H]$^+$=219.0 (MW calc.=219.04); R$_t$=0.45 min.

Intermediate 2b)

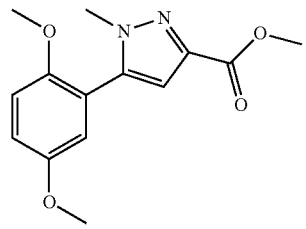 [SMILES: COC(=O)c1cc(-c2cc(OC)ccc2OC)n(C)n1]

A solution of intermediate 2a (515 mg), 2,5-dimethoxyphenylboronic acid (642 mg) and Pd(dppf)Cl$_2$.CH$_2$Cl$_2$ (105 mg) in a mixture of THF (15 mL) and sodium carbonate solution (2 M, 3 mL) was heated in a microwave (Biotage®) to 100° C. for 1.5 h. The mixture was chilled, the layers separated and the aqueous layer was extracted with EtOAc. The combined organic layers were dried and the volatiles were removed under reduced pressure. The residue was purified by chromatography (Interchim® cartridge 50SiHP/25 g, Cy/EtOAc) to yield the desired compound (77% yield).
LC-MS (Method 2): m/z [M+H]$^+$=277.1 (MW calc.=276.29); R$_t$=0.62 min.

Intermediate 2c)

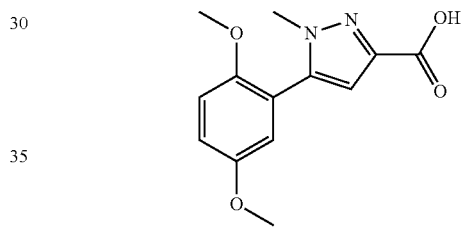

A solution of intermediate 2b (307 mg) in dioxane (2 mL) was treated with aqueous LiOH solution (2 M, 0.5 mL) and the mixture was stirred at 70° C. for 1 h. HCl (1 M) was added and the mixture was extracted with EtOAc. The combined organic layers were dried and the volatiles were removed under reduced pressure to yield the desired compound (93% yield).
LC-MS (Method 2): m/z [M+H]$^+$=263.3 (MW calc.=262.26); R$_t$=0.68 min.

N-(2,4-Difluoro-phenyl)-5-(2,5-dimethoxyphenyl)-1-methyl-1H-pyrazole-3-carboxylic acid amide Example 2

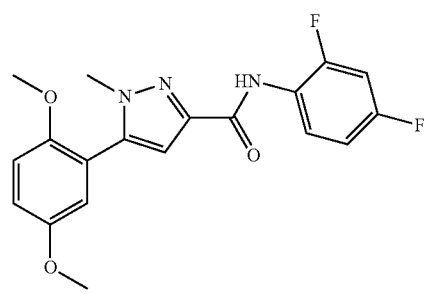 [SMILES: COc1ccc(OC)c(-c2cc(C(=O)Nc3ccc(F)cc3F)nn2C)c1]

To a solution of intermediate 2c (50 mg) and 2,4-difluoroaniline (29 mg) in dry N,N-dimethyl formamide (2.2 mL) were consecutively added O-(7-Aza-1H-benzotriazole-1-yl)-N,N,N',N'-tetramethyluronium hexafluorophosphate (91 mg) and N,N-diisopropylethylamine (114 µL) and the mixture was stirred at ambient temperature for 18 h. The solution was poured into sodium bicarbonate solution and was extracted with EtOAc. The organic layer was washed with water and was dried and the volatiles were removed under reduced pressure. The residue was purified by chromatography (Interchim® cartridge50SiHP/12 g, Cy/EtOAc) to yield the title compound of example 2 (55% yield).

LC-MS (Method 2): m/z [M+H]$^+$=374.1 (MW calc.=373.35); R$_t$=0.80 min.

Synthesis Example 3

5-(2-Ethoxy-5-methoxy-phenyl)-N-(3-fluoro-pyridin-4-yl)-1-methyl-1H-pyrazole-3-carboxylic acid amide Intermediate 3a)

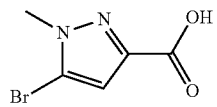

A solution of intermediate 2a (506 mg) in dioxane (10 mL) was treated with LiOH solution (2 M, 1 mL) and the mixture was stirred at 70° C. for 1 h. HCl (1 M) was added and the mixture was extracted with EtOAc. The combined organic layers were dried and the volatiles were removed under reduced pressure to yield the desired compound (84% yield).

LC-MS (Method 2): m/z [M+H]$^+$=205.0 (MW calc.=205.01); R$_t$=0.31 min.

Intermediate 3b)

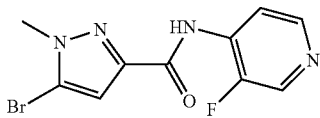 [SMILES: Cn1nc(C(=O)Nc2ccncc2F)cc1Br]

Intermediate 3b was prepared in analogy to the preparation of the title compound of example 1 through the reaction of intermediate 3a (400 mg) with 3-fluoropyridin-4-amine (248 mg) (78% yield).

LC-MS (Method 2): m/z [M+H]$^+$=299.0 (MW calc.=299.10); R$_t$=0.52 min.

5-(2-Ethoxy-5-methoxy-phenyl)-N-(3-fluoro-pyridin-4-yl)-1-methyl-1H-pyrazole-3-carboxylic acid amide

Example 3

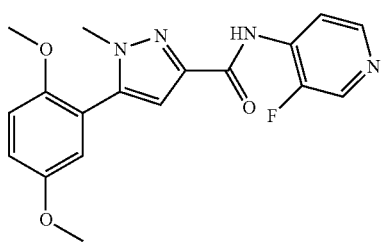 [SMILES: COc1ccc(OC)c(-c2cc(C(=O)Nc3ccncc3F)nn2C)c1]

The title compound of example 3 was prepared in analogy to the preparation of intermediate 2b through the reaction of intermediate 3b (100 mg) with 2-ethoxy-5-methoxyphenyl-boronic acid (115 mg) (49% yield).

LC-MS (Method 2): m/z [M+H]$^+$=371.2 (MW calc.=370.38); R$_t$=0.74 min.

Synthesis Example 4

N-(2,6-Difluoro-phenyl)-5-(2-ethoxy-5-methoxy-phenyl)-1-methyl-1H-pyrazole-3-carboxylic acid amide Intermediate 4a)

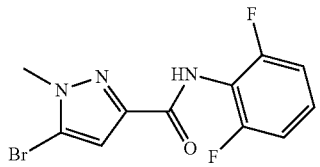 [SMILES: Cn1nc(C(=O)Nc2c(F)cccc2F)cc1Br]

Intermediate 4b was prepared in analogy to the preparation of the title compound of example 1 through the reaction of intermediate 3a (700 mg) with 2,6-difluoroaniline (445 mg) (42% yield).

LC-MS (Method 2): m/z [M+H]$^+$=316.0 (MW calc.=316.10); R$_t$=0.77 min.

N-(2,6-Difluoro-phenyl)-5-(2-ethoxy-5-methoxy-phenyl)-1-methyl-1H-pyrazole-3-carboxylic acid amide

Example 4

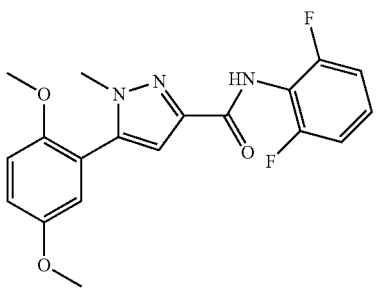 [SMILES: COc1ccc(OC)c(-c2cc(C(=O)Nc3c(F)cccc3F)nn2C)c1]

The title compound of example 4 was prepared in analogy to the preparation of intermediate 2b through the reaction of intermediate 4a (120 mg) with 2-ethoxy-5-methoxyphenyl-boronic acid (134 mg) (42% yield).

LC-MS (Method 2): m/z [M+H]$^+$=388.1 (MW calc.=387.38); R$_t$=0.78 min.

Synthesis Example 5

5-(2,5-Difluoro-phenyl)-N-(2,6-difluoro-phenyl)-1-methyl-1H-pyrazole-3-carboxylic acid amide

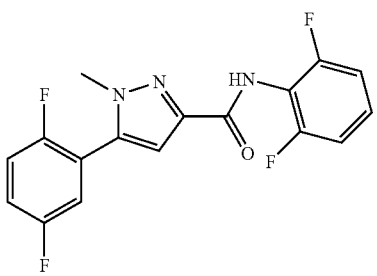 [SMILES: Cn1nc(C(=O)Nc2c(F)cccc2F)cc1-c1cc(F)ccc1F]

The title compound of example 5 was prepared in analogy to the preparation of intermediate 2b through the reaction of intermediate 4a (150 mg) with 2,5-difluorophenylboronic acid (135 mg) (57% yield).

LC-MS (Method 2): m/z [M+H]$^+$=350.1 (MW calc.=349.28); R$_t$=0.72 min.

Synthesis Example 6

N-(2,6-Difluoro-phenyl)-5-[2-fluoro-5-(trifluoromethyl)-phenyl]-1-methyl-1H-pyrazole-3-carboxylic acid amide

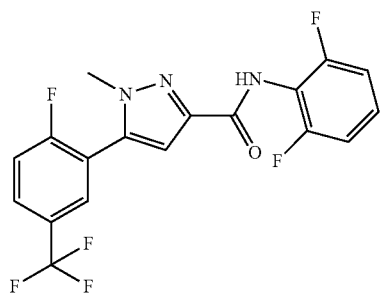 [SMILES: Cn1nc(C(=O)Nc2c(F)cccc2F)cc1-c1cc(C(F)(F)F)ccc1F]

The title compound of example 6 was prepared in analogy to the preparation of intermediate 2b through the reaction of intermediate 4a (150 mg) with 2-Fluoro-5-(trifluoromethyl)benzeneboronic acid (177 mg) (20% yield).

LC-MS (Method 2): m/z [M+H]$^+$=400.1 (MW calc.=399.29); R$_t$=0.80 min.

Synthesis Example 7

N-(2,6-Difluoro-phenyl)-1-methyl-5-[2-(trifluoromethyl)-phenyl]-1H-pyrazole-3-carboxylic acid amide Intermediate 7a)

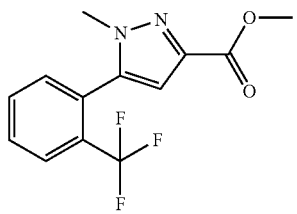 [SMILES: COC(=O)c1cc(-c2ccccc2C(F)(F)F)n(C)n1]

A solution of intermediate 2a (500 mg), 2-(trifluoromethyl)beneneboronic acid (650 mg), PEPPSI™-Ipr (77 mg) and potassium carbonate (939 mg) in dioxane (10 mL) were heated to 120° C. for 18 h. The mixture was chilled, filtered and the volatiles were removed under reduced pressure. The residue was purified by chromatography (Interchim® cartridge50SiHP/12 g, Cy/EtOAc) to yield the desired compound (55% yield).

LC-MS (Method 2): m/z [M+H]$^+$=285.2 (MW calc.=284.23); R$_t$=0.83 min.

Intermediate 7b)

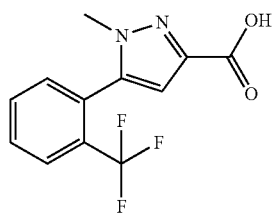 [SMILES: Cn1nc(C(=O)O)cc1-c1ccccc1C(F)(F)F]

Intermediate 7b was prepared in analogy to the preparation of intermediate 3a starting from intermediate 7a (550 mg) (70% yield).

LC-MS (Method 2): m/z [M+H]$^+$=271.1 (MW calc.=270.21); R$_t$=0.55 min.

N-(2,6-Difluoro-phenyl)-1-methyl-5-[2-(trifluoromethyl)-phenyl]-1H-pyrazole-3-carboxylic acid amide Example 7

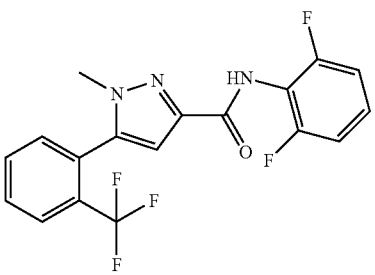 [SMILES: Cn1nc(C(=O)Nc2c(F)cccc2F)cc1-c1ccccc1C(F)(F)F]

The title compound of example 7 was prepared in analogy to the preparation of the title compound of example 1 through the reaction of intermediate 7b (190 mg) with 2,6-difluoroaniline (93 mg) (44% yield).

LC-MS (Method 2): m/z [M+H]$^+$=382.1 (MW calc.=381.30); R$_t$=0.76 min.

Synthesis Example 8

N-(2,6-Difluoro-phenyl)-5-[5-methoxy-2-(trifluoromethyloxy)-phenyl]-1-methyl-1H-pyrazole-3-carboxylic acid amide Intermediate 8a)

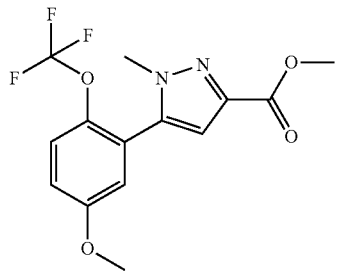 [SMILES: COC(=O)c1cc(-c2cc(OC)ccc2OC(F)(F)F)n(C)n1]

Intermediate 8a was prepared in analogy to the preparation of intermediate 2b through the reaction of intermediate 2a (396 mg) with 5-methoxy-2-(trifluoromethoxy)phenylboronic acid (766 mg) (53% yield).

LC-MS (Method 2): m/z [M+H]$^+$=331.2 (MW calc.=330.26); R$_t$=0.90 min.

Intermediate 8b)

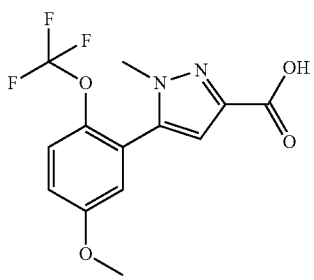 [SMILES: COc1ccc(OC(F)(F)F)c(-c2cc(C(=O)O)nn2C)c1]

Intermediate 8b was prepared in analogy to the preparation of intermediate 3a starting from intermediate 8a (318 mg) (94% yield).
LC-MS (Method 2): m/z[M+H]$^+$=317.1 (MW calc.=316.23); $R_t$=0.82 min.

N-(2,6-Difluoro-phenyl)-5-[5-methoxy-2-(trifluoromethyloxy)-phenyl]-1-methyl-1H-pyrazole-3-carboxylic acid amide Example 8

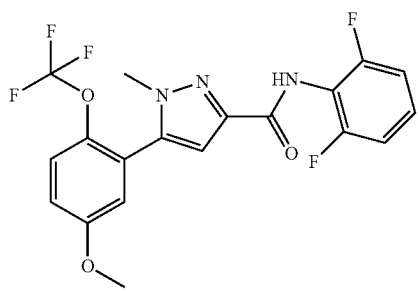 [SMILES: COc1ccc(OC(F)(F)F)c(-c2cc(C(=O)Nc3c(F)cccc3F)nn2C)c1]

The title compound of example 8 was prepared in analogy to the preparation of the title compound of example 1 through the reaction of intermediate 8b (285 mg) with 2,6-difluoroaniline (60 mg) (24% yield).
LC-MS (Method 2): m/z [M+H]$^+$=428.1 (MW calc.=427.32); $R_t$=0.82 min.

Synthesis Example 9

N-(3-Fluoro-pyridin-4-yl)-5-[5-methoxy-2-(trifluoromethyloxy)-phenyl]-1-methyl-1H-pyrazole-3-carboxylic acid amide

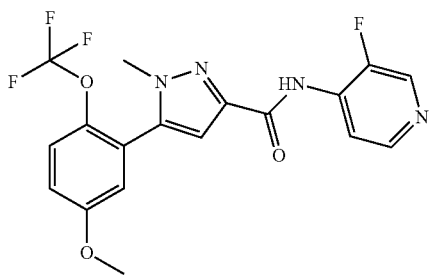 [SMILES: COc1ccc(OC(F)(F)F)c(-c2cc(C(=O)Nc3ccncc3F)nn2C)c1]

The title compound of example 9 was prepared in analogy to the preparation of the title compound of example 1 through the reaction of intermediate 8b (143 mg) with 3-fluoropyridin-4-amine (52 mg) (65% yield).
LC-MS (Method 2): m/z [M+H]$^+$=411.1 (MW calc.=410.32); $R_t$=0.80 min.

Synthesis Example 10

N-(2,6-Difluoro-phenyl)-5-(5-fluoro-2-methoxyphenyl)-1-methyl-1H-pyrazole-3-carboxylic acid amide

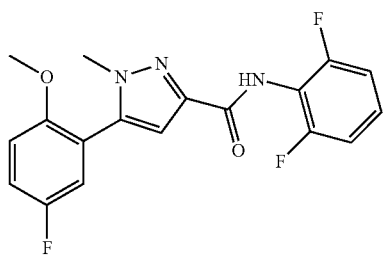 [SMILES: COc1ccc(F)cc1-c1cc(C(=O)Nc2c(F)cccc2F)nn1C]

The title compound of example 10 was prepared in analogy to the preparation of the title compound of example 1 through the reaction of 5-(5-fluoro-2-methoxyphenyl)-1-methyl-1H-pyrazole-3-carboxylic acid (201 mg) with 2,6-difluoroaniline (105 mg) (22% yield).
LC-MS (Method 2): m/z [M+H]$^+$=362.1 (MW calc.=361.32); $R_t$=0.73 min.

Synthesis Example 11

5-[2-Chloro-4-(trifluoromethyloxy)-phenyl]-N-(3-fluoro-pyridin-4-yl)-1-methyl-1H-pyrazole-3-carboxylic acid amide Intermediate 11a)

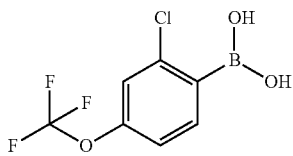 [SMILES: OB(O)c1ccc(OC(F)(F)F)cc1Cl]

To a solution of 1-Bromo-2-Chloro-4-(trifluoromethoxy)benzene (300 mg) in dry THF (1.3 mL) was added isopropylmagnesium chloride lithium chloride complex solution (1.3 M in THF, 1.0 mL) at 0° C. and the resulting mixture was stirred at ambient temperature for 2 h. Trimethyl borate (244 µL) was added at 0° C. and the reaction mixture was stirred at ambient temperature for 1 h. HCl (0.1 M, 1 mL) was added and the mixture was extracted with EtOAc. The combined organic layers were dried and the volatiles were removed under reduced pressure to yield the desired compound (77% yield).

5-[2-Chloro-4-(trifluoromethyloxy)-phenyl]-N-(3-fluoro-pyridin-4-yl)-1-methyl-1H-pyrazole-3-carboxylic acid amide Example 11

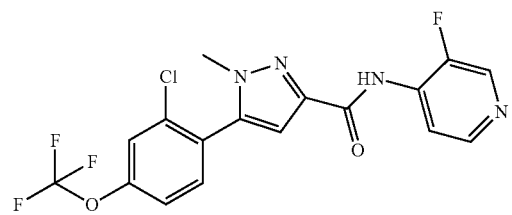 [SMILES: Cn1nc(C(=O)Nc2ccncc2F)cc1-c1ccc(OC(F)(F)F)cc1Cl]

The title compound of example 11 was prepared in analogy to the preparation of intermediate 2b through the reaction of intermediate 3b (90 mg) with intermediate 11a (160 mg) (49% yield).

LC-MS (Method 2): m/z[M+H]$^+$=415.1 (MW calc.=414.05); R$_t$=0.85 min.

Synthesis Example 12

5-[2-Chloro-4-(trifluoromethyloxy)-phenyl]-N-(2,6-difluoro-phenyl)-1-methyl-1H-pyrazole-3-carboxylic acid amide

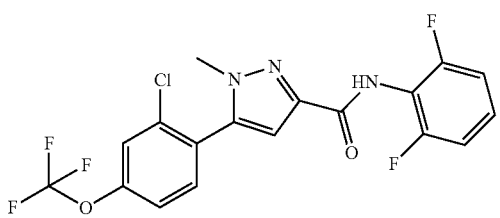 [SMILES: Cn1nc(C(=O)Nc2c(F)cccc2F)cc1-c1ccc(OC(F)(F)F)cc1Cl]

The title compound of example 12 was prepared in analogy to the preparation of intermediate 2b through the reaction of intermediate 4a (90 mg) with intermediate 11a (137 mg) (49% yield).

LC-MS (Method 2): m/z [M+H]$^+$=432.1 (MW calc.=431.74); R$_t$=0.86 min.

Synthesis Example 13

5-(2,5-Dimethoxyphenyl)-N-(2-fluoro-4-methylsulfonyl-phenyl)-1-methyl-1H-pyrazole-3-carboxylic acid amide

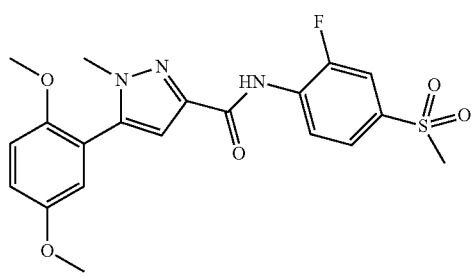 [SMILES: COc1ccc(OC)c(-c2cc(C(=O)Nc3ccc(S(C)(=O)=O)cc3F)nn2C)c1]

To a solution of intermediate 2c (105 mg) and 2-fluoro-4-(methylsulfonyl)aniline (151 mg) in dry N,N-dimethyl formamide (2 mL) were consecutively added O-(7-Aza-1H-benzotriazole-1-yl)-N,N,N',N'-tetramethyluronium hexafluorophosphate (190 mg) and N,N-diisopropylethylamine (103 mg) and the mixture was stirred at 50° C. for 18 h. The volatiles were removed under reduced pressure and the residue was purified by preparative HPLC (40% yield)

LC-MS (Method 2): m/z [M+H]$^+$=434.1 (MW calc.=433.45); R$_t$=0.73 min.

Synthesis Example 14

5-(2,5-Dimethoxyphenyl)-1-methyl-N-[3-(trifluoromethyl)-pyridin-4-yl]-1H-pyrazole-3-carboxylic acid amide

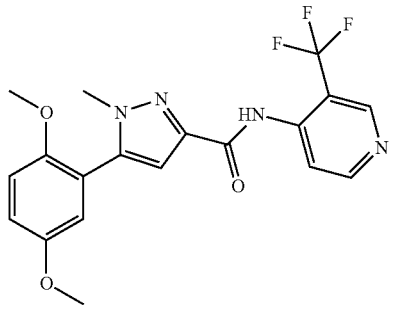 [SMILES: COc1ccc(OC)c(-c2cc(C(=O)Nc3ccncc3C(F)(F)F)nn2C)c1]

The title compound of example 14 was prepared in analogy to the preparation of the title compound of example 13 through the reaction of intermediate 2c (105 mg) with 2-(trifluoromethyl)aniline (129 mg) (43% yield).

LC-MS (Method 2): m/z [M+H]$^+$=407.1 (MW calc.=406.36); R$_t$=0.84 min.

Synthesis Example 15

N-(3-Cyano-pyridin-4-yl)-5-(2,5-dimethoxyphenyl)-1-methyl-1H-pyrazole-3-carboxylic acid amide

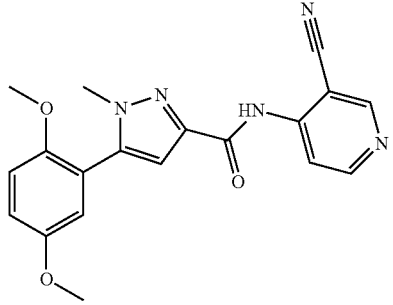 [SMILES: COc1ccc(OC)c(-c2cc(C(=O)Nc3ccncc3C#N)nn2C)c1]

The title compound of example 15 was prepared in analogy to the preparation of the title compound of example 13 through the reaction of intermediate 2c (105 mg) with 4-aminonicotinonitrile (95 mg) (31% yield).

LC-MS (Method 2): m/z [M+H]$^+$=364.1 (MW calc.=363.37); R$_t$=0.73 min.

Synthesis Example 16

5-(2,5-Dimethoxyphenyl)-1-methyl-N-(4-methyl-pyridin-3-yl)-1H-pyrazole-3-carboxylic acid amide

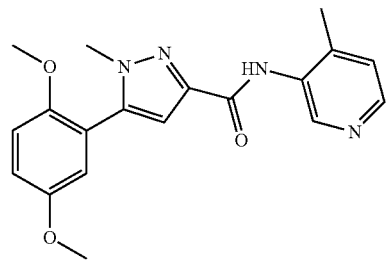 [SMILES: COc1ccc(OC)c(-c2cc(C(=O)Nc3cnccc3C)nn2C)c1]

The title compound of example 16 was prepared in analogy to the preparation of the title compound of example 13 through the reaction of intermediate 2c (105 mg) with 4-methylpyridin-3-amine (87 mg) (75% yield).

LC-MS (Method 2): m/z [M+H]$^+$=353.1 (MW calc.=352.39); R$_t$=0.50 min.

Synthesis Example 17

5-(2,5-Dimethoxyphenyl)-N-(4,6-dimethyl-pyridin-3-yl)-1-methyl-1H-pyrazole-3-carboxylic acid amide

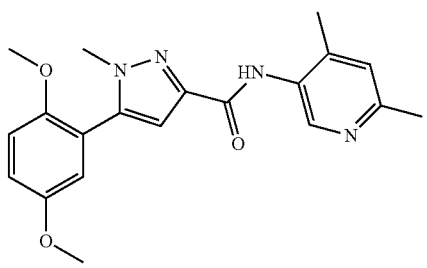 [SMILES: COc1ccc(OC)c(-c2cc(C(=O)Nc3cnc(C)cc3C)nn2C)c1]

The title compound of example 17 was prepared in analogy to the preparation of the title compound of example 13 through the reaction of intermediate 2c (105 mg) with 4,6-dimethylpyridin-3-amine (98 mg) (71% yield).

LC-MS (Method 2): m/z [M+H]$^+$=367.1 (MW calc.=366.41); R$_t$=0.50 min.

Synthesis Example 18

5-(2,5-Dimethoxyphenyl)-1-methyl-N-(5-methyl-pyrimidin-4-yl)-1H-pyrazole-3-carboxylic acid amide

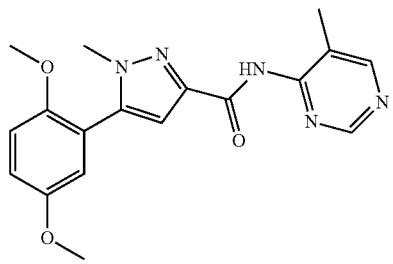 [SMILES: COc1ccc(OC)c(-c2cc(C(=O)Nc3ncncc3C)nn2C)c1]

The title compound of example 18 was prepared in analogy to the preparation of the title compound of example 13 through the reaction of intermediate 2c (105 mg) with 5-methylpyrimidin-4-amine (87 mg) (20% yield).

LC-MS (Method 2): m/z [M+H]$^+$=354.2 (MW calc.=353.15); R$_t$=0.61 min.

Synthesis Example 19

5-(2,5-Dimethoxyphenyl)-N-(3-fluoro-pyridin-4-yl)-1-methyl-1H-pyrazole-3-carboxylic acid amide

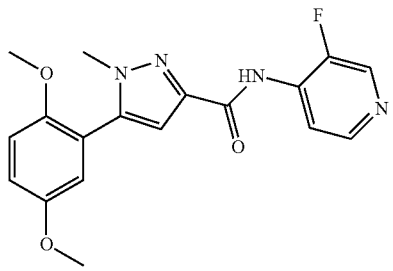 [SMILES: COc1ccc(OC)c(-c2cc(C(=O)Nc3ccncc3F)nn2C)c1]

The title compound of example 19 was prepared in analogy to the preparation of the title compound of example 1 through the reaction of intermediate 2c (390 mg) with 3-fluoropyridin-4-amine (192 mg) (24% yield).

LC-MS (Method 2): m/z [M+H]$^+$=357.2 (MW calc.=356.35); R$_t$=0.68 min.

Synthesis Example 20

5-(2,5-Dimethoxyphenyl)-1-methyl-N-(3-methyl-pyridin-4-yl)-1H-pyrazole-3-carboxylic acid amide

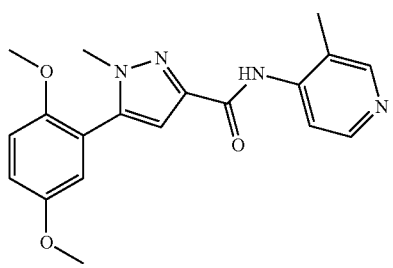 [SMILES: COc1ccc(OC)c(-c2cc(C(=O)Nc3ccncc3C)nn2C)c1]

To a solution of intermediate 2c (100 mg) in CH$_2$Cl$_2$ (7 mL) were consecutively added N,N-Diisopropylethylamine (140 µL), 3-methylpyridin-4-amine (40 mg) and bromotripyrrolidinophosphonium hexafluorophosphate (230 mg) and the mixture was stirred at ambient temperature for 2 h. The volatiles were removed under reduced pressure and the residue was purified by column chromatography (Interchim® cartridge50SiHP/25 g, Cy/EtOAc) to yield the desired compound (84% yield).

LC-MS (Method 2): m/z [M+H]$^+$=353.2 (MW calc.=352.39); R$_t$=0.48 min.

Synthesis Example 21

N-(2,6-Difluoro-phenyl)-5-(2,5-dimethoxyphenyl)-1-methyl-1H-pyrazole-3-carboxylic acid amide

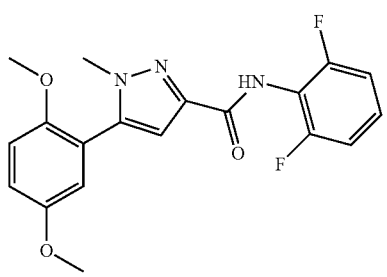 [SMILES: COc1ccc(OC)c(-c2cc(C(=O)Nc3c(F)cccc3F)nn2C)c1]

The title compound of example 21 was prepared in analogy to the preparation of the title compound of example 13 through the reaction of intermediate 2c (29 mg) with 2,6-difluoroaniline (17 mg) (45% yield).

LC-MS (Method 2): m/z [M+H]$^+$=374.1 (MW calc.=373.35); R$_t$=0.72 min.

Synthesis Example 22

5-(5-Chloro-2-methoxy-phenyl)-N-(3-fluoro-pyridin-4-yl)-1-methyl-1H-pyrazole-3-carboxylic acid amide Intermediate 22a)

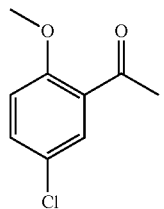

A solution of 1-(5-chloro-2-hydroxyphenyl)ethanone (3.4 g) in acetone (40 mL) was added potassium carbonate (8.2 g) and the mixture was stirred at ambient temperature for 1 h. Methyl iodide (3.7 g) was added and the reaction mixture was stirred at ambient temperature for 15 h. The suspension was filtered and the volatiles were removed under reduced pressure. The residue was dissolved in Et$_2$O and was washed with water. The organic layer was dried and the volatiles were removed under reduced pressure to yield the desired compound (90% yield).

Intermediate 22b)

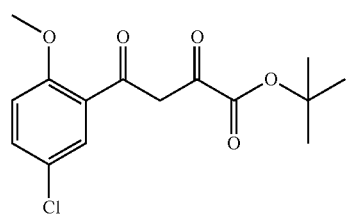 [SMILES: COc1ccc(Cl)cc1C(=O)CC(=O)C(=O)OC(C)(C)C]

A solution of intermediate 22a (3.24 g) in Et$_2$O (150 mL) was treated at −78° C. with lithium bis(trimethylsilyl)amide (1 m in THF, 19.8 mL) and was stirred at this temperature for 45 min. A solution of di-tert-butyl oxalate (4.38 g) in Et$_2$O was added and the mixture was stirred at ambient temperature for 20 h and at 60° C. for 3 h. The mixture was treated with 1 M HCl (145 mL) and the aqueous layer was extracted with EtOAc. The combined organic layers were dried and the volatiles were removed under reduced pressure. The residue was purified by chromatography (SiO$_2$, 400 g, Cy/CHCl$_3$) to yield the desired compound (65% yield).

Intermediate 22c)

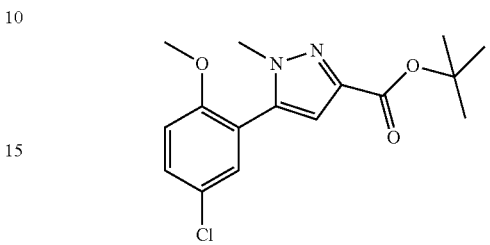

A suspension of intermediate 22b (3.3 g) in ethanol (50 mL) was treated with methyl hydrazine (830 μL) at 0° C. and the mixture was stirred at 80° C. for 1 h. The volatiles were removed under reduced pressure and the residue was purified by chromatography (SiO$_2$, 400 g, Cy/EtOAc) to yield the desired compound (10% yield).

LC-MS (Method 1): m/z [M+H]$^+$=323.2 (MW calc.=322.79); R$_t$=4.2 min.

Intermediate 22d)

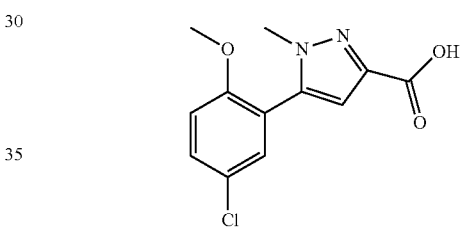

A solution of intermediate 22c (341 mg) in CH$_2$Cl$_2$ (4 mL) was treated with trifluoroacetic acid (3 mL) and was stirred at ambient temperature for 2 h. The volatiles were removed under reduced pressure to yield the desired compound (87% yield).

5-(5-Chloro-2-methoxy-phenyl)-N-(3-fluoro-pyridin-4-yl)-1-methyl-1H-pyrazole-3-carboxylic acid amide Example 22

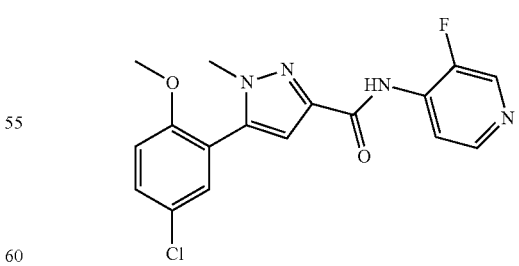

The title compound of example 22 was prepared in analogy to the preparation of the title compound of example 1 through the reaction of intermediate 22d (297 mg) with 3-fluoropyridin-4-amine (132 mg) (40% yield).

LC-MS (Method 2): m/z [M+H]$^+$=361.1 (MW calc.=360.77); R$_t$=0.73 min.

Synthesis Example 23

5-(5-Chloro-2-methyl-phenyl)-N-(3-fluoro-pyridin-4-yl)-1-methyl-1H-pyrazole-3-carboxylic acid amide Intermediate 23a)

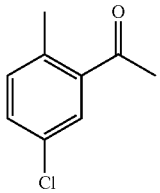

Methyl magnesium bromide (3 M, 19.7 mL) was added to a solution of 5-chloro-2-methylbenzonitrile (4.0 g) in dry THF (20 mL) and the mixture was stirred at 65° C. for 15 h. Saturated ammonium chloride solution was added and the mixture was extracted with EtOAc. The combined organic layers were dried and the volatiles were removed under reduce pressure. The residue was treated with 4 M HCl, stirred overnight and was extracted with EtOAc. The combined organic layers were dried and the volatiles were removed under reduce pressure to yield the desired compound (69% yield).

Intermediate 23b)

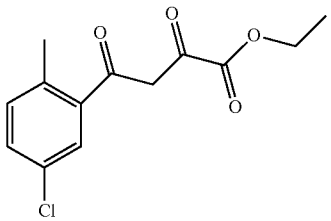 [SMILES: CCOC(=O)C(=O)CC(=O)c1cc(Cl)ccc1C]

Sodium (465 mg) was dissolved in dry ethanol (25 mL) and subsequently solutions of diethyl oxalate (2.91 g) in dry $Et_2O$ (10 mL) and intermediate 23a (3.05 g) in $Et_2O$ (10 mL) were added. The reaction mixture was stirred at ambient temperature for 3d followed by addition of 1 N aqueous HCl and extraction with EtOAc. The combined organic layers were dried and the solvent removed under reduced pressure to yield crude material of the desired product (95% yield).

Intermediate 23c)

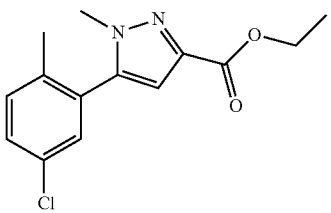 [SMILES: CCOC(=O)c1cc(-c2cc(Cl)ccc2C)n(C)n1]

Intermediate 23c was prepared in analogy to the preparation of intermediate 22c through the reaction of intermediate 23b (2.3 g) with methyl hydrazine (660 μL) (42% yield).

Intermediate 23d)

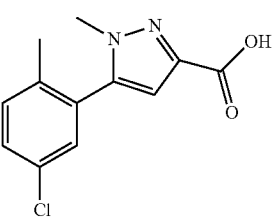 [SMILES: Cc1ccc(Cl)cc1-c1cc(C(=O)O)nn1C]

A solution of intermediate 23c (1 g) in THF (8.5 mL) was treated with 2 M LiOH (4.3 mL) and the resulting mixture was stirred at ambient temperature overnight. The mixture was treated with 2 M HCl and was extracted with EtOAc. The combined organic layers were dried and the volatiles were removed under reduced pressure to yield the desired compound (91% yield).

5-(5-Chloro-2-methyl-phenyl)-N-(3-fluoro-pyridin-4-yl)-1-methyl-1H-pyrazole-3-carboxylic acid amide Example 23

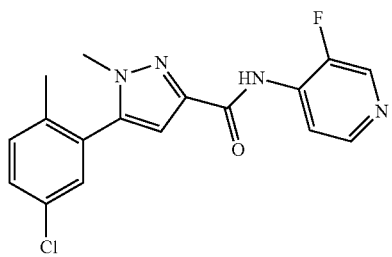 [SMILES: Cc1ccc(Cl)cc1-c1cc(C(=O)Nc2ccncc2F)nn1C]

The title compound of example 23 was prepared in analogy to the preparation of the title compound of example 1 through the reaction of intermediate 23d (410 mg) with 3-fluoropyridin-4-amine (203 mg) (40% yield).

LC-MS (Method 2): m/z $[M+H]^+$=345.1 (MW calc.=344.77); $R_t$=0.77 min.

Synthesis Example 24

N-(3-Fluoro-pyridin-4-yl)-5-(4-methoxy-2-methyl-phenyl)-1-methyl-1H-pyrazole-3-carboxylic acid amide Intermediate 24a)

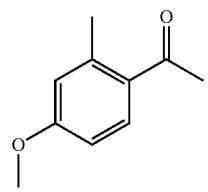

Intermediate 24a was prepared in analogy to the preparation of intermediate 22a starting from 1-(4-hydroxy-2-methylphenyl)ethanone (5 g) (93% yield).

Intermediate 24b)

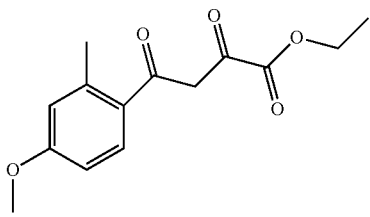 [SMILES: CCOC(=O)C(=O)CC(=O)c1ccc(OC)cc1C]

Intermediate 24b was prepared in analogy to the preparation of intermediate 23b starting from intermediate 24a (3 g) (90% yield).

Intermediate 24c)

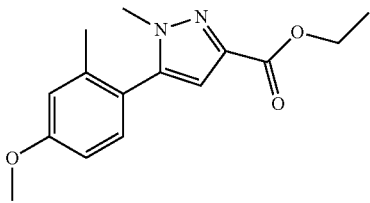 [SMILES: CCOC(=O)c1cc(-c2ccc(OC)cc2C)n(C)n1]

Intermediate 23c was prepared in analogy to the preparation of intermediate 22c through the reaction of intermediate 24b (4.3 g) with methyl hydrazine (1.27 mL) (43% yield).

Intermediate 24d)

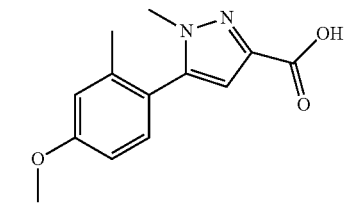 [SMILES: COc1ccc(-c2cc(C(=O)O)nn2C)c(C)c1]

Intermediate 24d was prepared in analogy to the preparation of intermediate 23d starting from intermediate 24c (950 mg) (82% yield).

N-(3-Fluoro-pyridin-4-yl)-5-(4-methoxy-2-methylphenyl)-1-methyl-1H-pyrazole-3-carboxylic acid amide Example 24

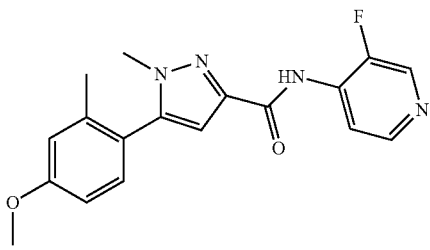 [SMILES: COc1ccc(-c2cc(C(=O)Nc3ccncc3F)nn2C)c(C)c1]

The title compound of example 24 was prepared in analogy to the preparation of the title compound of example 1 through the reaction of intermediate 24d (350 mg) with 3-fluoropyridin-4-amine (168 mg) (51% yield).

LC-MS (Method 2): m/z [M+H]$^+$=341.1 (MW calc.=340.35); $R_t$=0.70 min.

Synthesis Example 25

5-(2,5-Dimethoxyphenyl)-N-(3-fluoro-pyridin-4-yl)-1,4-dimethyl-1H-pyrazole-3-carboxylic acid amide Intermediate 25a)

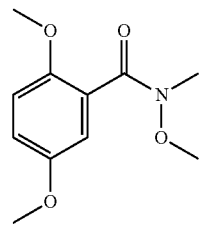 [SMILES: COc1ccc(OC)c(C(=O)N(C)OC)c1]

A solution of 2,5-dimethoxybenzoic acid (5.00 g) in thionyl chloride (20 mL) was heated to 70° C. for 1 h. The volatiles were removed under reduced pressure and the residue was dissolved in CH$_2$Cl$_2$ (20 mL). This solution was added to a solution of N,O-dimethylhydroxylamine hydrochloride (2.95 g) and NEt$_3$ (4.12 mL) in CH$_2$Cl$_2$ (40 mL) at 0° C. and the resulting mixture was stirred at ambient temperature overnight. Saturated ammonium chloride solution was added and the mixture was extracted with CH$_2$Cl$_2$. The combined organic layers were washed with saturated sodium bicarbonate solution and brine and were dried. The volatiles were removed under reduced pressure to yield the desired product (80% yield).

Intermediate 25b)

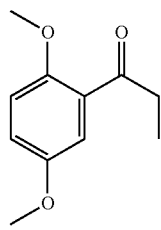

Ethyl magnesium bromide (3 M in Et$_2$O, 5 mL) was added to a solution of intermediate 25a (1.94 g) in THF (40 mL) at 0° C. and the resulting mixture was stirred at ambient temperature overnight. The reaction mixture was treated with 20% HCl (70 mL) and was extracted with EtOAc. The combined organic layers were washed with brine and dried. The volatiles were removed under reduced pressure to yield the desired compound (77%).

Intermediate 25c)

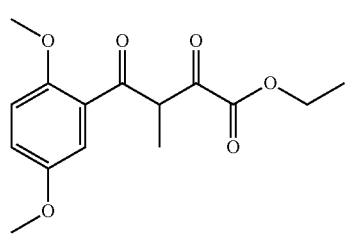 [SMILES: CCOC(=O)C(=O)C(C)C(=O)c1cc(OC)ccc1OC]

Intermediate 25c was prepared in analogy to the preparation of intermediate 23b starting from intermediate 25b (1.48 g) (73% yield).

LC-MS (Method 1): m/z [M+H]$^+$=295.2 (MW calc.=294.30); R$_t$=3.4 min.

Intermediate 25d)

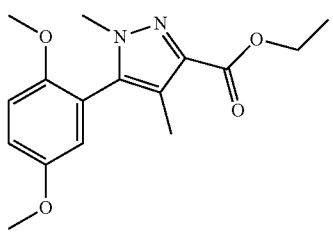 [SMILES: CCOC(=O)c1nn(C)c(-c2cc(OC)ccc2OC)c1C]

Intermediate 25d was prepared in analogy to the preparation of intermediate 22c through the reaction of intermediate 24b (4.3 g) with methyl hydrazine (1.27 mL) (33% yield).

Intermediate 25e)

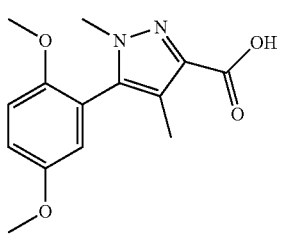 [SMILES: COc1ccc(OC)c(-c2c(C)c(C(=O)O)nn2C)c1]

Intermediate 25e was prepared in analogy to the preparation of intermediate 23d starting from intermediate 25d (276 mg) (83% yield).

5-(2,5-Dimethoxyphenyl)-N-(3-fluoro-pyridin-4-yl)-1,4-dimethyl-1H-pyrazole-3-carboxylic acid amide Example 25

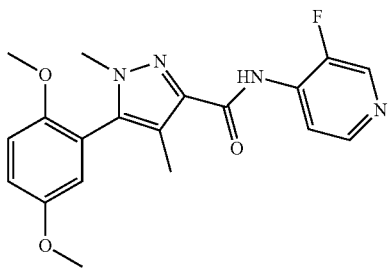 [SMILES: COc1ccc(OC)c(-c2c(C)c(C(=O)Nc3ccncc3F)nn2C)c1]

The title compound of example 25 was prepared in analogy to the preparation of the title compound of example 1 through the reaction of intermediate 25e (210 mg) with 3-fluoropyridin-4-amine (93 mg) (28% yield).

LC-MS (Method 2): m/z [M+H]$^+$=371.2 (MW calc.=370.38); R$_t$=0.73 min.

Synthesis Example 26

5-(5-Chloro-2-methyl-phenyl)-N-(2,6-difluoro-phenyl)-1-methyl-1H-pyrazole-3-carboxylic acid amide

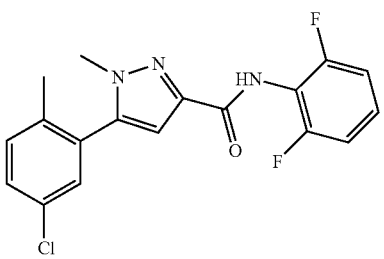 [SMILES: Cc1ccc(Cl)cc1-c1cc(C(=O)Nc2c(F)cccc2F)nn1C]

The title compound of example 26 was prepared in analogy to the preparation of the title compound of example 1 through the reaction of intermediate 23d (168 mg) with 2,6-difluoroaniline (90 mg) (28% yield).

LC-MS (Method 2): m/z [M+H]$^+$=362.1 (MW calc.=361.77); R$_t$=0.81 min.

Synthesis Example 27

5-(2,5-Dimethoxyphenyl)-1-methyl-N-(o-tolyl)-1H-pyrazole-3-carboxylic acid amide

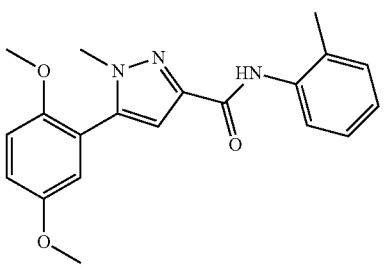 [SMILES: COc1ccc(OC)c(-c2cc(C(=O)Nc3ccccc3C)nn2C)c1]

A solution of intermediate 2c (100 mg) and o-toluidine (39 mg) in dry toluene (2 mL) was treated with trimethyl aluminum (2 M in heptane, 0.18 mL) and was heated to 110° C. for 1 h. The mixture was chilled and 1 M HCl (2 mL) was added. The layers were separated and the aqueous layer was extracted with EtOAc. The combined organic layers were dried and the volatiles were removed under reduced pressure. The residue was purified by column chromatography (Interchim® cartridge 15SiHP/4 g, Cy/EtOAc) to yield the title compound (79% yield).

LC-MS (Method 2): m/z [M+H]$^+$=352.2 (MW calc.=351.40); R$_t$=0.79 min.

Synthesis Example 28

5-(5-Chloro-2-methyl-phenyl)-1-methyl-N-(3-methyl-pyridin-4-yl)-1H-pyrazole-3-carboxylic acid amide

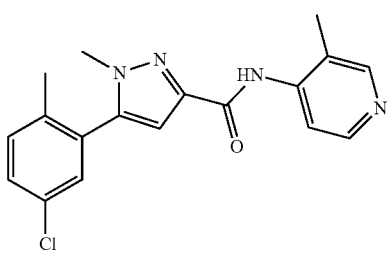 [SMILES: Cc1cnccc1NC(=O)c1cc(-c2cc(Cl)ccc2C)n(C)n1]

To a solution of intermediate 23d (100 mg) in CH$_2$Cl$_2$ (7 mL) were at 0° C. consecutively added N,N-diisopropyl ethylamine (140 μL), 3-methylpyridin-4-amine (40 mg) and bromotripyrrolidino phosphonium hexafluorophosphate (230 mg) and the resulting mixture was stirred at ambient temperature for 2 h. The volatiles were removed under reduced pressure and the residue was purified by column chromatography (Interchim® cartridge 15SiHP/25 g, Cy/EtOAc) to yield the desired compound (84% yield).

LC-MS (Method 2): m/z [M+H]$^+$=341.1 (MW calc.=340.81); R$_t$=0.57 min.

Synthesis Example 29

N-(3-Fluoro-pyridin-4-yl)-1-methyl-5-[2-methyl-5-(trifluoromethyl)-phenyl]-H-pyrazole-3-carboxylic acid amide Intermediate 29a)

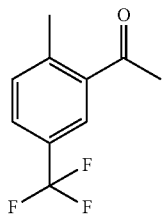

Intermediate 29a was prepared in analogy to the preparation of intermediate 23a starting from 2-methyl-5-(trifluoromethyl)benzonitrile (5.00 g) (75% yield).

Intermediate 29b)

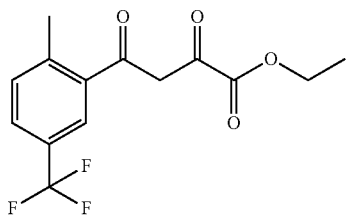 [SMILES: CCOC(=O)C(=O)CC(=O)c1cc(C(F)(F)F)ccc1C]

Intermediate 29b was prepared in analogy to the preparation of intermediate 23b starting from intermediate 29a (2.06 g) (91% yield).

LC-MS (Method 1): m/z [M+H]$^+$=303.2 (MW calc.=302.25); R$_t$=4.0 min.

Intermediate 29c)

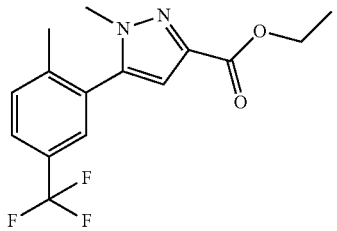 [SMILES: CCOC(=O)c1cc(-c2cc(C(F)(F)F)ccc2C)n(C)n1]

Intermediate 29c was prepared in analogy to the preparation of intermediate 22c through the reaction of intermediate 29b (3.1 g) with methyl hydrazine (793 μL) (18% yield).

LC-MS (Method 1): m/z [M+H]$^+$=313.2 (MW calc.=312.29); R$_t$=3.8 min.

Intermediate 29d)

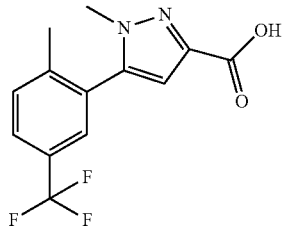 [SMILES: Cc1ccc(C(F)(F)F)cc1-c1cc(C(=O)O)nn1C]

Intermediate 29d was prepared in analogy to the preparation of intermediate 23d starting from intermediate 29c (580 mg) (89% yield).

LC-MS (Method 1): m/z [M+H]$^+$=285.2 (MW calc.=284.23); R$_t$=3.5 min.

N-(3-Fluoro-pyridin-4-yl)-1-methyl-5-[2-methyl-5-(trifluoromethyl)-phenyl]-1H-pyrazole-3-carboxylic acid amide Example 29

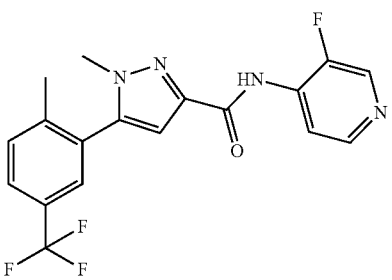 [SMILES: Cc1ccc(C(F)(F)F)cc1-c1cc(C(=O)Nc2ccncc2F)nn1C]

The title compound of example 29 was prepared in analogy to the preparation of the title compound of example 1 through the reaction of intermediate 29d (234 mg) with 3-fluoropyridin-4-amine (102 mg) (67% yield).

LC-MS (Method 2): m/z [M+H]⁺=379.1 (MW calc.=378.32); $R_t$=0.81 min.

Synthesis Example 30

N-(2,6-Difluoro-phenyl)-1-methyl-5-[2-methyl-5-(trifluoromethyl)-phenyl]-1H-pyrazole-3-carboxylic acid amide

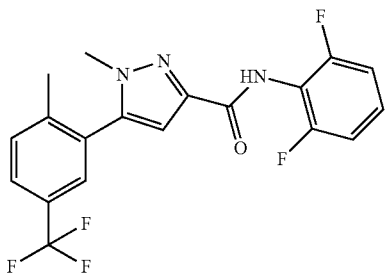 [SMILES: Cc1ccc(C(F)(F)F)cc1-c1cc(C(=O)Nc2c(F)cccc2F)nn1C]

The title compound of example 30 was prepared in analogy to the preparation of the title compound of example 1 through the reaction of intermediate 29d (234 mg) with 2,6-difluoroaniline (91 μL) (46% yield).

LC-MS (Method 2): m/z [M+H]⁺=396.1 (MW calc.=395.33); $R_t$=0.82 min.

Synthesis Example 31

N-(2,6-Difluoro-4-methoxy-phenyl)-5-(2,5-dimethoxyphenyl)-1-methyl-1H-pyrazole-3-carboxylic acid amide

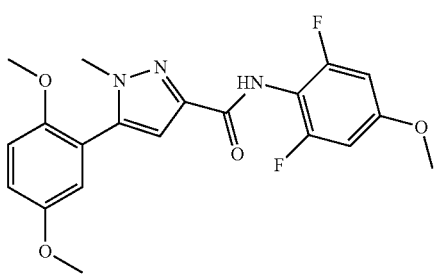 [SMILES: COc1cc(F)c(NC(=O)c2cc(-c3cc(OC)ccc3OC)n(C)n2)c(F)c1]

To a solution of intermediate 2b (72 mg) in dry toluene (2 mL) were consecutively added 2,6-difluoro-4-methoxyaniline (48 mg) and trimethyl aluminium (2 M in heptane, 0.15 mL) and the resulting mixture was heated to 110° C. for 1 h. The mixture was chilled and 1 M HCl (2 mL) was added. The layers were separated and the aqueous layer was extracted with EtOAc. The combined organic layers were dried and the volatiles were removed under reduced pressure. The residue was purified through washing with Et₂O to give the desired compound (86% yield).

LC-MS (Method 2): m/z [M+H]⁺=404.1 (MW calc.=403.38); $R_t$=0.74 min.

Synthesis Example 32

5-(2,5-Dimethoxyphenyl)-N-(2-fluoro-6-methylphenyl)-1-methyl-1H-pyrazole-3-carboxylic acid amide

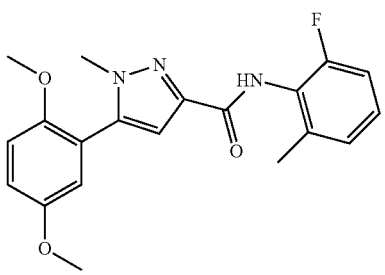 [SMILES: COc1ccc(OC)c(-c2cc(C(=O)Nc3c(C)cccc3F)nn2C)c1]

The title compound of example 32 was prepared in analogy to the preparation of the title compound of example 1 through the reaction of intermediate 2c (100 mg) with 2-fluoro-6-methylaniline (47 mg) (61% yield).

LC-MS (Method 2): m/z [M+H]⁺=370.2 (MW calc.=369.39); $R_t$=0.74 min.

Synthesis Example 33

5-(2,5-Dimethoxyphenyl)-N-(2-fluorophenyl)-1-methyl-1H-pyrazole-3-carboxylic acid amide

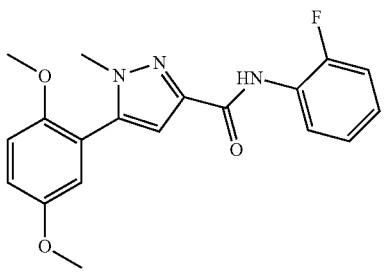 [SMILES: COc1ccc(OC)c(-c2cc(C(=O)Nc3ccccc3F)nn2C)c1]

The title compound of example 33 was prepared in analogy to the preparation of the title compound of example 1 through the reaction of intermediate 2c (100 mg) with 2-fluoroaniline (42 mg) (64% yield).

LC-MS (Method 2): m/z [M+H]⁺=356.1 (MW calc.=355.36); $R_t$=0.80 min.

Synthesis Example 34

N-(3,5-Difluoro-pyridin-4-yl)-5-(2,5-dimethoxyphenyl)-1-methyl-1H-pyrazole-3-carboxylic acid amide

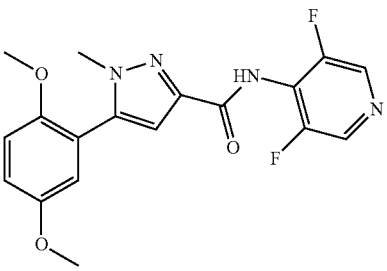 [SMILES: COc1ccc(OC)c(-c2cc(C(=O)Nc3c(F)cncc3F)nn2C)c1]

The title compound of example 34 was prepared in analogy to the preparation of the title compound of example 1 through the reaction of intermediate 2c (100 mg) with 3,5-difluoro-pyridin-4-amine (42 mg) (64% yield).

LC-MS (Method 2): m/z [M+H]$^+$=375.1 (MW calc.=374.34); R$_t$=0.67 min.

Synthesis Example 35

N-(2-Chloro-6-fluoro-phenyl)-5-(2,5-dimethoxyphenyl)-1-methyl-1H-pyrazole-3-carboxylic acid amide

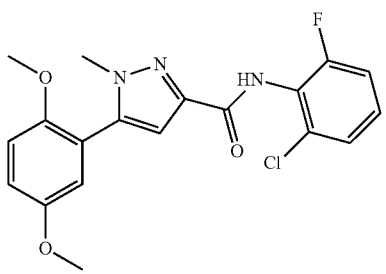 [SMILES: COc1ccc(OC)c(-c2cc(C(=O)Nc3c(F)cccc3Cl)nn2C)c1]

The title compound of example 35 was prepared in analogy to the preparation of the title compound of example 31 through the reaction of intermediate 2b (72 mg) with 2-chloro-6-fluoroaniline (44 mg) (67% yield).

LC-MS (Method 2): m/z [M+H]$^+$=390.1 (MW calc.=389.81); R$_t$=0.76 min.

Synthesis Example 36

5-[2-Chloro-5-(trifluoromethyl)-phenyl]-N-(2,6-difluoro-phenyl)-1-methyl-1H-pyrazole-3-carboxylic acid amide Intermediate 36a)

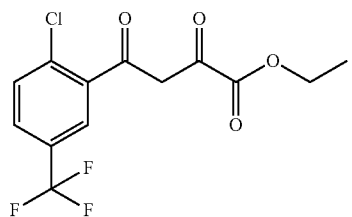

Intermediate 36a was prepared in analogy to the preparation of intermediate 23b starting from 1-(2-chloro-5-(trifluoromethyl)phenyl)ethanone (5.00 g) (99% yield).

Intermediate 36b)

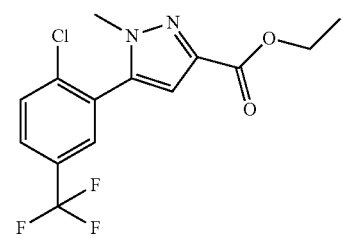 [SMILES: CCOC(=O)c1cc(-c2cc(C(F)(F)F)ccc2Cl)n(C)n1]

A solution of intermediate 36a (3.00 g) in N,N-dimethyl acetamide (37 mL) was treated with concentrated HCl (1.2 mL) and methyl hydrazine (579 μL) and the resulting mixture was stirred at ambient temperature for 18 h. EtOAc was added and the mixture was washed with water. The organic layer was dried and the volatiles were removed under reduced pressure. The residue was purified by column chromatography (Interchim® cartridge 50SiHP/80 g, Cy/EtOAc) to yield the desired compound (55% yield).

LC-MS (Method 1): m/z [M+H]$^+$=333.2 (MW calc.=332.71); R$_t$=3.8 min.

5-[2-Chloro-5-(trifluoromethyl)-phenyl]-N-(2,6-difluoro-phenyl)-1-methyl-1H-pyrazole-3-carboxylic acid amide Example 36

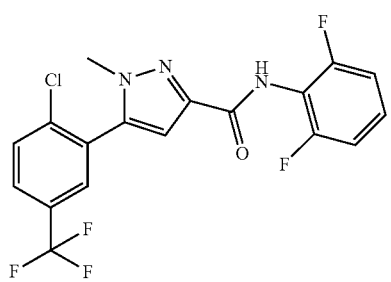 [SMILES: Cn1nc(C(=O)Nc2c(F)cccc2F)cc1-c1cc(C(F)(F)F)ccc1Cl]

The title compound of example 36 was prepared in analogy to the preparation of the title compound of example 31 through the reaction of intermediate 36b (700 mg) with 2,6-difluoroaniline (105 μL) (69% yield).

LC-MS (Method 2): m/z[M+H]$^+$=416.1 (MW calc.=415.74); R$_t$=0.82 min.

Synthesis Example 37

N-(2,6-Difluoro-phenyl)-5-(2,5-dimethoxyphenyl)-1-ethyl-1H-pyrazole-3-carboxylic acid amide Intermediate 37a)

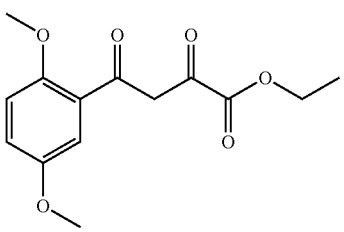 [SMILES: CCOC(=O)C(=O)CC(=O)c1cc(OC)ccc1OC]

Intermediate 37a was prepared in analogy to the preparation of intermediate 23b starting from 1-(2,5-dimethoxyphenyl)ethanone (9.00 g) (99% yield).

Intermediate 37b)

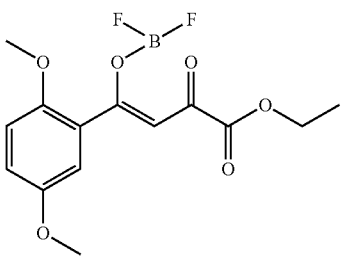 [SMILES: CCOC(=O)C(=O)/C=C(\OB(F)F)c1cc(OC)ccc1OC]

A solution of intermediate 37a (2.00 g) in dry toluene (28 mL) was treated with BF$_3$.Et$_2$O (2.03 g) and the resulting mixture was stirred at ambient temperature for 16 h. The volatiles were removed under reduced pressure and the residue was purified trough washing with Et$_2$O to yield the desired compound (96% yield).
Intermediate 37c)

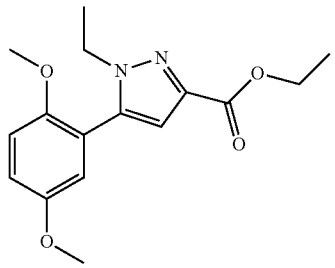 [SMILES: CCOC(=O)c1cc(-c2cc(OC)ccc2OC)n(CC)n1]

A solution of intermediate 37b (1.1 g) in acetonitrile (22 mL) was treated with ethyl hydrazine (726 mg) and the resulting mixture was stirred at ambient temperature for 30 min. The volatiles were removed under reduced pressure and the residue was purified by column chromatography (Interchim® cartridge 50SiHP/40 g, Cy/EtOAc) to yield the desired compound (38% yield).
LC-MS (Method 1): m/z [M+H]$^+$=305.3 (MW calc.=304.34); R$_t$=3.6 min.

N-(2,6-Difluoro-phenyl)-5-(2,5-dimethoxyphenyl)-1-ethyl-1H-pyrazole-3-carboxylic acid amide Example 37

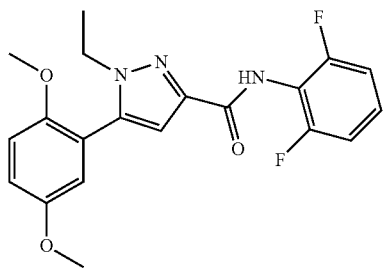 [SMILES: CCn1nc(C(=O)Nc2c(F)cccc2F)cc1-c1cc(OC)ccc1OC]

The title compound of example 37 was prepared in analogy to the preparation of the title compound of example 31 through the reaction of intermediate 37c (100 mg) with 2,6-difluoroaniline (51 mg) (41% yield).
LC-MS (Method 2): m/z [M+H]$^+$=388.1 (MW calc.=387.38); R$_t$=0.77 min.

Synthesis Example 38

5-[2-Cyano-5-(trifluoromethyl)-phenyl]-N-(2,6-difluoro-phenyl)-1-methyl-1H-pyrazole-3-carboxylic acid amide

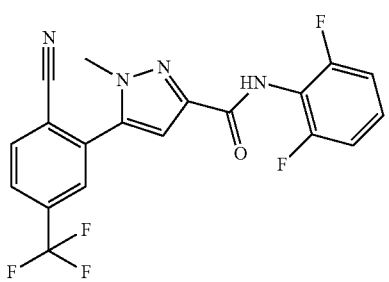 [SMILES: Cn1nc(C(=O)Nc2c(F)cccc2F)cc1-c1cc(C(F)(F)F)ccc1C#N]

A solution of the title compound of example 36 (335 mg), potassium cyanide (54 mg), N,N,N',N'-tetra-methylethylen diamine (24 µL), palladium(II) acetate (3.3 mg) and 1,5-bis (diphenylphosphino)pentane (14 mg) in dry toluene (1.4 mL) was heated to 160° C. for 1 h. Potassium cyanide (54 mg), N,N,N',N'-tetra-methylethylen diamine (24 µL), palladium (II) acetate (3.3 mg) and 1,5-bis(diphenylphosphino)pentane (14 mg) were added again and the mixture was heated to 160° C. for 2 h. The mixture was chilled and diluted with EtOAc. The organic layer was washed with water, was dried and the volatiles were removed under reduced pressure. The residue was purified by column chromatography (Interchim® cartridge 30SiHP/12 g, Cy/EtOAc) to yield the desired compound (64% yield).
LC-MS (Method 2): m/z [M+H]$^+$=407.1 (MW calc.=406.31); R$_t$=0.74 min.

Synthesis Example 39

4-Chloro-N-(2,6-difluoro-phenyl)-5-(2,5-dimethoxyphenyl)-1-methyl-1H-pyrazole-3-carboxylic acid amide Intermediate 39a)

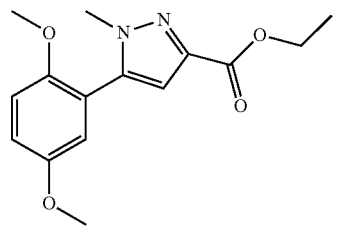 [SMILES: CCOC(=O)c1cc(-c2cc(OC)ccc2OC)n(C)n1]

Intermediate 39a was prepared in analogy to the preparation of intermediate 22c through the reaction of intermediate 37a (1.0 g) with methyl hydrazine (210 µL) (72% yield).
LC-MS (Method 1): m/z [M+H]$^+$=291.2 (MW calc.=290.31); R$_t$=3.5 min.

Intermediate 39b)

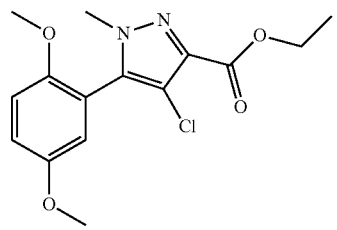 [SMILES: CCOC(=O)c1nn(C)c(-c2cc(OC)ccc2OC)c1Cl]

To a solution of intermediate 39a (747 mg) in dry CH$_2$Cl$_2$ (37 mL) was added sulfuryl chloride (347 mg) and the resulting mixture was stirred at ambient temperature for 1 h. The volatiles were removed under reduced pressure and the residue was purified by column chromatography (Interchim® cartridge 50SiHP/25 g, CH$_2$Cl$_2$/MeOH) to yield the desired compound (74% yield).
LC-MS (Method 1): m/z [M+H]$^+$=325.2 (MW calc.=324.76); R$_t$=3.6 min.

4-Chloro-N-(2,6-difluoro-phenyl)-5-(2,5-dimethoxyphenyl)-1-methyl-1H-pyrazole-3-carboxylic acid amide Example 39

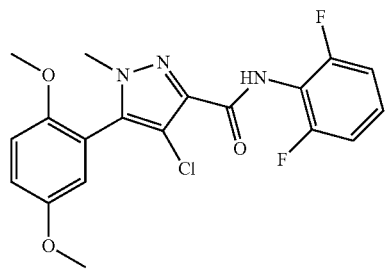 [SMILES: COc1ccc(OC)c(-c2c(Cl)c(C(=O)Nc3c(F)cccc3F)nn2C)c1]

The title compound of example 39 was prepared in analogy to the preparation of the title compound of example 31 through the reaction of intermediate 39b (81 mg) with 2,6-difluoroaniline (39 mg) (81% yield).
LC-MS (Method 2): m/z [M+H]$^+$=408.1 (MW calc.=407.80); $R_t$=0.77 min.

Synthesis Example 40

4-Chloro-5-(2,5-dimethoxyphenyl)-N-(3-fluoro-pyridin-4-yl)-1-methyl-1H-pyrazole-3-carboxylic acid amide Intermediate 40a)

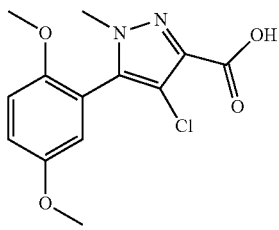 [SMILES: COc1ccc(OC)c(-c2c(Cl)c(C(=O)O)nn2C)c1]

Intermediate 49a was prepared in analogy to the preparation of intermediate 23d starting from intermediate 39b (150 mg) (99% yield).

4-Chloro-5-(2,5-dimethoxyphenyl)-N-(3-fluoro-pyridin-4-yl)-1-methyl-1H-pyrazole-3-carboxylic acid amide Example 40

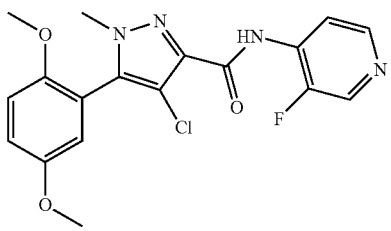 [SMILES: COc1ccc(OC)c(-c2c(Cl)c(C(=O)Nc3ccncc3F)nn2C)c1]

The title compound of example 40 was prepared in analogy to the preparation of the title compound of example 1 through the reaction of intermediate 40a (138 mg) with 3-fluoropyridin-4-amine (93 mg) (79% yield).
LC-MS (Method 2): m/z [M+H]$^+$=391.1 (MW calc.=390.80); $R_t$=0.72 min.

Synthesis Example 41

N-(2,6-Difluoro-phenyl)-5-(2,5-dimethoxyphenyl)-1H-pyrazole-3-carboxylic acid amide Intermediate 41a)

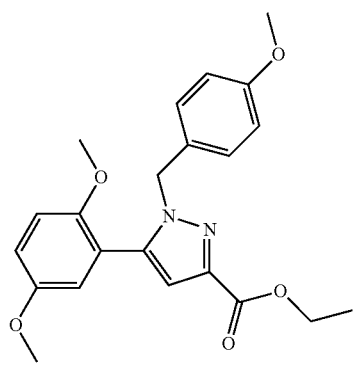 [SMILES: CCOC(=O)c1cc(-c2cc(OC)ccc2OC)n(Cc2ccc(OC)cc2)n1]

To a solution of intermediate 37a (500 mg) in EtOH (7 mL) was added (4-methoxybenzyl)hydrazine dihydrorchloride (675 mg) and the resulting mixture was stirred at ambient temperature for 18 h. The volatiles were removed under reduced pressure and the residue was dissolved in EtOAc. The organic layer was washed with 1 M HCl and with saturated sodium bicarbonate solution, was dried and the volatiles were removed under reduced pressure to yield the desired compound (95% yield)
LC-MS (Method 1): m/z [M+H]$^+$=397.3 (MW calc.=396.44); $R_t$=3.8 min.

Intermediate 41b)

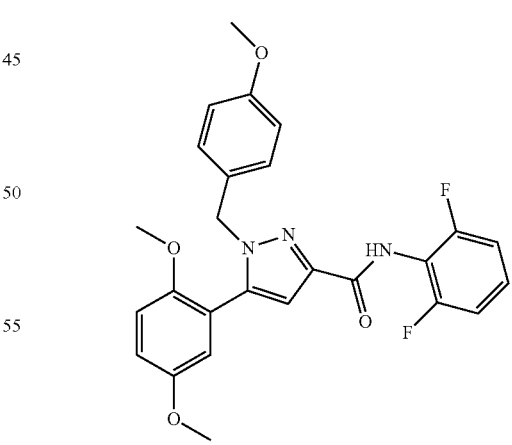

Intermediate 41b was prepared in analogy to the preparation of the title compound of example 31 through the reaction of intermediate 41a (200 mg) with 2,6-difluoroaniline (61 µL) (97% yield).
LC-MS (Method 1): m/z [M+H]$^+$=480.3 (MW calc.=479.48); $R_t$=3.8 min.

N-(2,6-Difluoro-phenyl)-5-(2,5-dimethoxyphenyl)-1H-pyrazole-3-carboxylic acid amide Example 41

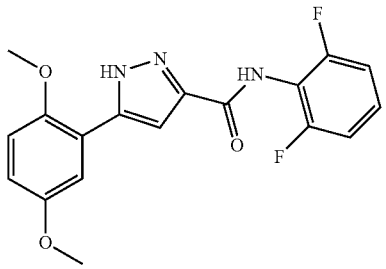 [SMILES: COc1ccc(OC)c(-c2cc(C(=O)Nc3c(F)cccc3F)n[nH]2)c1]

A solution of intermediate 41b (130 mg) in trifluoroacetic acid (1.7 mL) was heated to 60° C. for 3 h. The volatiles were removed under reduced pressure and the residue was purified through washing with Et$_2$O to yield the desired compound (62% yield).
LC-MS (Method 2): m/z [M+H]$^+$=360.1 (MW calc.=359.33); R$_t$=0.67 min.

Synthesis Example 42

N-(2,6-Difluoro-phenyl)-5-(2,5-dimethoxyphenyl)-4-ethyl-1-methyl-1H-pyrazole-3-carboxylic acid amide Intermediate 42a)

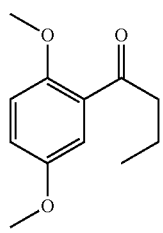

To solution of 2,5-dimethoxybenzonitrile (1.5 g) in dry Et$_2$O (7 mL) was added propyl magnesium chloride (2 M in Et$_2$O, 9.2 mL) and the resulting mixture was heated to 40° C. for 2 h. The mixture was chilled and 4 M HCl (9 mL) was carefully added and it was stirred at ambient temperature for 16 h. The mixture was extracted with EtOAc, the combined organic layers were washed with water, were dried and the volatiles were removed under reduced pressure. The residue was purified by column chromatography (Interchim® cartridge 15SiHP/120 g, Cy/EtOAc) to yield the desired compound (57% yield).
LC-MS (Method 1): m/z [M+H]$^+$=209.3 (MW calc.=208.25); R$_t$=3.5 min.

Intermediate 42b)

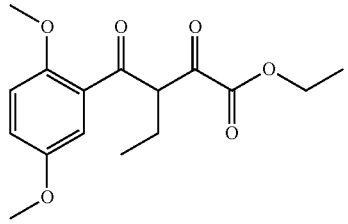 [SMILES: CCOC(=O)C(=O)C(CC)C(=O)c1cc(OC)ccc1OC]

Intermediate 42b was prepared in analogy to the preparation of intermediate 23b starting from intermediate 42a (1.08 g) (34% yield).
LC-MS (Method 1): m/z [M+H]$^+$=307.2 (MW calc.=308.33); R$_t$=3.6 min.

Intermediate 42c)

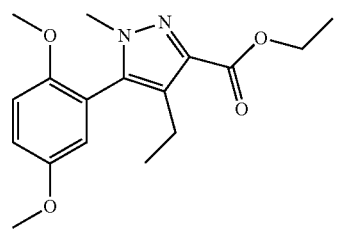 [SMILES: CCOC(=O)c1nn(C)c(-c2cc(OC)ccc2OC)c1CC]

Intermediate 42c was prepared in analogy to the preparation of intermediate 22c through the reaction of intermediate 42b (524 mg) with methyl hydrazine (98 μL) (50% yield).
LC-MS (Method 1): m/z [M+H]$^+$=319.3 (MW calc.=318.37); R$_t$=3.7 min.

N-(2,6-Difluoro-phenyl)-5-(2,5-dimethoxyphenyl)-4-ethyl-1-methyl-1H-pyrazole-3-carboxylic acid amide Example 42

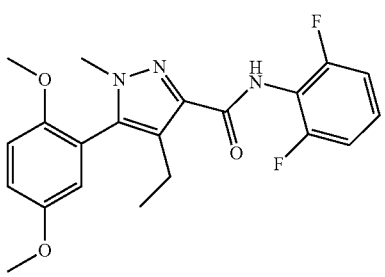 [SMILES: CCc1c(C(=O)Nc2c(F)cccc2F)nn(C)c1-c1cc(OC)ccc1OC]

The title compound of example 42 was prepared in analogy to the preparation of the title compound of example 31 through the reaction of intermediate 42c (80 mg) with 2,6-difluoroaniline (39 mg) (49% yield).
LC-MS (Method 2): m/z [M+H]$^+$=402.2 (MW calc.=401.41); R$_t$=0.82 min.

Synthesis Example 43

N-(2,6-Difluoro-phenyl)-5-(2,5-dimethoxyphenyl)-4-(hydroxylmethyl)-1-methyl-1H-pyrazole-3-carboxylic acid amide Intermediate 43a)

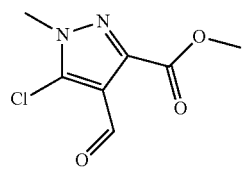

Methyl 5-hydroxy-1-methyl-1H-pyrazole-3-carboxylate (2.0 g) was added at 0° C. to a solution of phosphorus(V) oxychloride (13.7 g) in dry DMF (3 g) and the mixture was heated to 120° C. for 4 h. After cooling to ambient temperature the reaction was quenched by the addition of ice water (100 mL) and the suspension was stirred for 30 min. The precipitated solid formed was isolated through filtration and was washed with water to yield the desired compound (56% yield).

LC-MS (Method 2): m/z [M+H]$^+$=203.2 (MW calc.=202.60); $R_t$=2.3 min.

Intermediate 43b)

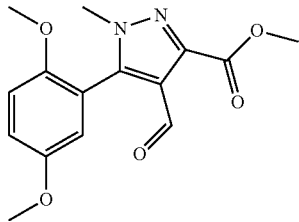 [SMILES: COC(=O)c1nn(C)c(-c2cc(OC)ccc2OC)c1C=O]

A degassed solution of intermediate 43a (1.4 g), 2,5-dimethoxyphenylboronic acid (1.9 g), cesium fluoride (3.1 g) and bis(triphenylphosphine)palladium(II) dichloride (242 mg) in dry dimethoxyethane (100 mL) was stirred under an argon atmosphere at 85° C. for 4 h. The mixture was chilled, filtered and the volatiles were removed under reduced pressure. The residue was purified by column chromatography (Interchim® cartridge 50SiHP/120 g, CH/EtOAc) to yield the desired compound (76% yield).

LC-MS (Method 1): m/z [M+H]$^+$=305.2 (MW calc.=304.30); $R_t$=3.1 min.

Intermediate 43c)

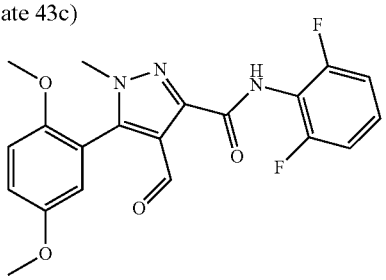

To a solution of intermediate 43b (500 mg) and 2,6-difluoroaniline (354 mg) in dry THF (27 mL) was added lithium bis(trimethylsilyl)amide (1 M in hexane, 2.5 mL) at ambient temperature and the solution was stirred at 60° C. for 2 h. The mixture was chilled and the volatiles were removed under reduced pressure. The residue was purified by column chromatography (Interchim® cartridge 30SiHP/40 g, Cy/EtOAc) to yield the desired compound (64% yield).

LC-MS (Method 1): m/z [M+H]$^+$=402.2 (MW calc.=401.36); $R_t$=3.6 min.

N-(2,6-Difluoro-phenyl)-5-(2,5-dimethoxyphenyl)-4-(hydroxymethyl)-1-methyl-1H-pyrazole-3-carboxylic acid amide Example 43

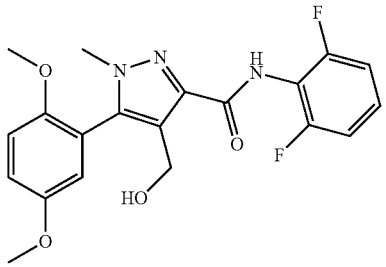 [SMILES: COc1ccc(OC)c(-c2c(CO)c(C(=O)Nc3c(F)cccc3F)nn2C)c1]

To a solution of intermediate 43c (100 mg) in dry MeOH (1 mL) was added sodium borohydrid (11 mg) and the mixture was stirred at ambient temperature for 20 min. The volatiles were removed under reduced pressure and the residue was dissolved in 1 M HCl and was extracted with CH$_2$Cl$_2$. The combined organic layers were dried and the volatiles were removed under reduced pressure to yield the desired compound (75% yield).

LC-MS (Method 2): m/z [M+H]$^+$=404.1 (MW calc.=403.38); $R_t$=0.69 min.

Synthesis Example 44

4-Amino-N-(2,6-difluoro-phenyl)-5-(2,5-dimethoxyphenyl)-1-methyl-1H-pyrazole-3-carboxylic acid amide Intermediate 44a)

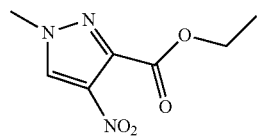

Ammonium nitrate was added to a solution of ethyl 1-methyl-1H-pyrazole-3-carboxylate (460 mg) in trifluoroacetic acid (5 mL) and the mixture was stirred at ambient temperature for 2 h. The volatiles were removed under reduced pressure and the residue was treated with water and was extracted with CH$_2$Cl$_2$. The combined organic layers were dried and the volatiles were removed under reduced pressure. The residue was purified through washing with Et$_2$O to yield the desired compound (90% yield).

LC-MS (Method 1): m/z [M+H]$^+$=200.2 (MW calc.=199.16); $R_t$=2.4 min.

Intermediate 44b)

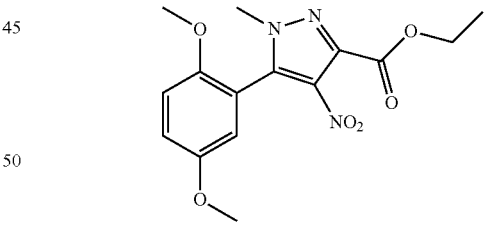

A degassed solution of intermediate 44a (480 mg), 2-bromo-1,4-dimethoxybenzene (1.04 g), palladium acetate (54 mg), di(1-adamantyl)-n-butylphosphine (130 mg) and potassium acetate (490 mg) in N,N-dimethyl acetamide (7 mL) was stirred under an argon atmosphere at 150° C. for 2 h. The volatiles were removed under reduced pressure and the residue was dissolved in water and was extracted with CH$_2$Cl$_2$. The combined organic layers were dried and the volatiles were removed under reduced pressure. The residue was purified by column chromatography (SiO$_2$/50 g, Cy/2-propanol) to yield the desired compound (31% yield).

LC-MS (Method 1): m/z [M+H]$^+$=336.2 (MW calc.=335.31); $R_t$=3.4 min.

Intermediate 44c)

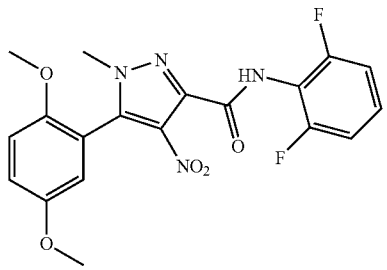 [SMILES: COc1ccc(OC)c(-c2c([N+](=O)[O-])c(C(=O)Nc3c(F)cccc3F)nn2C)c1]

Intermediate 44c was prepared in analogy to the preparation of intermediate 43c through the reaction of intermediate 44b (200 mg) with 2,6-difluoroaniline (110 mg) (92% yield).
LC-MS (Method 1): m/z [M+H]$^+$=419.2 (MW calc.=418.35); R$_t$=3.3 min 4-Amino-N-(2,6-difluoro-phenyl)-5-(2,5-dimethoxyphenyl)-1-methyl-1H-pyrazole-3-carboxylic acid amide Example 44

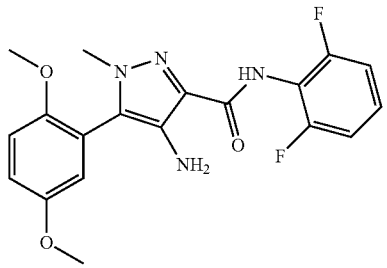 [SMILES: COc1ccc(OC)c(-c2c(N)c(C(=O)Nc3c(F)cccc3F)nn2C)c1]

A mixture of intermediate 44c (210 mg) and 5% palladium on charcoal (110 mg) in MeOH (10 mL) was stirred under a hydrogen atmosphere (1 bar) at ambient temperature for 1 h. The suspension was filtered and the volatiles were removed under reduced pressure. The residue was purified by column chromatography (SiO$_2$/20 g, CH$_2$Cl$_2$/MeOH/NH$_3$) to yield the desired compound (88% yield).
LC-MS (Method 2): m/z [M+H]$^+$=389.2 (MW calc.=388.37); R$_t$=0.68 min.

Synthesis Example 45

5-[2-Cyclopropyl-5-(trifluoromethyloxy)-phenyl]-N-(2,6-difluoro-phenyl)-1-methyl-1H-pyrazole-3-carboxylic acid amide Intermediate 45a)

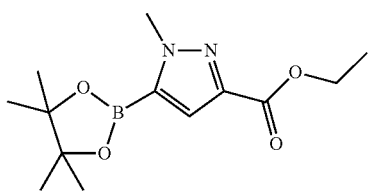 [SMILES: CCOC(=O)c1cc(B2OC(C)(C)C(C)(C)O2)n(C)n1]

4,4'-Di-tert-butyl-2,2'-dipyridyl (194 mg) was added to a solution of (1,5-Cyclooctadiene)(methoxy)-iridium(I) dimer (241 mg) and pinacolborane (4.13 g) in pentane (21 mL) and the mixture was stirred for 20 min at ambient temperature. Then a solution of 1-methyl-1H-pyrazole-3-carboxylate (3.05 g) in pentane (14 mL) and THF (7 mL) was added and the solution was stirred at ambient temperature for 3 d. The volatiles were removed under reduced pressure and the residue was purified by chromatography (SiO$_2$, methylene chloride/methanol) to yield the desired product (78% yield).

Intermediate 45b)

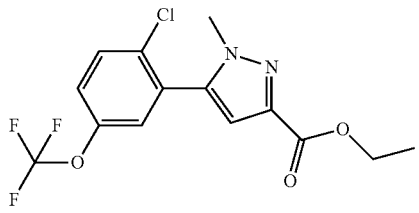 [SMILES: CCOC(=O)c1cc(-c2cc(OC(F)(F)F)ccc2Cl)n(C)n1]

A degassed solution of intermediate 45a (900 mg), 2-bromo-1-chloro-4-(trifluoromethoxy)benzene (885 mg), lithium hydroxide (83 mg) and bis(tri-tert-butylphosphine)palladium(0) (84 mg) in dry DMF was stirred under an argon atmosphere at 90° C. for 30 min. The volatiles were removed under reduced pressure and the residue was purified by column chromatography (Interchim® cartridge 50SiHP/80 g, Cy/EtOAc) to yield the desired compound (72% yield).
LC-MS (Method 1): m/z [M+H]$^+$=349.2 (MW calc.=348.70); R$_t$=3.9 min.

Intermediate 45c)

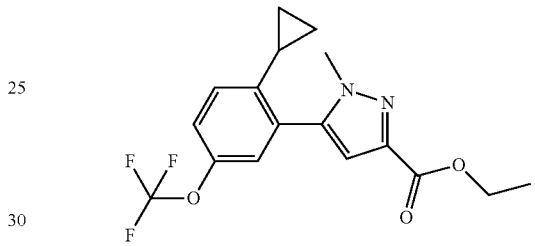

A degassed solution of intermediate 45b (580 mg), potassium cyclopropyl trifluoroborate (379 mg), palladium acetate (37 m), di(1-adamantyl)-n-butylphosphine (119 mg) and cesium carbonate in toluene (12 mL) and water (5 mL) was stirred at 100° C. for 16 h. The mixture was chilled and the layers were separated. The aqueous layer was extracted with EtOAc and the combined organic layers were dried and the volatiles were removed under reduced pressure. The residue was purified by column chromatography (Interchim® cartridge 30SiHP/40 g, Cy/EtOAc) to yield the desired compound (61% yield).
LC-MS (Method 1): m/z [M+H]$^+$=355.2 (MW calc.=354.32); R$_t$=4.0 min.

5-[2-Cyclopropyl-5-(trifluoromethyloxy)-phenyl]-N-(2,6-difluoro-phenyl)-1-methyl-1H-pyrazole-3-carboxylic acid amide Example 45

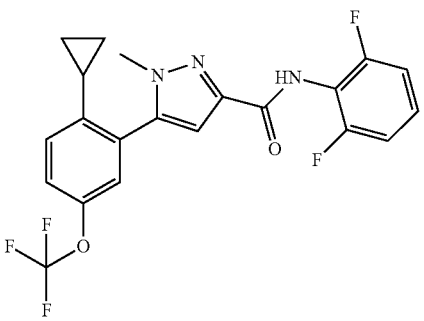 [SMILES: Cn1nc(C(=O)Nc2c(F)cccc2F)cc1-c1cc(OC(F)(F)F)ccc1C1CC1]

The title compound of example 45 was prepared in analogy to the preparation of intermediate 43c through the reaction of intermediate 45c (115 mg) with 2,6-difluoroaniline (54 mg) (80% yield).

LC-MS (Method 2): m/z [M+H]⁺=438.1 (MW calc.=437.36); $R_t$=0.90 min.

Synthesis Example 46

5-[2-Cyclopropyl-5-(trifluoromethyloxy)-phenyl]-N-(3,5-difluoro-pyridin-4-yl)-1-methyl-1H-pyrazole-3-carboxylic acid amide

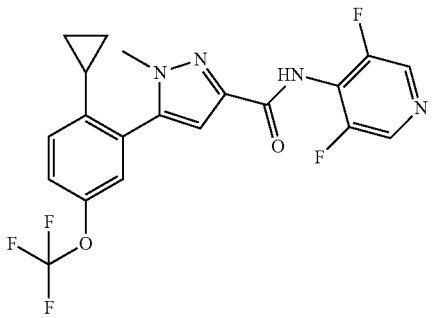 [SMILES: Cn1nc(C(=O)Nc2c(F)cncc2F)cc1-c1cc(OC(F)(F)F)ccc1C1CC1]

The title compound of example 46 was prepared in analogy to the preparation of intermediate 43c through the reaction of intermediate 45c (115 mg) with 3,5-difluoropyridin-4-amine (55 mg) (79% yield).
LC-MS (Method 2): m/z [M+H]⁺=439.1 (MW calc.=438.35); $R_t$=0.86 min.

Synthesis Example 47

5-[2-Cyclopropyl-5-(trifluoromethyloxy)-phenyl]-N-(3-fluoro-pyridin-4-yl)-1-methyl-1H-pyrazole-3-carboxylic acid amide

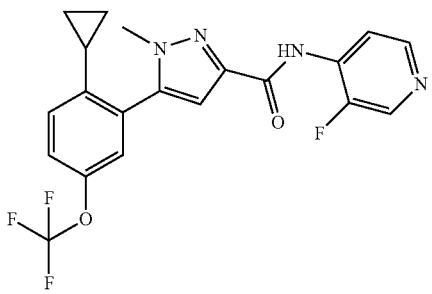 [SMILES: Cn1nc(C(=O)Nc2ccncc2F)cc1-c1cc(OC(F)(F)F)ccc1C1CC1]

The title compound of example 47 was prepared in analogy to the preparation of intermediate 43c through the reaction of intermediate 45c (115 mg) with 3-fluoropyridin-4-amine (55 mg) (84% yield).
LC-MS (Method 2): m/z [M+H]⁺=421.1 (MW calc.=420.36); $R_t$=0.90 min.

Synthesis Example 48

4-Amino-5-(2,5-dimethoxyphenyl)-N-(3-fluoro-pyridin-4-yl)-1-methyl-1H-pyrazole-3-carboxylic acid amide Intermediate 48a)

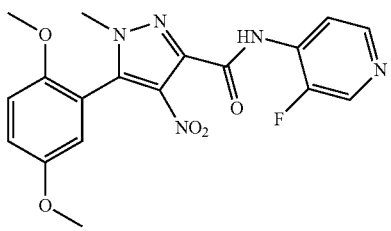 [SMILES: COc1ccc(OC)c(-c2c(N)c(C(=O)Nc3ccncc3F)nn2C)c1]

Intermediate 48a was prepared in analogy to the preparation of intermediate 43c through the reaction of intermediate 44b (490 mg) with 3-fluoropyridin-4-amine (213 mg) (58% yield).
LC-MS (Method 1): m/z [M+H]⁺=402.2 (MW calc.=401.35); $R_t$=3.3 min 4-Amino-5-(2,5-dimethoxyphenyl)-N-(3-fluoro-pyridin-4-yl)-1-methyl-1H-pyrazole-3-carboxylic acid amide Example 48

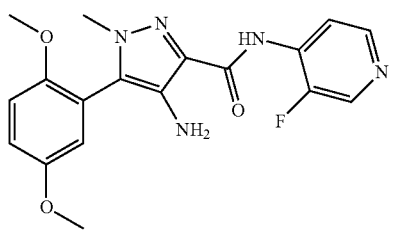

A solution of intermediate 48a (300 mg) in MeOH (8 mL) was treated with acetic acid (0.7 mL) and zinc (393 mg) and the mixture was stirred at ambient temperature for 20 h. The suspension was filtered and the volatiles were removed under reduced pressure. The residue was treated with saturated sodium bicarbonate solution and was extracted with EtOAc. The combined organic layers were dried and the volatiles were removed under reduced pressure. The residue was purified by column chromatography (Interchim® cartridge 30SiHP/25 g, CH₂Cl₂/MeOH) to yield the desired compound (68% yield).
LC-MS (Method 2): m/z [M+H]⁺=372.1 (MW calc.=371.37); $R_t$=0.61 min.

Synthesis Example 66

N-(2,6-Difluoro-phenyl)-5-(2-methoxy-4-methylsulfonyl-phenyl)-1-methyl-1H-pyrazole-3-carboxylic acid amide Intermediate 66a)

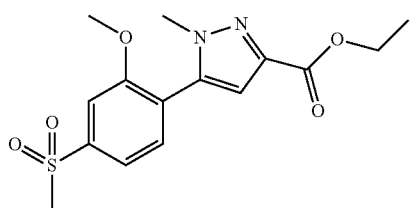 [SMILES: CCOC(=O)c1cc(-c2ccc(S(C)(=O)=O)cc2OC)n(C)n1]

Intermediate 66a was prepared in analogy to the preparation of intermediate 45b through the reaction of intermediate 45a (234 mg) with 1-bromo-2-methoxy-4-(methylsulfonyl)-benzene (200 mg) at 110° C. for 2 h (80% yield).
LC-MS (Method 2): m/z [M+H]⁺=339.2 (MW calc.=338.1); $R_t$=0.7 min (N-(2,6-Difluoro-phenyl)-5-(2-methoxy-4-methyl-sulfonyl-phenyl)-1-methyl-1H-pyrazole-3-carboxylic acid amide Example 66

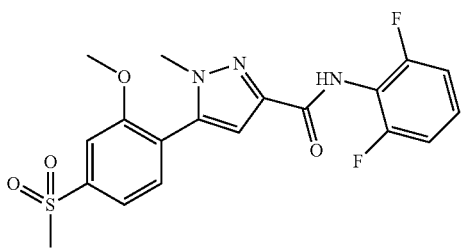 [SMILES: COc1cc(S(C)(=O)=O)ccc1-c1cc(C(=O)Nc2c(F)cccc2F)nn1C]

The title compound was prepared in analogy to the preparation of intermediate 43c through the reaction of intermediate 66a (100 mg) with 2,6-difluoroaniline (56 mg) (32% yield).

LC-MS (Method 2): m/z [M+H]$^+$=422.1 (MW calc.=421.09); R$_t$=0.64 min.

Synthesis Example 67

N-(3,5-Difluoro-pyridin-4-yl)-5-(2,5-dimethoxyphenyl)-1-methyl-4-methylamino-1H-pyrazole-3-carboxylic acid amide Intermediate 67a)

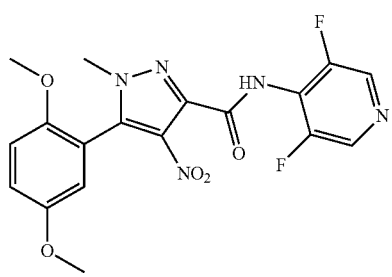 [SMILES: COc1ccc(OC)c(-c2c([N+](=O)[O-])c(C(=O)Nc3c(F)cncc3F)nn2C)c1]

Intermediate 67a was prepared in analogy to the preparation of intermediate 43c through the reaction of intermediate 44b (362 mg) with 4-amino-3,5-difluoropyridine (182 mg) (55% yield).

Intermediate 67b)

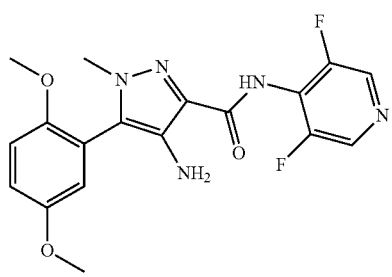

Intermediate 67b was prepared in analogy to the preparation of example 44 through the reaction of intermediate 67a (247 mg) (94% yield).

Intermediate 67c)

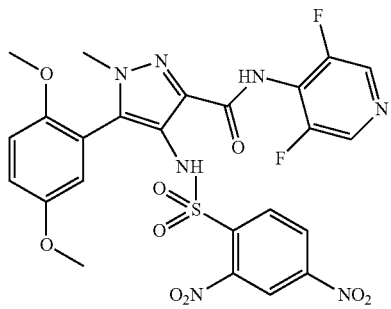 [SMILES: COc1ccc(OC)c(-c2c(NS(=O)(=O)c3ccc([N+](=O)[O-])cc3[N+](=O)[O-])c(C(=O)Nc3c(F)cncc3F)nn2C)c1]

To a solution of intermediate 67b (215 mg) and triethylamine (115 μL) in dry CH$_2$Cl$_2$ was added 2,4-dinitrobenzolsulfonylchloride (176 mg) and the mixture stirred for 24 h at ambient temperature followed by addition of further triethylamine (60 μL) and 2,4-dinitrobenzolsulfonylchloride (88 mg) and continued stirring for 6 h. Saturated NaHCO$_3$ solution was added, the organic layer separated and the aqueous layer extracted twice with CH$_2$Cl$_2$. The combined organic layers were dried and the volatiles were removed under reduced pressure. The residue was purified by column chromatography (SiO$_2$, Cy/EtOAc) to yield the desired compound (43% yield).

N-(3,5-Difluoro-pyridin-4-yl)-5-(2,5-dimethoxyphenyl)-1-methyl-4-methylamino-1H-pyrazole-3-carboxylic acid amide Example 67

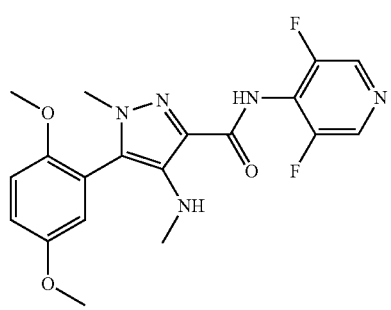 [SMILES: CNc1c(C(=O)Nc2c(F)cncc2F)nn(C)c1-c1cc(OC)ccc1OC]

To a solution of intermediate 67c (148 mg), MeOH (97 μL) and triphenylphosphine (125 mg) in dry CH$_2$Cl$_2$ was added diisopropyl azodicarboxylate (94 μL) and the mixture was stirred for 1 h at 0° C. After addition of isopropylamine (498 μL) stirring was continued for 20 h at ambient temperature. Volatiles were removed under reduced pressure and the residue was purified by column chromatography (SiO$_2$/Cy/EtOAc) followed by HPLC purification (250×30 mm, 5μ Phenylhexyl/35% MeCN, 65% H$_2$O, 0.1% TFA) to yield the title compound (39% yield).

LC-MS (Method 2): m/z [M+H]$^+$=404.1 (MW calc.=403.15); R$_t$=0.67 min.

Examples 49 to 65 were synthesized in a library setup trough amide coupling reactions between 3 carboxylic acid building blocks (BB-I, BB-II, BB-III) and commercially available amines. The structures and analytical data of these examples are displayed in table 1.

Building Block Syntheses

BB-I: 5-(2-fluoro-6-(trifluoromethyl)phenyl)-1-methyl-1H-pyrazole-3-carboxylic acid Intermediate-BB-Ia)

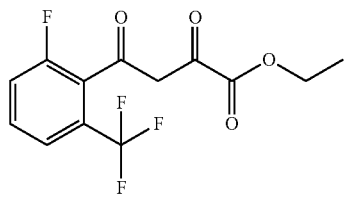 [SMILES: CCOC(=O)C(=O)CC(=O)c1c(F)cccc1C(F)(F)F]

Intermediate-BB-Ia was prepared in analogy to the preparation of intermediate 23b starting from 1-(2-fluoro-6-(trifluoromethyl)phenyl)ethanone (20 g) (99% yield).
Intermediate-BB-Ib)

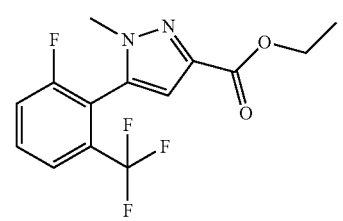 [SMILES: CCOC(=O)c1cc(-c2c(F)cccc2C(F)(F)F)n(C)n1]

Intermediate-BB-Ib was prepared in analogy to the preparation of intermediate 22c through the reaction of Intermediate-BB-Ia (29.7 g) with methyl hydrazine sulfate (16.7 g) (43% yield).

5-(2-fluoro-6-(trifluoromethyl)phenyl)-1-methyl-1H-pyrazole-3-carboxylic acid (BB-I)

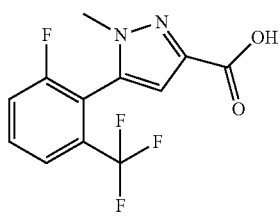 [SMILES: Cn1nc(C(=O)O)cc1-c1c(F)cccc1C(F)(F)F]

BB-I was prepared in analogy to the preparation of intermediate 23d starting from Intermediate-BB-Ib (29.7 g) (74% yield).

BB-II: 5-(2,6-difluorophenyl)-1-methyl-1H-pyrazole-3-carboxylic acid

Intermediate-BB-IIa)

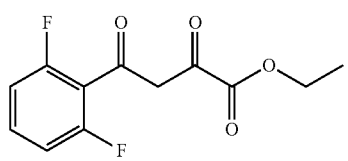 [SMILES: CCOC(=O)C(=O)CC(=O)c1c(F)cccc1F]

Intermediate-BB-IIa was prepared in analogy to the preparation of intermediate 23b starting from 1-(2,6-difluorophenyl)ethanone (20 g) (99% yield).
Intermediate-BB-IIb)

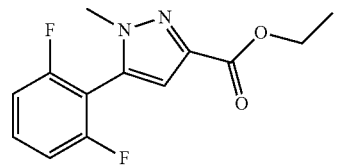 [SMILES: CCOC(=O)c1cc(-c2c(F)cccc2F)n(C)n1]

Intermediate-BB-IIb was prepared in analogy to the preparation of intermediate 22c through the reaction of Intermediate-BB-IIa (32.0 g) with methyl hydrazine sulfate (22.2 g) (32% yield).

5-(2,6-difluorophenyl)-1-methyl-1H-pyrazole-3-carboxylic acid (BB-II)

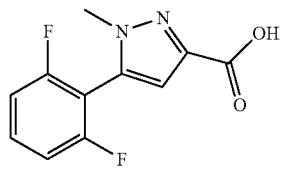 [SMILES: Cn1nc(C(=O)O)cc1-c1c(F)cccc1F]

BB-II was prepared in analogy to the preparation of intermediate 23d starting from Intermediate-BB-IIb (4.0 g) (70% yield).

BB-III: 1-methyl-5-(4-methylpyridin-3-yl)-1H-pyrazole-3-carboxylic acid

Intermediate-BB-IIIa)

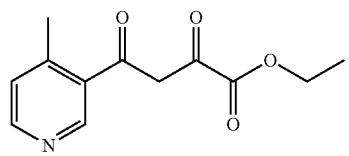 [SMILES: CCOC(=O)C(=O)CC(=O)c1cnccc1C]

Intermediate-BB-IIIa was prepared in analogy to the preparation of intermediate 23b starting from 1-(4-methylpyridin-3-yl)ethanone (10 g) (40% yield).
Intermediate-BB-IIIb)

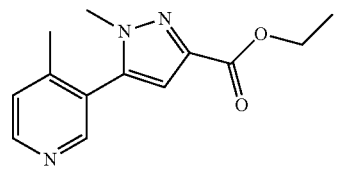 [SMILES: CCOC(=O)c1cc(-c2cnccc2C)n(C)n1]

Intermediate-BB-IIIb was prepared in analogy to the preparation of intermediate 22c through the reaction of Intermediate-BB-IIIa (7.0 g) with methyl hydrazine sulfate (4.2 g) (15% yield).

1-methyl-5-(4-methylpyridin-3-yl)-1H-pyrazole-3-carboxylic acid (BB-III)

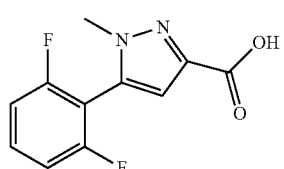

BB-III was prepared in analogy to the preparation of intermediate 23d starting from Intermediate-BB-IIIb (3.4 g) (45% yield).

Library Procedures:

Acid Chloride Method:

To a solution of BB-I-III (1 eq) in $CH_2Cl_2$, oxalyl chloride (1.1 eq) and DMF (cat.) were added and stirred at room temperature for 1 h. After completed formation of the acid chloride (1-2 h), the excess reagent and solvent were evacuated, the residue diluted in dry $CH_2Cl_2$ and this solution was added dropwise at 0° C. to a solution of $NEt_3$ (2 eq) and the respective amine (1 eq) in $CH_2Cl_2$. The reaction mixture stirred at room temperature overnight. The reaction mixture was quenched with sat. sodium bicarbonate solution (3 mL), extracted with $CH_2Cl_2$ and the combined organic layers were washed with brine, dried and concentrated under reduced pressure to give a residue that was purified by preparative thin layer chromatography (silica gel G-G254; with respective solvent system) to give the desired compounds.

EDC.HCl, HOBT method:

To a suspension of BB-I-III (1 eq) in $CH_2Cl_2$ N,N-diisopropylethylamine (3 eq) was added and the reaction mixture was stirred for 10 min. EDC.HCl (1.5 eq), HOBT (1.2 eq) were added and the reaction mixture was stirred for 10 min. Then the respective amine (1.2 eq) was added and the reaction mixture was stirred at room temperature overnight. The reaction mixture was diluted with water (3 mL), extracted with $CH_2Cl_2$ and the combined organic layers were washed with brine, dried and concentrated under reduced pressure to give a residue that was purified by preparative thin layer chromatography (silica gel G-G254; with respective solvent system) to give the desired compounds.

HATU Method:

To a suspension of acid BB-I-III (1 eq) in $CH_2Cl_2$, N,N-diisopropylethylamine (3 eq) was added and reaction mixture stirred for 10 min. HATU (1.5 eq), was added and the reaction mixture was stirred for 10 min. Then the respective amine (1 eq) was added and the reaction mixture stirred at room temperature overnight. The reaction mixture was diluted with water (3 mL), extracted with $CH_2Cl_2$ and the combined organic layers were washed with brine, dried and concentrated under reduced pressure to give a residue that was purified by preparative thin layer chromatography (silica gel G-G254; with respective solvent system) to give the target compounds.

TABLE 1

| Example Nr. | $A_1$ | $A_2$ | Name | [M + H]+ (found) | MW (calc.) | $t_R$ (min) |
| --- | --- | --- | --- | --- | --- | --- |
| 49 | 2-F, 6-CF3-phenyl | 3,5-difluoro-pyridin-4-yl | N-(3,5-Difluoro-pyridin-4-yl)-5-[2-fluoro-6-(trifluoromethyl)-phenyl]-1-methyl-1H-pyrazole-3-carboxylic acid amide | 401.1 | 400.28 | 0.68 |
| 50 | 2,6-difluoro-phenyl | 2,6-difluoro-phenyl | N,5-Bis(2,6-difluoro-phenyl)-1-methyl-1H-pyrazole-3-carboxylic acid amide | 350.1 | 349.28 | 0.74 |
| 51 | 2-F, 6-CF3-phenyl | 2,6-difluoro-phenyl | N-(2,6-Difluoro-phenyl)-5-[2-fluoro-6-(trifluoromethyl)-phenyl]-1-methyl-1H-pyrazole-3-carboxylic acid amide | 400.0 | 399.29 | 0.78 |
| 52 | 2,6-difluoro-phenyl | 2-chloro-6-methyl-phenyl | N-(2-Chloro-6-methyl-phenyl)-5-(2,6-difluoro-phenyl)-1-methyl-1H-pyrazole-3-carboxylic acid amide | 362.1 | 361.77 | 0.79 |
| 53 | 2,6-difluoro-phenyl | 3-fluoro-5-methyl-pyridin-4-yl | 5-(2,6-Difluoro-phenyl)-N-(3-fluoro-5-methyl-pyridin-4-yl)-1-methyl-1H-pyrazole-3-carboxylic acid amide | 347.2 | 346.31 | 0.63 |

TABLE 1-continued

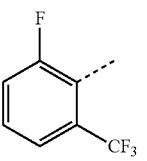

| Example Nr. | A₁ | A₂ | Name | [M + H]⁺ (found) | MW (calc.) | $t_R$ (min) |
|---|---|---|---|---|---|---|
| | | | | HPLC-MS (method 2) | | |
| 54 | 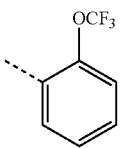 | 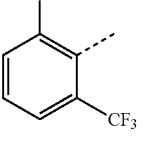 | 5-[2-Fluoro-6-(trifluoromethyl)-phenyl]-1-methyl-N-[2-(trifluoro-methyloxy)-phenyl]-1H-pyrazole-3-carboxylic acid amide | 448.2 | 447.31 | 0.87 |
| 55 | 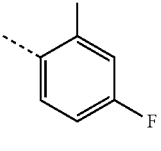 | 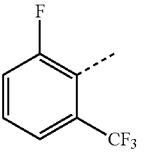 | N-(2,4-Difluoro-phenyl)-5-[2-fluoro-6-(trifluoromethyl)-phenyl]-1-methyl-1H-pyrazole-3-carboxylic acid amide | 400.2 | 399.29 | 0.80 |
| 56 | 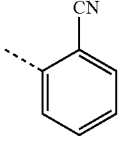 | 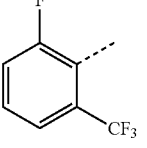 | N-(2-Cyano-phenyl)-5-[2-fluoro-6-(trifluoromethyl)-phenyl]-1-methyl-1H-pyrazole-3-carboxylic acid amide | 389.2 | 388.32 | 0.77 |
| 57 | 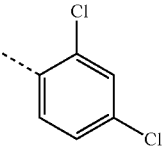 | 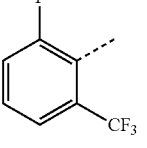 | N-(2,4-Dichlorophenyl)-5-[2-fluoro-6-(trifluoromethyl)-phenyl]-1-methyl-1H-pyrazole-3-carboxylic acid amide | 432.1 | 432.20 | 0.92 |
| 58 | 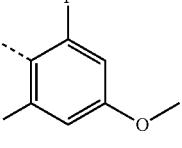 | 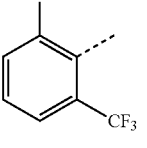 | N-(2,6-Difluoro-4-methoxy-phenyl)-5-[2-fluoro-6-(trifluoro-methyl)-phenyl]-1-methyl-1H-pyrazole-3-carboxylic acid amide | 430.2 | 429.32 | 0.75 |
| 59 | 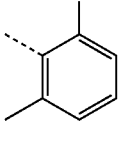 | 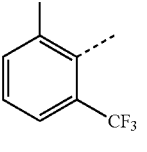 | N-(2-Fluoro-6-methyl-phenyl)-5-[2-fluoro-6-(trifluoromethyl)-phenyl]-1-methyl-1H-pyrazole-3-carboxylic acid amide | 396.2 | 395.33 | 0.75 |
| 60 | 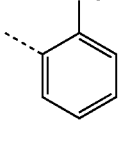 | 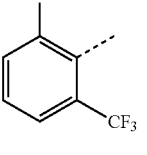 | 5-[2-Fluoro-6-(trifluoromethyl)-phenyl]-1-methyl-N-[2-(trifluoro-methyl)-phenyl]-1H-pyrazole-3-carboxylic acid amide | 432.1 | 431.31 | 0.85 |
| 61 | 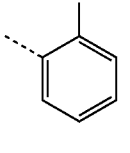 | | N-(2-Fluorophenyl)-5-[2-fluoro-6-(trifluoromethyl)phenyl]-1-methyl-1H-pyrazole-3-carboxylic acid amide | 382.1 | 381.30 | 0.80 |

TABLE 1-continued

| Example Nr. | A₁ | A₂ | Name | [M + H]⁺ (found) | MW (calc.) | $t_R$ (min) |
|---|---|---|---|---|---|---|
| 62 | 2-F, 6-CF₃-phenyl | 3-F-pyridin-4-yl | N-(3-Fluoro-pyridin-4-yl)-5-[2-fluoro-6-(trifluoromethyl)-phenyl]-1-methyl-1H-pyrazole-3-carboxylic acid amide | 383.1 | 382.29 | 0.70 |
| 63 | 2-F, 6-CF₃-phenyl | 3-F-5-methyl-pyridin-4-yl | N-(3-Fluoro-5-methyl-pyridin-4-yl)-5-[2-fluoro-6-(trifluoromethyl)-phenyl]-1-methyl-1H-pyrazole-3-carboxylic acid amide | 397.2 | 396.31 | 0.68 |
| 64 | 4-methyl-pyridin-3-yl | 2-(trifluoromethyl)-phenyl | 1-Methyl-5-(4-methyl-pyridin-3-yl)-N-[2-(trifluoromethyl)-phenyl]-1H-pyrazole-3-carboxylic acid amide | 361.1 | 360.33 | 0.64 |
| 65 | 4-methyl-pyridin-3-yl | 3-F-5-methyl-pyridin-4-yl | N-(3-Fluoro-5-methyl-pyridin-4-yl)-1-methyl-5-(4-methyl-pyridin-3-yl)-1H-pyrazole-3-carboxylic acid amide | 326.2 | 325.34 | 0.41 |

Pharmacological Methods

Compounds of the invention have been tested for their effects on CRAC channels according to the following or similar procedures.

HEK Calcium Influx Assay

The effect of compounds of the invention on intracellular [$Ca^{2+}$] was tested in the HEK293 cell line (ECACC).

HEK293 cells were cultured in DMEM/F12/Glutamax (Gibco) containing 10% FCS (Gibco), and maintained at 37° C., 5% $CO_2$. Cell were split twice a week [3*10⁶ (Mon-Thu) and 1*10⁶ (Thu-Mon) cells/50 ml medium in T-175 ZK culture flasks, respectively]. Twenty four hours pre-experiment, cells were seeded on 96 well plates (Poly-D-Lysine 96well Black/Clear Plate, BD Biocoat REF 356640) at a density of 40,000 cells/well in DMEM/F12 (Gibco) containing 10% FCS (Gibco), and maintained at 37° C., 5% $CO_2$.

Prior to store-depletion, cell culture medium was removed and cells were loaded with the a Calcium-sensitive fluorescent dye comprised within the Calcium-4-assay kit (Molecular Devices) in nominally $Ca^{2+}$-free HBS buffer (140 mM NaCl, 4 mM KCl, 0.2 mM $MgCl_2$, 11 mM D-glucose, and 10 mM HEPES, pH 7.4) according to manufacturer's instruction for 60 min at 37° C., 5% $CO_2$.

Passive depletion of intracellular $Ca^{2+}$-stores was then triggered by employing the SERCA inhibitor thapsigargin (2 μM final) for 10 min in the dark (RT). To prevent immediate $Ca^{2+}$-entry via the activated Store-operated channels (SOCs), cells were maintained in $Ca^{2+}$-free HBS buffer comprising 100 μM EGTA during store-depletion.

Intracellular changes in [$Ca^{2+}$] were subsequently monitored with the FLIPR device (Molecular Devices). In brief, baseline imaging post-store depletion was allowed for 1 min before adjusting the extracellular buffer to 3 mM $CaCl_2$. Increases in intracellular [$Ca^{2+}$] due to pre-activated SOC channels were monitored for 15 min until intracellular $Ca^{2+}$ levels had declined into a steady-state. Finally, compounds were administered and $Ca^{2+}$ signals were recorded for additional 10 min.

Inhibition of endogenous SOC in HEK293 cells was quantified employing the average $Ca^{2+}$ signal measured from 9.5-10 min post-administration. Zero percent inhibition (MAX) was defined as the $Ca^{2+}$ signal recorded from wells to which DMSO-only had been added instead of compound. Hundred percent inhibition (MIN) was defined as the signal obtained from wells in which cells haven't been treated with TG prior to $Ca^{2+}$ addition and to which DMSO-only had been added instead of compound. For routine IC50 determinations of compounds, 8 concentrations of a serial dilution (1:3.16) were tested, starting off from 10 μM. Reliable IC50's could consequently be determined only, if they were at least sub 2.5-3 μM.

Jurkat IL-2 Production Assay

The effect of compounds of the invention on Interleukin-2 (IL-2) production/release was tested in the Jurkat T cell line (ECACC) clone E6-1.

Jurkat T cells were cultured in DMEM/F12/Glutamax (Gibco) containing 10% FCS (Gibco), and maintained at 37° C., 5% $CO_2$. Cell were split twice a week [5*10⁶ (Mon-Thu) and 1*10⁷ (Thu-Mon) cells/50 ml medium in T-175 ZK culture flasks, respectively].

Prior to experiment, cells were seeded on 96 well plates (Cellstar 96 Well; Cat No. 655180, Greiner bio-one) at a density of $5*10^5$ cells/well in DMEM/F12/Glutamax (Gibco) containing 10% FCS (Gibco), and incubated for 60 min at 37° C., 5% $CO_2$. Subsequently, compounds were added and cells were allowed to incubate for 30 min at 37° C., 5% $CO_2$. Cells were then stimulated with 15 μg/ml Phytohemagglutinin (PHA; Sigma) for 22 hours at 37° C., 5% $CO_2$.

Before sampling of the supernatants, cells were spun down (200*g/5 min/RT). The amount of IL-2 released into the supernatant was quantified with the human IL-2 AlphaLisa kit (Perkin Elmer) according to manufacturer's instructions. Luminescence proximity measurements were carried out in the Synergy H4 reader (BioTek) employing the fluorescence setting of the reader (ex: 680/30 nm; em: 620/40 nm). Inhibition of IL-Production/Release in/from Jurkat T Cells was Quantified as Follows:

Zero percent inhibition (MAX) was defined as the [IL-2] determined in supernatants derived from cells to which PHA & DMSO-only had been added instead of compound. Hundred percent inhibition (MIN) was defined as the [IL-2] determined in supernatants derived from cells that had been pre-treated with 1 μM CyclosporineA (Sigma) before the addition of 15 μg/ml PHA.

For routine IC50 determinations of compounds, 8 concentrations of a serial dilution (1:3.16) were tested, starting off from 10 μM.

TABLE 2

Exemplary compounds of the invention exhibit inhibition of the CRAC channel and inhibition of the IL-2 production in these assays within the following ranges: $IC_{50}$ values from <0.5 μM (A); 0.5-1.0 μM (B); >1.0-5.0 μM (C) and full $IC_{50}$ not determined (n.d.). or % inhibition @ 10 μM < 50 (C), 50-70 (B), >70 (A).

| Example No. | % inhib.[@ 10 μM] FLIPR | $IC_{50}$ [μM] IL-2 |
|---|---|---|
| 1 | A | C |
| 2 | A | C |
| 3 | C | C |
| 4 | A | B |
| 5 | B | — |
| 6 | A | n.d. |
| 7 | A | B |
| 8 | A | A |
| 9 | A | C |
| 10 | A | B |
| 11 | B | n.d. |
| 12 | A | B |
| 13 | B | n.d. |
| 14 | B | n.d. |
| 15 | B | C |
| 16 | A | C |
| 17 | B | C |
| 18 | C | C |
| 19 | A | n.d. |
| 20 | A | B |
| 21 | A | A |
| 22 | B | n.d. |
| 23 | B | n.d. |
| 24 | A | n.d. |
| 25 | A | B |
| 26 | A | C |
| 27 | A | C |
| 28 | B | n.d. |
| 29 | B | n.d. |
| 30 | A | B |
| 31 | A | A |
| 32 | A | A |
| 33 | A | n.d. |
| 34 | A | A |
| 35 | A | A |
| 36 | A | A |

TABLE 2-continued

Exemplary compounds of the invention exhibit inhibition of the CRAC channel and inhibition of the IL-2 production in these assays within the following ranges: $IC_{50}$ values from <0.5 μM (A); 0.5-1.0 μM (B); >1.0-5.0 μM (C) and full $IC_{50}$ not determined (n.d.). or % inhibition @ 10 μM < 50 (C), 50-70 (B), >70 (A).

| Example No. | % inhib.[@ 10 μM] FLIPR | $IC_{50}$ [μM] IL-2 |
|---|---|---|
| 37 | B | n.d. |
| 38 | B | n.d. |
| 39 | A | A |
| 40 | A | C |
| 41 | A | n.d. |
| 42 | B | C |
| 43 | C | C |
| 44 | B | C |
| 45 | A | B |
| 46 | A | A |
| 47 | A | C |
| 48 | A | n.d. |
| 49 | A | C |
| 50 | B | n.d. |
| 51 | B | C |
| 52 | B | — |
| 53 | B | — |
| 54 | B | — |
| 55 | B | — |
| 56 | B | — |
| 57 | B | — |
| 58 | B | — |
| 59 | A | — |
| 60 | A | — |
| 61 | A | — |
| 62 | A | — |
| 63 | A | — |
| 64 | A | — |
| 65 | A | — |
| 66 | C | C |
| 67 | C | C |

The invention claimed is:

1. A compound of general formula (I),

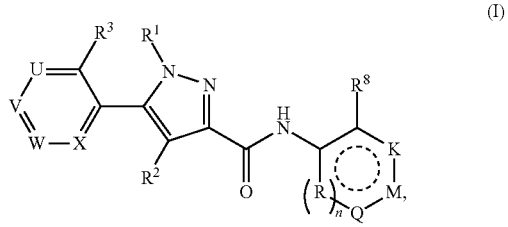

wherein
R$^1$ denotes
 C$_{1-4}$-aliphatic residue, unsubstituted or mono- or polysubstituted; or
 C$_{3-6}$-cycloaliphatic residue or a 3 to 7 membered heterocycloaliphatic residue, in each case unsubstituted or mono- or polysubstituted and in each case optionally connected via a C$_{1-4}$ aliphatic group, which in turn may be unsubstituted or mono- or polysubstituted;
 with the proviso that if R$^1$ represents a 3 to 7 membered heterocycloaliphatic residue, said 3 to 7 membered heterocycloaliphatic residue is connected to the remaining part of the structure according to general formula (I) via a carbon atom of the 3 to 7 membered heterocycloaliphatic residue;
R$^2$ denotes H; F; Cl; Br; I; NO$_2$; CN; CF$_3$; CF$_2$H; CFH$_2$; R$^{13}$; OH; O—R$^{13}$; NH$_2$; N(H)R$^{13}$; N(R$^{13}$)$_2$;

U represents C—R$^4$ or N or N$^+$—O$^-$, V represents C—R$^5$ or N or N$^+$—O$^-$, W represents C—R$^6$ or N or N$^+$—O$^-$, and X represents C—R$^7$ or N or N$^+$—O$^-$, with the proviso that 0, 1, 2 or 3 of variables T, U, V, W and X independently of one another represent(s) either N or N$^+$—O$^-$, whereof 0 or 1 of variables T, U, V, W and X independently of one another represent(s) N$^+$—O$^-$ and with the proviso that at least one of U, V and W does not represent N, wherein R$^4$, R$^5$ and R$^6$ are independently of one another selected from the group consisting of H; F; Cl; Br; I; NO$_2$; CN; CF$_3$; CF$_2$H; CFH$_2$; CF$_2$Cl; CFCl$_2$; C$_{1-8}$-aliphatic residue, unsubstituted or mono- or polysubstituted; C(=O)OH; C(=O)—R$^{13}$; C(=O)R$^{14}$; C(=O)—OR$^{13}$; C(=O)—OR$^{14}$; C(=O)—N(H)(OH); C(=N—OH)—H; C(=N—OH)—R$^{13}$; C(=N—OH)—R$^{14}$; C(=N—O—R$^{13}$)—H; C(=N—O—R$^{13}$)—R$^{13}$; C(=N—O—R$^{13}$)—R$^{14}$; C(=O)NH$_2$; C(=O)—N(H)R$^{13}$; C(=O)—N(R$^{13}$)$_2$; C(=O)—N(H)R$^{14}$; C(=O)—N(R$^{14}$)$_2$; C(=O)—N(R$^{13}$)(R$^{14}$); C(=O)—N(R$^a$)(R$^b$); OH; OR$^{13}$; OCF$_3$; OCF$_2$H; OCFH$_2$; OCF$_2$Cl; OCFCl$_2$; OR$^{14}$; O—C(=O)R$^{13}$; O—C(=O)R$^{14}$; O—C(=O)—N(H)R$^{13}$; O—C(=O)—N(H)R$^{14}$; O—C(=O)—N(R$^{13}$)$_2$; O—C(=O)—N(R$^{14}$)$_2$; O—C(=O)—N(R$^{13}$)(R$^{14}$); O—C(=O)—N(R$^a$)(R$^b$); NH$_2$; N(H)R$^{13}$; N(R$^{13}$)$_2$; N(H)R$^{14}$; N(R$^{14}$)$_2$; N(R$^{13}$)(R$^{14}$); N(R$^a$)(R$^b$); NH—C(=O)—R$^{14}$; NH—C(=O)—R$^{13}$; N(R$^{13}$)—C(=O)—R$^{13}$; N(R$^{13}$)—C(=O)—R$^{14}$; NH—S(=O)$_2$—R$^{13}$; N(R$^{13}$)—S(=O)$_2$—R$^{13}$; NH—S(=O)$_2$—R$^{14}$; N(R$^{13}$)—S(=O)$_2$—R$^{14}$; N(H)—C(=O)—OR$^{13}$; N(H)—C(=O)—OR$^{14}$; N(R$^{13}$)—C(=O)—OR$^{13}$; N(R$^{13}$)—C(=O)—OR$^{14}$; N(H)—C(=O)—NH$_2$; N(H)—C(=O)—N(H)R$^{13}$; N(H)—C(=O)—N(H)R$^{14}$; N(H)—C(=O)—N(R$^{13}$)$_2$; N(H)—C(=O)—N(R$^{14}$)$_2$; N(H)—C(=O)—N(R$^{13}$)(R$^{14}$); N(H)—C(=O)—N(R$^a$)(R$^b$); N(R$^{13}$)—C(=O)—NH$_2$; N(R$^{13}$)—C(=O)—N(H)R$^{13}$; N(R$^{13}$)—C(=O)—N(H)R$^{14}$; N(R$^{13}$)—C(=O)—N(R$^{13}$)$_2$; N(R$^{13}$)—C(=O)—N(R$^{14}$)$_2$; N(R$^{13}$)—C(=O)—N(R$^{13}$)(R$^{14}$); N(R$^{13}$)—C(=O)—N(R$^a$)(R$^b$); SH; S—R$^{13}$; SCF$_3$; S—R$^{14}$; S(=O)$_2$OH; S(=O)$_2$—R$^{13}$; S(=O)$_2$—R$^{14}$; S(=O)$_2$—OR$^{13}$; S(=O)$_2$—OR$^{14}$; S(=O)$_2$—N(H)(R$^{13}$); S(=O)$_2$—N(R$^{13}$)$_2$; S(=O)$_2$—N(H)(R$^{14}$); S(=O)$_2$—N(R$^{13}$)(R$^{14}$); S(=O)$_2$—N(R$^a$)(R$^b$);

R$^3$ is selected from the group consisting of F; Cl; Br; I; NO$_2$; CN; CF$_3$; CF$_2$H; CFH$_2$; CF$_2$Cl; CFCl$_2$; R$^{13}$; R$^{14}$; C(=O)OH; C(=O)—R$^{13}$; C(=O)R$^{14}$; C(=O)—OR$^{13}$; C(=O)—OR$^{14}$; C(=O)—N(H)(OH); C(=N—OH)—H; C(=N—OH)—R$^{13}$; C(=N—OH)—R$^{14}$; C(=N—O—R$^{13}$)—H; C(=N—O—R$^{13}$)—R$^{13}$; C(=N—O—R$^{13}$)—R$^{14}$; C(=O)NH$_2$; C(=O)—N(H)R$^{13}$; C(=O)—N(R$^{13}$)$_2$; C(=O)—N(H)R$^{14}$; C(=O)—N(R$^{14}$)$_2$; C(=O)—N(R$^{13}$)(R$^{14}$); C(=O)—N(R$^a$)(R$^b$); OH; OR$^{13}$; OCF$_3$; OCF$_2$H; OCFH$_2$; OCF$_2$Cl; OCFCl$_2$; OR$^{14}$; O—C(=O)R$^{13}$; O—C(=O)R$^{14}$; O—C(=O)—N(H)R$^{13}$; O—C(=O)—N(H)R$^{14}$; O—C(=O)—N(R$^{13}$)$_2$; O—C(=O)—N(R$^{14}$)$_2$; O—C(=O)—N(R$^{13}$)(R$^{14}$); O—C(=O)—N(R$^a$)(R$^b$); NH$_2$; N(H)R$^{13}$; N(R$^{13}$)$_2$; N(H)R$^{14}$; N(R$^{14}$)$_2$; N(R$^{13}$)(R$^{14}$); N(R$^a$)(R$^b$); NH—C(=O)—R$^{14}$; NH—C(=O)—R$^{13}$; N(R$^{13}$)—C(=O)—R$^{13}$; N(R$^{13}$)—C(=O)—R$^{14}$; NH—S(=O)$_2$—R$^{13}$; N(R$^{13}$)—S(=O)$_2$—R$^{13}$; NH—S(=O)$_2$—R$^{14}$; N(R$^{13}$)—S(=O)$_2$—R$^{14}$; N(H)—C(=O)—OR$^{13}$; N(H)—C(=O)—OR$^{14}$; N(R$^{13}$)—C(=O)—OR$^{13}$; N(R$^{13}$)—C(=O)—OR$^{14}$; N(H)—C(=O)—NH$_2$; N(H)—C(=O)—N(H)R$^{13}$; N(H)—C(=O)—N(H)R$^{14}$; N(H)—C(=O)—N(R$^{13}$)$_2$; N(H)—C(=O)—N(R$^{14}$)$_2$; N(H)—C(=O)—N(R$^{13}$)(R$^{14}$); N(H)—C(=O)—N(R$^a$)(R$^b$); N(R$^{13}$)—C(=O)—NH$_2$; N(R$^{13}$)—C(=O)—N(H)R$^{13}$; N(R$^{13}$)—C(=O)—N(H)R$^{14}$; N(R$^{13}$)—C(=O)—N(R$^{13}$)$_2$; N(R$^{13}$)—C(=O)—N(R$^{14}$)$_2$; N(R$^{13}$)—C(=O)—N(R$^{13}$)(R$^{14}$); N(R$^{13}$)—C(=O)—N(R$^a$)(R$^b$); SH; S—R$^{13}$; SCF$_3$; S—R$^{14}$; S(=O)$_2$OH; S(=O)$_2$—R$^{13}$; S(=O)$_2$—R$^{14}$; S(=O)—R$^{13}$; S(=O)—R$^{14}$; S(=O)$_2$—OR$^{13}$; S(=O)$_2$—OR$^{14}$; S(=O)$_2$—N(H)(R$^{13}$); S(=O)$_2$—N(R$^{13}$)$_2$; S(=O)$_2$—N(H)(R$^{14}$); S(=O)$_2$—N(R$^{13}$)(R$^{14}$); S(=O)$_2$—N(R$^a$)(R$^b$); and R$^7$ is selected from the group consisting of H F; Cl; Br; I; NO$_2$; CN; CF$_3$; CF$_2$H; CFH$_2$; CF$_2$Cl; CFCl$_2$; R$^{13}$; R$^{14}$; C(=O)OH; C(=O)—R$^{13}$; C(=O)R$^{14}$; C(=O)—OR$^{13}$; C(=O)—OR$^{14}$; C(=O)—N(H)(OH); C(=N—OH)—H; C(=N—OH)—R$^{13}$; C(=N—OH)—R$^{14}$; C(=N—O—R$^{13}$)—H; C(=N—O—R$^{13}$)—R$^{13}$; C(=N—O—R$^{13}$)—R$^{14}$; C(=O)NH$_2$; C(=O)—N(H)R$^{13}$; C(=O)—N(R$^{13}$)$_2$; C(=O)—N(H)R$^{14}$; C(=O)—N(R$^{14}$)$_2$; C(=O)—N(R$^{13}$)(R$^{14}$); C(=O)—N(R$^a$)(R$^b$); OH; OR$^{13}$; OCF$_3$; OCF$_2$H; OCFH$_2$; OCF$_2$Cl; OCFCl$_2$; OR$^{14}$; O—C(=O)R$^{13}$; O—C(=O)R$^{14}$; O—C(=O)—N(H)R$^{13}$; O—C(=O)—N(H)R$^{14}$; O—C(=O)—N(R$^{13}$)$_2$; O—C(=O)—N(R$^{14}$)$_2$; O—C(=O)—N(R$^{13}$)(R$^{14}$); O—C(=O)—N(R$^a$)(R$^b$); NH$_2$; N(H)R$^{13}$; N(R$^{13}$)$_2$; N(H)R$^{14}$; N(R$^{14}$)$_2$; N(R$^{13}$)(R$^{14}$); N(R$^a$)(R$^b$); NH—C(=O)—R$^{14}$; NH—C(=O)—R$^{13}$; N(R$^{13}$)—C(=O)—R$^{13}$; N(R$^{13}$)—C(=O)—R$^{14}$; NH—S(=O)$_2$—R$^{13}$; N(R$^{13}$)—S(=O)$_2$—R$^{13}$; NH—S(=O)$_2$—R$^{14}$; N(R$^{13}$)—S(=O)$_2$—R$^{14}$; N(H)—C(=O)—OR$^{13}$; N(H)—C(=O)—OR$^{14}$; N(R$^{13}$)—C(=O)—OR$^{13}$; N(R$^{13}$)—C(=O)—OR$^{14}$; N(H)—C(=O)—NH$_2$; N(H)—C(=O)—N(H)R$^{13}$; N(H)—C(=O)—N(H)R$^{14}$; N(H)—C(=O)—N(R$^{13}$)$_2$; N(H)—C(=O)—N(R$^{14}$)$_2$; N(H)—C(=O)—N(R$^{13}$)(R$^{14}$); N(H)—C(=O)—N(R$^a$)(R$^b$); N(R$^{13}$)—C(=O)—NH$_2$; N(R$^{13}$)—C(=O)—N(H)R$^{13}$; N(R$^{13}$)—C(=O)—N(H)R$^{14}$; N(R$^{13}$)—C(=O)—N(R$^{13}$)$_2$; N(R$^{13}$)—C(=O)—N(R$^{14}$)$_2$; N(R$^{13}$)—C(=O)—N(R$^{13}$)(R$^{14}$); N(R$^{13}$)—C(=O)—N(R$^a$)(R$^b$); SH; S—R$^{13}$; SCF$_3$; S—R$^{14}$; S(=O)$_2$OH; S(=O)$_2$—R$^{13}$; S(=O)$_2$—R$^{14}$; S(=O)—R$^{13}$; S(=O)—R$^{14}$; S(=O)$_2$—OR$^{13}$; S(=O)$_2$—OR$^{14}$; S(=O)$_2$—N(H)(R$^{13}$); S(=O)$_2$—N(R$^{13}$)$_2$; S(=O)$_2$—N(H)(R$^{14}$); S(=O)$_2$—N(R$^{13}$)(R$^{14}$); S(=O)$_2$—N(R$^a$)(R$^b$)

n represents 0 or 1, wherein, if n represents 1, then
K represents C—R$^9$ or N or N$^+$—O$^-$,
M represents C—R$^{10}$ or N or N$^+$—O$^-$,
Q represents C—R$^{11}$ or N or N$^+$—O$^-$, and
R represents C—R$^{12}$ or N or N$^+$—O$^-$,
with the proviso that 0, 1, 2 or 3 of variables K, M, Q and R independently of one another represent(s) either N or N$^+$—O$^-$, whereof 0 or 1 of variables K, M, Q and R independently represents N$^+$—O$^-$, wherein, if n represents 0, then
K represents C—R$^9$ or N or N$^+$—O$^-$ or O or S or NH or N(C$_{1-4}$-aliphatic residue), M represents C—R¹⁰ or N or N⁺—O⁻ or O or S or NH or N(C₁₋₄-aliphatic residue) and Q represents C—R¹¹ or N or N⁺—O⁻ or O or S or NH or N(C₁₋₄-aliphatic residue), with the proviso that one of K, M and Q represents O or S or NH or N(C₁₋₄-aliphatic residue) and the remaining of K, M and Q independently represent C—R⁹ 'respectively C—R¹⁰, respectively C—R¹¹ or N or N⁺—O⁻ and with the proviso that 0, 1 or 2 of variables K, M and Q independently of one another represent either N or N⁺—O⁻, whereof 0 or 1 of variables K, M and Q represents N⁺—O⁻, wherein R⁸ is selected from F, Cl, CF₃, CF₂H, CFH₂, CH₃, CN, OCF₂H, OCFH₂, and OCF₃, and wherein R⁹, R¹⁰, R¹¹ and R¹² are independently of one another selected from the group consisting of H; F; Cl; Br; I; NO₂; CN; CF₃; CF₂H; CFH₂; CF₂Cl; CFCl₂; R¹³; R¹⁴; C(=O)OH; C(=O)—R¹³; C(=O)R¹⁴; C(=O)—OR¹³; C(=O)—OR¹⁴; C(=O)—N(H)(OH); C(=N—OH)—H; C(=N—OH)—R¹³; C(=N—OH)—R¹⁴; C(=N—O—R¹³)—H; C(=N—O—R¹³)—R¹³; C(=N—O—R¹³)—R¹⁴; C(=O)NH₂; C(=O)—N(H)R¹³; C(=O)—N(R¹³)₂; C(=O)—N(H)R¹⁴; C(=O)—N(R¹⁴)₂; C(=O)—N(R¹³)(R¹⁴); C(=O)—N(Rᵃ)(Rᵇ); OH; OR¹³; OCF₃; OCF₂H; OCFH₂; OCF₂Cl; OCFCl₂; OR¹⁴; O—C(=O)R¹³; O—C(=O)R¹⁴; O—C(=O)—N(H)R¹³; O—C(=O)—N(H)R¹⁴; O—C(=O)—N(R¹³)₂; O—C(=O)—N(R¹⁴)₂; O—C(=O)—N(R¹³)(R¹⁴); O—C(=O)—N(Rᵃ)(Rᵇ); NH₂; N(H)R¹³; N(R¹³)₂; N(H)R¹⁴; N(R¹⁴)₂; N(R¹³)(R¹⁴); N(Rᵃ)(Rᵇ); NH—C(=O)—R¹⁴; NH—C(=O)—R¹³; N(R¹³)—C(=O)—R¹³; N(R¹³)—C(=O)—R¹⁴; NH—S(=O)₂—R¹³; N(R¹³)—S(=O)₂—R¹³; NH—S(=O)₂—R¹⁴; N(R¹³)—S(=O)₂—R¹⁴; N(H)—C(=O)—OR¹³; N(H)—C(=O)—OR¹⁴; N(R¹³)—C(=O)—OR¹³; N(R¹³)—C(=O)—OR¹⁴; N(H)—C(=O)—NH₂; N(H)—C(=O)—N(H)R¹³; N(H)—C(=O)—N(H)R¹⁴; N(H)—C(=O)—N(R¹³)₂; N(H)—C(=O)—N(R¹⁴)₂; N(H)—C(=O)—N(R¹³)(R¹⁴); N(H)—C(=O)—N(Rᵃ)(Rᵇ); N(R¹³)—C(=O)—NH₂; N(R¹³)—C(=O)—N(H)R¹³; N(R¹³)—C(=O)—N(H)R¹⁴; N(R¹³)—C(=O)—N(R¹³)₂; N(R¹³)—C(=O)—N(R¹⁴)₂; N(R¹³)—C(=O)—N(R¹³)(R¹⁴); N(R¹³)—C(=O)—N(Rᵃ)(Rᵇ); SH; S—R¹³; SCF₃; S—R¹⁴; S(=O)₂OH; S(=O)₂—R¹³; S(=O)₂—R¹⁴; S(=O)—R¹³; S(=O)—R¹⁴; S(=O)₂—OR¹³; S(=O)₂—OR¹⁴; S(=O)₂—N(H)(R¹³); S(=O)₂—N(R¹³)₂; S(=O)₂—N(H)(R¹⁴); S(=O)₂—N(R¹³)(R¹⁴); S(=O)₂—N(Rᵃ)(Rᵇ);

wherein each R¹³ independently of each other denotes
C₁₋₈-aliphatic residue, unsubstituted or mono- or polysubstituted;
or
C₃₋₆-cycloaliphatic residue or 3 to 7 membered heterocycloaliphatic residue, in each case unsubstituted or mono- or polysubstituted;
or
C₃₋₆-cycloaliphatic residue or 3 to 7 membered heterocycloaliphatic residue, in each case unsubstituted or mono- or polysubstituted, and in each case connected via a C₁₋₄-aliphatic residue, unsubstituted or mono- or polysubstituted;

each R¹⁴ independently of each other denotes
aryl and heteroaryl residue, in each case independently of one another unsubstituted or mono- or polysubstituted,
or
aryl and heteroaryl residue, in each case independently of one another unsubstituted or mono- or polysubstituted and in each case connected via a C₁₋₄-aliphatic group, unsubstituted or mono- or polysubstituted;

Rᵃ and Rᵇ together with the N-atom connecting them form a 3 to 7 membered heterocyclic residue, unsubstituted or mono- or polysubstituted;

optionally in the form of a single stereoisomer or a mixture of stereoisomers, in the form of the free compound and/or a physiologically acceptable salt thereof and/or a physiologically acceptable solvate thereof, with the proviso that the compound according to general formula (I) does not represent N-(2-Cyanophenyl)-5-(2-methoxy-5-methylphenyl)-1-methyl-1H-pyrazole-3-carboxamide,

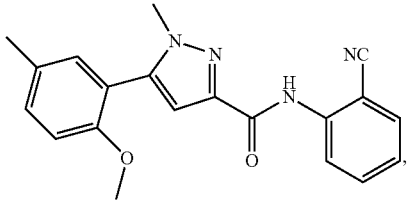

5-(2-Fluoro-4-methoxyphenyl)-N-(2-fluorophenyl)-1-methyl-1H-pyrazole-3-carboxamide,

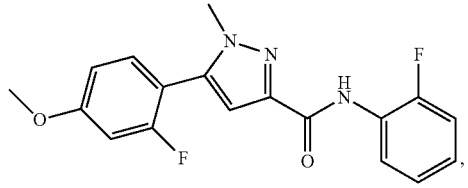 [SMILES: COc1ccc(-c2cc(C(=O)Nc3ccccc3F)nn2C)c(F)c1]

1-Ethyl-5-(2-fluoro-4-methoxyphenyl)-N-(2-fluorophenyl)-1H-pyrazole-3-carboxamide

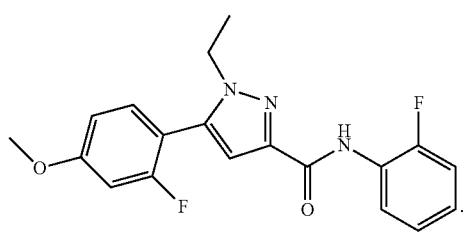 [SMILES: CCn1nc(C(=O)Nc2ccccc2F)cc1-c1ccc(OC)cc1F]

2. A compound according to claim 1, wherein R² is selected from the group consisting of H; F; Cl; Br; CN; CF₃; CF₂H; CFH₂; R¹³; OH; O—R¹³; NH₂; N(H)R¹³; N(R¹³)₂,
wherein R¹³ independently of each other denotes an unsubstituted or mono- or polysubstituted C₁₋₄ aliphatic residue.

3. A compound according to claim 1 wherein R¹ is selected from the group consisting of unsubstituted C₁₋₄-aliphatic residue and unsubstituted cyclopropyl.

4. A compound according to claim 1 wherein
n represents 1, and
K represents C—R$^9$, M represents C—R$^{10}$ or N or or N$^+$—O$^-$, Q represents C—R$^{11}$ and R represents C—R$^{12}$
or
n represents 1, and
K represents C—R$^9$, M represents N, Q represents C—R$^{11}$ and R represents N.

5. A compound according to claim 1 wherein
n represents 1,
R represents C—R$^{12}$,
wherein R$^{12}$ is selected from the group consisting of H; CH$_3$; CF$_3$; CF$_2$H; CFH$_2$; CF$_2$Cl; CFCl$_2$; CH$_2$CH$_3$; CN; OH; OCH$_3$; OCHF$_2$; OCH$_2$F; OCHF$_2$; OCF$_3$; NH$_2$; NHCH$_3$; N(CH$_3$)$_2$; NH(C=O)CH$_3$; F; Cl and Br.

6. A compound according to claim 1 wherein
n represents 1,
M represents N or N$^+$—O$^-$ or C—R$^{10}$,
wherein R$^{10}$ is selected from the group consisting of H; F; Cl; CN; CF$_3$; CF$_2$H; CFH$_2$; CF$_2$Cl; CFCl$_2$; C$_{1-8}$-aliphatic residue; C(=O)OH; C(=O)—NH$_2$; C(=O)—C$_{1-8}$-aliphatic residue; C(=O)O—C$_{1-8}$-aliphatic residue; C(=O)NH—C$_{1-8}$-aliphatic residue; C(=O)N(C$_{1-8}$-aliphatic residue)$_2$; OH; O—C$_{1-8}$-aliphatic residue; OCF$_3$; OCF$_2$H; OCFH$_2$; O—C(=O)—C$_{1-8}$-aliphatic residue; NH$_2$; N(H)—C$_{1-8}$-aliphatic residue; N(C$_{1-8}$-aliphatic residue)$_2$; N(H)—C(=O)—C$_{1-8}$-aliphatic residue; N(C$_{1-8}$-aliphatic residue)-S(=O)$_2$—C$_{1-8}$-aliphatic residue; N(H)—S(=O)$_2$—NH$_2$; S(=O)$_2$—C$_{1-8}$-aliphatic residue.

7. A compound according to claim 1 wherein
U represents C—R$^4$, V represents C—R$^5$, W represents C—R$^6$, and X represents C—R$^7$.

8. A compound according to claim 1 wherein
R$^3$ is selected from the group consisting of F; Cl; CN; CF$_3$; CF$_2$H; CFH$_2$; CF$_2$Cl; CFCl$_2$; OCHF$_2$; OCFH$_2$; OCF$_3$; C$_{1-8}$-aliphatic residue; C(=O)OH; C(=O)—NH$_2$; C(=O)—C$_{1-8}$-aliphatic residue; C(=O)O—C$_{1-8}$-aliphatic residue; C(=O)NH—C$_{1-8}$-aliphatic residue; C(=O)N(C$_{1-8}$-aliphatic residue)$_2$; OH; O—C$_{1-8}$-aliphatic residue; OCF$_3$; OCF$_2$H; OCFH$_2$; O—C(=O)—C$_{1-8}$-aliphatic residue; NH$_2$; N(H)—C$_{1-8}$-aliphatic residue; N(C$_{1-8}$-aliphatic residue)$_2$; N(H)—C(=O)—C$_{1-8}$-aliphatic residue; N(C$_{1-8}$-aliphatic residue)-S(=O)$_2$—C$_{1-8}$-aliphatic residue; N(H)—S(=O)$_2$—NH$_2$; S(=O)$_2$—C$_{1-8}$-aliphatic residue; C$_{3-6}$-cycloaliphatic residue; 3 to 7 membered heterocycloaliphatic residue, and
X represents C—R$^7$ and
R$^7$ represents H or F or CH$_3$ or CF$_3$.

9. A compound according to claim 1 wherein
R$^4$, R$^5$ and R$^6$ are selected from the group consisting of H; F; Cl; CN; CF$_3$; CF$_2$H; CFH$_2$; CF$_2$Cl; CFCl$_2$; OCHF$_2$; OCFH$_2$; OCF$_3$; C$_{1-8}$-aliphatic residue; C(=O)—NH$_2$; C(=O)—C$_{1-8}$-aliphatic residue; C(=O)O—C$_{1-8}$-aliphatic residue; C(=O)NH—C$_{1-8}$-aliphatic residue; C(=O)N(C$_{1-8}$-aliphatic residue)$_2$; OH; O—C$_{1-8}$-aliphatic residue; OCF$_3$; OCF$_2$H; OCFH$_2$; O—C(=O)—C$_{1-8}$-aliphatic residue; NH$_2$; N(H)—C$_{1-8}$-aliphatic residue; N(C$_{1-8}$-aliphatic residue)$_2$; N(H)—C(=O)—C$_{1-8}$-aliphatic residue; N(C$_{1-8}$-aliphatic residue)-S(=O)$_2$—C$_{1-8}$-aliphatic residue; N(H)—S(=O)$_2$—NH$_2$; S(=O)$_2$—C$_{1-8}$-aliphatic residue; preferably from the group consisting of H; F; Cl; OCH$_3$; OCHF$_2$; OCFH$_2$; OCF$_3$; CN; CH$_3$; CF$_3$; CF$_2$H and CFH$_2$.

10. A compound according to claim 1 wherein
R$^1$ denotes unsubstituted C$_{1-4}$-aliphatic residue;
R$^2$ denotes H; F; Cl, OH, NH$_2$, NHCH$_3$, N(CH$_3$)$_2$, CH$_2$NH$_2$, CH$_2$—N(CH$_3$)$_2$, CH$_2$OH; or unsubstituted C$_{1-4}$ aliphatic residue; preferably denotes H, Cl, NH$_2$, CH$_3$, CH$_2$OH and CH$_2$CH$_3$;
U represents C—R$^4$ or N, V represents C—R$^5$ or N, W represents C—R$^6$ or N, and X represents C—R$^7$,
with the proviso that 0, 1, 2 or 3 of variables U, V, W and X independently of one another represent(s) N,
and with the proviso that at least one of U, V and W does not represent N,
R$^3$ denotes F; Cl; CN; CF$_3$; CF$_2$H; CFH$_2$; OCF$_3$; OCF$_2$H; OCFH$_2$; cyclopropyl; unsubstituted C$_{1-4}$-aliphatic residue; OH or unsubstituted O—C$_{1-4}$-aliphatic residue;
R$^7$ denotes H, F, CH$_3$ or CF$_3$; and
R$^4$, R$^5$ and R$^6$ are independently selected from the group consisting of
H; F; Cl; CN; CF$_3$; CF$_2$H; CFH$_2$; CF$_2$Cl; CFCl$_2$; OCHF$_2$; OCFH$_2$; OCF$_3$; C$_{1-8}$-aliphatic residue; C(=O)—NH$_2$; C(=O)—C$_{1-8}$-aliphatic residue; C(=O)O—C$_{1-8}$-aliphatic residue; C(=O)NH—C$_{1-8}$-aliphatic residue; C(=O)N(C$_{1-8}$-aliphatic residue)$_2$; OH; O—C$_{1-8}$-aliphatic residue; OCF$_3$; OCF$_2$H; OCFH$_2$; O—C(=O)—C$_{1-8}$-aliphatic residue; NH$_2$; N(H)—C$_{1-8}$-aliphatic residue; N(C$_{1-8}$-aliphatic residue)$_2$; N(H)—C(=O)—C$_{1-8}$-aliphatic residue; N(C$_{1-8}$-aliphatic residue)-S(=O)$_2$—C$_{1-8}$-aliphatic residue; N(H)—S(=O)$_2$—NH$_2$; S(=O)$_2$—C$_{1-8}$-aliphatic residue;
n represents 1,
K represents C—R$^9$ and Q represents C—R$^{11}$,
wherein R$^9$ and R$^{11}$ are independently of one another selected from the group consisting of H; F; Cl; CN; CF$_3$; CF$_2$H; CFH$_2$; OCF$_3$; OCF$_2$H; OCFH$_2$; CH$_3$; OH; and OCH$_3$; and
M represents N or N$^+$—O$^-$ or C—R$^{10}$,
wherein R$^{10}$ is selected from the group consisting of H; F; Cl; OCH$_3$; CN; CH$_3$; CF$_3$; CF$_2$H; CFH$_2$ or S(=O)$_2$—CH$_3$
R represents C—R$^{12}$,
wherein R$^{12}$ is selected from the group consisting of H; CH$_3$; CF$_3$; CF$_2$H; CFH$_2$; CH$_2$CH$_3$; CN; OH; OCH$_3$; OCHF$_2$; OCH$_2$F; OCHF$_2$; OCF$_3$; F and Cl.

11. A compound according to claim 1 wherein the compound has general formula (Iaa), (Iaa)

wherein
R$^1$, R$^2$, U, V, W and X are defined as as before,
R$^8$ denotes F, Cl, CN, CF$_3$, CF$_2$H, CFH$_2$, CH$_3$ or O—CH$_3$ and
K, M, Q and R independently represent N, CH or C—R$^{8a}$,
wherein R$^{8a}$ denotes F, Cl, CN, CF$_3$, CF$_2$H, CFH$_2$, CH$_3$, CH$_2$CH$_3$, O—CH$_3$ or O—CH$_2$CH$_3$, with the proviso, that 0 or 1 of the substituents K, M, Q and R represent N.

12. A compound according to claim 1 wherein the compound is selected from the group consisting of 1  N-(2,6-Difluoro-phenyl)-5-(2-methoxyphenyl)-1-methyl-1H-pyrazole-3-carboxylic acid amide;
2  N-(2,4-Difluoro-phenyl)-5-(2,5-dimethoxyphenyl)-1-methyl-1H-pyrazole-3-carboxylic acid amide;
3  5-(2-Ethoxy-5-methoxy-phenyl)-N-(3-fluoro-pyridin-4-yl)-1-methyl-1H-pyrazole-3-carboxylic acid amide;
4  N-(2,6-Difluoro-phenyl)-5-(2-ethoxy-5-methoxy-phenyl)-1-methyl-1H-pyrazole-3-carboxylic acid amide;
5  5-(2,5-Difluoro-phenyl)-N-(2,6-difluoro-phenyl)-1-methyl-1H-pyrazole-3-carboxylic acid amide;
6  N-(2,6-Difluoro-phenyl)-5-[2-fluoro-5-(trifluoromethyl)-phenyl]-1-methyl-1H-pyrazole-3-carboxylic acid amide;
7  N-(2,6-Difluoro-phenyl)-1-methyl-5-[2-(trifluoromethyl)-phenyl]-1H-pyrazole-3-carboxylic acid amide;
8  N-(2,6-Difluoro-phenyl)-5-[5-methoxy-2-(trifluoromethyloxy)-phenyl]-1-methyl-1H-pyrazole-3-carboxylic acid amide;
9  N-(3-Fluoro-pyridin-4-yl)-5-[5-methoxy-2-(trifluoromethyloxy)-phenyl]-1-methyl-1H-pyrazole-3-carboxylic acid amide;
10  N-(2,6-Difluoro-phenyl)-5-(5-fluoro-2-methoxy-phenyl)-1-methyl-1H-pyrazole-3-carboxylic acid amide;
11  5-[2-Chloro-4-(trifluoromethyloxy)-phenyl]-N-(3-fluoro-pyridin-4-yl)-1-methyl-1H-pyrazole-3-carboxylic acid amide;
12  5-[2-Chloro-4-(trifluoromethyloxy)-phenyl]-N-(2,6-difluoro-phenyl)-1-methyl-1H-pyrazole-3-carboxylic acid amide;
13  5-(2,5-Dimethoxyphenyl)-N-(2-fluoro-4-methylsulfonyl-phenyl)-1-methyl-1H-pyrazole-3-carboxylic acid amide;
14  5-(2,5-Dimethoxyphenyl)-1-methyl-N-[3-(trifluoromethyl)-pyridin-4-yl]-1H-pyrazole-3-carboxylic acid amide;
15  N-(3-Cyano-pyridin-4-yl)-5-(2,5-dimethoxyphenyl)-1-methyl-1H-pyrazole-3-carboxylic acid amide;
16  5-(2,5-Dimethoxyphenyl)-1-methyl-N-(4-methyl-pyridin-3-yl)-1H-pyrazole-3-carboxylic acid amide;
17  5-(2,5-Dimethoxyphenyl)-N-(4,6-dimethyl-pyridin-3-yl)-1-methyl-1H-pyrazole-3-carboxylic acid amide;
18  5-(2,5-Dimethoxyphenyl)-1-methyl-N-(5-methyl-pyrimidin-4-yl)-1H-pyrazole-3-carboxylic acid amide;
19  5-(2,5-Dimethoxyphenyl)-N-(3-fluoro-pyridin-4-yl)-1-methyl-1H-pyrazole-3-carboxylic acid amide;
20  5-(2,5-Dimethoxyphenyl)-1-methyl-N-(3-methyl-pyridin-4-yl)-1H-pyrazole-3-carboxylic acid amide;
21  N-(2,6-Difluoro-phenyl)-5-(2,5-dimethoxyphenyl)-1-methyl-1H-pyrazole-3-carboxylic acid amide;
22  5-(5-Chloro-2-methoxy-phenyl)-N-(3-fluoro-pyridin-4-yl)-1-methyl-1H-pyrazole-3-carboxylic acid amide;
23  5-(5-Chloro-2-methyl-phenyl)-N-(3-fluoro-pyridin-4-yl)-1-methyl-1H-pyrazole-3-carboxylic acid amide;
24  N-(3-Fluoro-pyridin-4-yl)-5-(4-methoxy-2-methylphenyl)-1-methyl-1H-pyrazole-3-carboxylic acid amide;
25  5-(2,5-Dimethoxyphenyl)-N-(3-fluoro-pyridin-4-yl)-1,4-dimethyl-1H-pyrazole-3-carboxylic acid amide;
26  5-(5-Chloro-2-methyl-phenyl)-N-(2,6-difluoro-phenyl)-1-methyl-1H-pyrazole-3-carboxylic acid amide;
27  5-(2,5-Dimethoxyphenyl)-1-methyl-N-(o-tolyl)-1H-pyrazole-3-carboxylic acid amide;
28  5-(5-Chloro-2-methyl-phenyl)-1-methyl-N-(3-methyl-pyridin-4-yl)-1H-pyrazole-3-carboxylic acid amide;
29  N-(3-Fluoro-pyridin-4-yl)-1-methyl-5-[2-methyl-5-(trifluoromethyl)-phenyl]-1H-pyrazole-3-carboxylic acid amide;
30  N-(2,6-Difluoro-phenyl)-1-methyl-5-[2-methyl-5-(trifluoromethyl)-phenyl]-1H-pyrazole-3-carboxylic acid amide;
31  N-(2,6-Difluoro-4-methoxy-phenyl)-5-(2,5-dimethoxyphenyl)-1-methyl-1H-pyrazole-3-carboxylic acid amide;
32  5-(2,5-Dimethoxyphenyl)-N-(2-fluoro-6-methyl-phenyl)-1-methyl-1H-pyrazole-3-carboxylic acid amide;
33  5-(2,5-Dimethoxyphenyl)-N-(2-fluorophenyl)-1-methyl-1H-pyrazole-3-carboxylic acid amide;
34  N-(3,5-Difluoro-pyridin-4-yl)-5-(2,5-dimethoxyphenyl)-1-methyl-1H-pyrazole-3-carboxylic acid amide;
35  N-(2-Chloro-6-fluoro-phenyl)-5-(2,5-dimethoxyphenyl)-1-methyl-1H-pyrazole-3-carboxylic acid amide;
36  5-[2-Chloro-5-(trifluoromethyl)-phenyl]-N-(2,6-difluoro-phenyl)-1-methyl-1H-pyrazole-3-carboxylic acid amide;
37  N-(2,6-Difluoro-phenyl)-5-(2,5-dimethoxyphenyl)-1-ethyl-1H-pyrazole-3-carboxylic acid amide;
38  5-[2-Cyano-5-(trifluoromethyl)-phenyl]-N-(2,6-difluoro-phenyl)-1-methyl-1H-pyrazole-3-carboxylic acid amide;
39  4-Chloro-N-(2,6-difluoro-phenyl)-5-(2,5-dimethoxyphenyl)-1-methyl-1H-pyrazole-3-carboxylic acid amide;
40  4-Chloro-5-(2,5-dimethoxyphenyl)-N-(3-fluoro-pyridin-4-yl)-1-methyl-1H-pyrazole-3-carboxylic acid amide;
41  N-(2,6-Difluoro-phenyl)-5-(2,5-dimethoxyphenyl)-1H-pyrazole-3-carboxylic acid amide;
42  N-(2,6-Difluoro-phenyl)-5-(2,5-dimethoxyphenyl)-4-ethyl-1-methyl-1H-pyrazole-3-carboxylic acid amide;
43  N-(2,6-Difluoro-phenyl)-5-(2,5-dimethoxyphenyl)-4-(hydroxymethyl)-1-methyl-1H-pyrazole-3-carboxylic acid amide;
44  4-Amino-N-(2,6-difluoro-phenyl)-5-(2,5-dimethoxyphenyl)-1-methyl-1H-pyrazole-3-carboxylic acid amide;
45  5-[2-Cyclopropyl-5-(trifluoromethyloxy)-phenyl]-N-(2,6-difluoro-phenyl)-1-methyl-1H-pyrazole-3-carboxylic acid amide;
46  5-[2-Cyclopropyl-5-(trifluoromethyloxy)-phenyl]-N-(3,5-difluoro-pyridin-4-yl)-1-methyl-1H-pyrazole-3-carboxylic acid amide;
47  5-[2-Cyclopropyl-5-(trifluoromethyloxy)-phenyl]-N-(3-fluoro-pyridin-4-yl)-1-methyl-1H-pyrazole-3-carboxylic acid amide;
48  4-Amino-5-(2,5-dimethoxyphenyl)-N-(3-fluoro-pyridin-4-yl)-1-methyl-1H-pyrazole-3-carboxylic acid amide;
49  N-(3,5-Difluoro-pyridin-4-yl)-5-[2-fluoro-6-(trifluoromethyl)-phenyl]-1-methyl-1H-pyrazole-3-carboxylic acid amide;
50  N,5-Bis(2,6-difluoro-phenyl)-1-methyl-1H-pyrazole-3-carboxylic acid amide;
51  N-(2,6-Difluoro-phenyl)-5-[2-fluoro-6-(trifluoromethyl)-phenyl]-1-methyl-1H-pyrazole-3-carboxylic acid amide;
52  N-(2-Chloro-6-methyl-phenyl)-5-(2,6-difluoro-phenyl)-1-methyl-1H-pyrazole-3-carboxylic acid amide;
53  5-(2,6-Difluoro-phenyl)-N-(3-fluoro-5-methyl-pyridin-4-yl)-1-methyl-1H-pyrazole-3-carboxylic acid amide;

54 5-[2-Fluoro-6-(trifluoromethyl)-phenyl]-1-methyl-N-[2-(trifluoromethyloxy)-phenyl]-1H-pyrazole-3-carboxylic acid amide;

55 N-(2,4-Difluoro-phenyl)-5-[2-fluoro-6-(trifluoromethyl)-phenyl]-1-methyl-1H-pyrazole-3-carboxylic acid amide;

56 N-(2-Cyano-phenyl)-5-[2-fluoro-6-(trifluoromethyl)-phenyl]-1-methyl-1H-pyrazole-3-carboxylic acid amide;

57 N-(2,4-Dichlorophenyl)-5-[2-fluoro-6-(trifluoromethyl)-phenyl]-1-methyl-1H-pyrazole-3-carboxylic acid amide;

58 N-(2,6-Difluoro-4-methoxy-phenyl)-5-[2-fluoro-6-(trifluoromethyl)-phenyl]-1-methyl-1H-pyrazole-3-carboxylic acid amide;

59 N-(2-Fluoro-6-methyl-phenyl)-5-[2-fluoro-6-(trifluoromethyl)-phenyl]-1-methyl-1H-pyrazole-3-carboxylic acid amide;

60 5-[2-Fluoro-6-(trifluoromethyl)-phenyl]-1-methyl-N-[2-(trifluoromethyl)-phenyl]-1H-pyrazole-3-carboxylic acid amide;

61 N-(2-Fluorophenyl)-5-[2-fluoro-6-(trifluoromethyl)-phenyl]-1-methyl-1H-pyrazole-3-carboxylic acid amide;

62 N-(3-Fluoro-pyridin-4-yl)-5-[2-fluoro-6-(trifluoromethyl)-phenyl]-1-methyl-1H-pyrazole-3-carboxylic acid amide;

63 N-(3-Fluoro-5-methyl-pyridin-4-yl)-5-[2-fluoro-6-(trifluoromethyl)-phenyl]-1-methyl-1H-pyrazole-3-carboxylic acid amide;

64 1-Methyl-5-(4-methyl-pyridin-3-yl)-N-[2-(trifluoromethyl)-phenyl]-1H-pyrazole-3-carboxylic acid amide;

65 N-(3-Fluoro-5-methyl-pyridin-4-yl)-1-methyl-5-(4-methyl-pyridin-3-yl)-1H-pyrazole-3-carboxylic acid amide;

66 N-(2,6-Difluoro-phenyl)-5-(2-methoxy-4-methylsulfonyl-phenyl)-1-methyl-1H-pyrazole-3-carboxylic acid amide;

67 N-(3,5-Difluoro-pyridin-4-yl)-5-(2,5-dimethoxyphenyl)-1-methyl-4-methylamino-1H-pyrazole-3-carboxylic acid amide;

optionally in the form of the free compound and/or a physiologically acceptable salt thereof and/or a physiologically acceptable solvate thereof.

13. A pharmaceutical composition comprising at least one compound according claim 1 and optionally one or more suitable, pharmaceutically compatible auxiliaries and/or, if appropriate, one or more further pharmacologically active compounds.

14. A method for the treatment of one or more disorders selected from the group consisting of inflammatory disorders and/or autoimmune diseases and/or allergic disorders comprising administering to a patient in need thereof an effective amount of a compound according to claim 1.

15. A method for the treatment of psoriasis and/or psoriatic arthritis and/or rheumatoid arthritis and/or inflammatory bowel disease and/or asthma and/or allergic rhinitis comprising administering to a patient in need thereof an effective amount of a compound according to claim 1.

16. A compound according to claim 2 wherein $R^2$ is selected from the group consisting of H, Cl, $NH_2$, $CH_3$, $CH_2OH$ and $CH_2CH_3$.

17. A compound according to claim 3 wherein $R^1$ denotes $CH_3$ or $CH_2CH_3$.

18. A compound according to claim 6 wherein $R^{10}$ is selected from the group consisting of the group consisting of H; F; Cl; $OCH_3$; CN; $CH_3$; $CF_3$; $CF_2H$; $CFH_2$ and $S(=O)_2$—CH.

19. A compound according to claim 9 wherein $R^4$, $R^5$ and $R^6$ are selected from the group consisting of the group consisting of H; F; Cl; $OCH_3$; $OCHF_2$; $OCFH_2$; $OCF_3$; CN; $CH_3$; $CF_3$; $CF_2H$ and $CFH_2$.

* * * * *